(12) United States Patent
Zhao et al.

(10) Patent No.: US 11,204,353 B2
(45) Date of Patent: Dec. 21, 2021

(54) REAGENTS AND METHODS FOR DETECTING PROTEIN LYSINE 2-HYDROXYISOBUTYRYLATION

(71) Applicant: PTM BIO LLC, Chicago, IL (US)

(72) Inventors: Yingming Zhao, Chicago, IL (US); Lunzhi Dai, Chicago, IL (US)

(73) Assignee: PTM Biolab Inc., Hangzhou (CN)

( * ) Notice: Subject to any disclaimer, the term of this patent is extended or adjusted under 35 U.S.C. 154(b) by 56 days.

(21) Appl. No.: 16/251,822

(22) Filed: Jan. 18, 2019

(65) Prior Publication Data

US 2019/0145986 A1 May 16, 2019

Related U.S. Application Data

(62) Division of application No. 13/941,973, filed on Jul. 15, 2013, now abandoned.

(51) Int. Cl.
*C07K 16/18* (2006.01)
*G01N 33/68* (2006.01)
*C07K 16/44* (2006.01)

(52) U.S. Cl.
CPC ......... *G01N 33/6875* (2013.01); *C07K 16/18* (2013.01); *C07K 16/44* (2013.01); *G01N 2440/10* (2013.01)

(58) Field of Classification Search
CPC ........... G01N 33/6875; G01N 2440/10; C07K 16/18; C07K 16/44
See application file for complete search history.

(56) References Cited

U.S. PATENT DOCUMENTS

| | | | |
|---|---|---|---|
| 9,625,467 | B2 | 4/2017 | Zhao |
| 2008/0241862 | A1 | 10/2008 | Zhao et al. |
| 2009/0075284 | A1 | 3/2009 | Chinnaiyan et al. |

FOREIGN PATENT DOCUMENTS

| | | |
|---|---|---|
| CN | 102375065 A | 3/2012 |
| WO | WO 2012/024612 A1 | 2/2012 |

OTHER PUBLICATIONS

Lee et al. ("Antibody Production with Synthetic Peptides", Methods Mol. Biol., 2016; vol. 1474, pp. 25-47) (Year: 2016).*
Aksnes et al., Trends in Biochemical Sciences, 41(9):746-60 (2016).
Chen et al., Molecular & Cellular Proteomics, 6(5):812-9 (2007).
Chen et al., PLoS Genetics, 6(9):e1001093, pp. 1-18 (2010).
Dai et al., Nature Chemical Biology, 10:365-73 (2014).
First Office Action for Chinese Application No. 201410406258.1, dated Nov. 14, 2018, 23 pages.
Gao et al., Journal of Chromatography B., 853:303-13 (2007).
Kim and Yang, Trends in Biochemical Sciences, 36(4):211-20 (2011).
Kristensen, Beilstein J. Org. Chem, 11:446-68 (2015).
Lin et al., ACS Chem. Biol., 7:947-60 (2012).
Liu et al., Arthritis Research & Therapy, 14(R25):1-14 (2012).
Mukherjee et al., TRENDS in Biochemical Sciences, 32(5):210-16 (2007).
Wang et al., Theory and Application of Medical Experimental Technology, p. 176 (2004).
Final Office Action for U.S. Appl. No. 14/121,311, dated Mar. 9, 2018, 14 pages.
Allis et al., Proc Natl Acad Sci USA, 82:8048-52 (1985).
Ashburner et al., Nature Genetics, 25(1):25-29 (2000).
Bader and Hogue, BMC Bioinformatics, 4(2):1-27 pages (2003).
Benjamini and Hochberg, Journal of the Royal Statistical Society. Series B (Methodological), 57(1):289-300 (1995).
Bough and Rho, Epilepsia, 48(1):43-58 (2007).
Cahill and Veech, Trans Am Clin Climatol Assoc, 114:149-63 (2003).
Chen et al., Mol Cell Proteomics, 11(10)1048-62 (2012).
Choudhary et al., Science, 325:834-40 (2009).
Colaert et al., Nat Methods, 6(11):786-7 (2009).
Cox et al., J Proteome Res, 10:1794-1805 (2011).
Crooks et al., Genome Research, 14:1188-90 (2004).
Du et al., Science, 334(6057):806-9 (2011).
Finn et al., Nucleic Acids Research, 36:D281-8 (2008).
Finn and Dice, J Biol Chem, 280(27):25864-70 (2005).
Finn et al., Nucleic Acids Research, 42:D222-30 (2014).
Freeman et al., Epilepsy Research, 68:145-80 (2006).
Guarente, Cold Spring Harb Symp Quant Biol, 76:81-90 (2011).
Guarente, Cell Metab, 14:151-3 (2011).
Haberland et al., Nat Rev Genet, 10(1):32-42 (2009).
Hornbeck et al., Nucleic Acids Res, 40:D261-70 (2012).
Jensen et al., Nucleic Acids Research, 37:D412-16 (2009).
Kanehisa and Goto, Nucleic Acids Research, 28(1):27-30 (2000).
Kashiwaya et al., PNAS, 97(10):5440-44 (2000).
Katada et al., Cell, 148:24-28 (2012).
Lim et al., PLoS One, 6(9):1-10 (2011).
Linares, "Nanostructured labels for enhanced paper based immunoassay", Retrieved from https://edoc.ub.uni-muenchen.de/19313/Moura_Linares_Elisangela.pdf on Jul. 25, 2016, 2013, 148 pages.
Lu and Thompson, Cell Metab, 16(1):9-17 (2012).
Martinez-Outschoorn et al., Cell Cycle, 10(8):1271-86 (2011).
McNally and Hartman, J Neurochem, 121(1):28-35 (2012).
Mihaylova et al., Cell, 145(4):607-21 (2011).
Peng et al., Mol Cell Proteomics, 10(12):M111.012658-1-M111.012658-12 (2011).
Preuveneers et al., Biochem, J., 133:133-57 (1973).
Reusch et al., FEBS Letters, 527:319-22 (2002).
Ruepp et al., Nucleic Acids Research, 36:D646-50 (2008).
Sakabe et al., PNAS, 107(46):19915-20 (2010).
Schwartz and Gygi, Nature Biotechnology, 23(11):1391-8 (2005).
Shannon et al., Genome Research, 13:2498-2504 (2003).

(Continued)

*Primary Examiner* — Tracy Vivlemore
*Assistant Examiner* — Nam P Nguyen
(74) *Attorney, Agent, or Firm* — RatnerPrestia

(57) ABSTRACT

The invention provides an isolated peptide comprising a lysine 2-hydroxyisobutyrylation site, a lysine 2-hydroxyisobutyrylation specific affinity reagent that specifically binds to the peptide, and a method for detecting protein lysine 2-hydroxyisobutyrylation in a sample using the reagent.

6 Claims, 16 Drawing Sheets
(9 of 16 Drawing Sheet(s) Filed in Color)
Specification includes a Sequence Listing.

(56) References Cited

OTHER PUBLICATIONS

Shechter et al., Nature Protocols, 2(6):1445-57 (2007).
Shimazu et al., Science, 39(6116):211-14 (2013).
Taggart et al., J Biol Chem, 280(29):26649-52 (2005).
Wang et al., Proteomics, 11(10):2019-26 (2011).
Wellen et al., Science, 324(5930):1076-80 (2009).
Xie et al., Mol Cell Proteomics, 11(5):100-7 (2012).
Berger, S.L. The complex language of chromatin regulation during transcription. *Nature* 447, 407-12 (2007).
Chen, Y., Chen, W., Cobb, M.H. & Zhao, Y. PTMap—A sequence alignment software for unrestricted, accurate, and full-spectrum identification of post-translational modification sites. *Proc. Natl. Acad. Sci. U. S. A.* 106, 761-766 (2009).
Chi et al. , P., Allis, C.D. & Wang, G.G. Covalent histone modifications—miswritten, misinterpreted and mis-erased in human cancers. *Nat Rev Cancer* 10, 457-69 (2010).
Drogaris, P. et al. Histone deacetylase inhibitors globally enhance H3/H4 tail acetylation without affecting H3 lysine 56 acetylation. *Sci. Rep.* 2, 220, 12 pp. (2012).
Freitas, M.A., Sklenar, A.R. & Parthun, M.R. Application of mass spectrometry to the identification and quantification of histone post-translational modifications. *J. Cell. Biochem.* 92, 691-700 (2004).
Gaucher, J. et al. Bromodomain-dependent stage-specific male genome programming by Brdt. *EMBO J* 31, 3809-20 (2012).
Heintzman, N.D. et al. Distinct and predictive chromatin signatures of transcriptional promoters and enhancers in the human genome. *Nat. Genet.* 39, 311-318 (2007).
Kumps, A., Duez, P. & Mardens, Y. Metabolic, nutritional, iatrogenic, and artifactual sources of urinary organic acids: a comprehensive table. *Clin Chem* 48, 708-17 (2002).
Martin, C. & Zhang, Y. The diverse functions of histone lysine methylation. *Nat. Rev. Mol. Cell Biol.* 6, 838-849 (2005).
Maxwell, P.H. et al. The tumour suppressor protein VHL targets hypoxia-inducible factors for oxygen-dependent proteolysis. *Nature* 399, 271-5 (1999).
Mietton, F. et al. Weak but uniform enrichment of the histone variant macroH2A1 along the inactive X chromosome. *Mol. Cell. Biol.* 29, 150-156 (2009).
Montellier, E., Rousseaux, S., Zhao, Y. & Khochbin, S. Histone crotonylation specifically marks the haploid male germ cell gene expression program Post-meiotic male-specific gene expression. *BioEssays* 34, 187-193 (2012).
Moriniere, J. et al. Cooperative binding of two acetylation marks on a histone tail by a single bromodomain. *Nature* 461, 664-8 (2009).
Olsen, J.V. et al. Quantitative phosphoproteomics reveals widespread full phosphorylation site occupancy during mitosis. *Sci. Signaling* 3, No pp. given (2010).
Perche, P.Y. et al. Higher concentrations of histone macroH2A in the Barr body are correlated with higher nucleosome density. *Curr. Biol.* 10, 1531-1534 (2000).
Reynard, L.N. & Turner, J.M.A. Increased sex chromosome expression and epigenetic abnormalities in spermatids from male mice with Y chromosome deletions. *J. Cell Sci.* 122, 4239-4248 (2009).
Rohwerder, T. & Mueller, R.H. Biosynthesis of 2-hydroxyisobutyric acid (2-HIBA) from renewable carbon. *Microb. Cell Fact.* 9, No pp. given (2010).
Tan, M.-J. et al. Identification of 67 histone marks and histone lysine crotonylation as a new type of histone modification. *Cell (Cambridge, MA, U. S.)* 146, 1016-1028 (2011).
Whitfield, M.L. et al. Identification of genes periodically expressed in the human cell cycle and their expression in tumors. *Mol. Biol. Cell* 13, 1977-2000 (2002).
Wisniewski, J.R., Zougman, A. & Mann, M. Nepsilon-formylation of lysine is a widespread post-translational modification of nuclear proteins occurring at residues involved in regulation of chromatin function. *Nucleic Acids Res* 36, 570-7 (2008).
Hattori et al., Current Opinion in Structural Biology, 51:141-148 (2018).
Non Final Office Action for U.S. Appl. No. 16/454,686, dated Jan. 2, 2020, 25 pages.

\* cited by examiner

A.

B.

C.

A.

B.

C.

IF on tubules

| DNA | H4K8ac HP1g | Merge |

| DNA | H4K8 HP1g | Merge |

Scale 5 μm

A. GenBank database Accession No. P16403 (H1.2_HUMAN) (SEQ ID NO: 1)

MSETAPAAPAAAPPAEKAPVKKKAAKKAGGTPRKASGPPVSELITKAVAASKERSGVSLAALKKALAAAG
YDVEKNNSRIKLGLKSLVSKGTLVQTKGTGASGSFKLNKKAASGEAKPKVKKAGGTKPKKPVGAAKKPK
KAAGGATPKKSAKKTPKKAKKPAAATVTKKVAKSPKKAKVAKPKKAAKSAAKAVKPKAAKPKVVKPKKA
APKKK

B. GenBank database Accession No. P0C0S8 (H2A.1_HUMAN) (SEQ ID NO: 2)

MSGRGKQGGKARAKAKTRSSRAGLQFPVGRVHRLLRKGNYAERVGAGAPVYLAAVLEYLTAEILELAGN
AARDNKKTRIIPRHLQLAIRNDEELNKLLGKVTIAQGGVLPNIQAVLLPKKTESHHKAKGK

C. GenBank database Accession No. P33778 (H2B.1B_HUMAN) (SEQ ID NO: 3)

MPEPSKSAPAPKKGSKKAITKAQKKDGKKRKRSRKESYSIYVYKVLKQVHPDTGISSKAMGIMNSFVND
IFERIAGEASRLAHYNKRSTITSREIQTAVRLLLPGELAKHAVSEGTKAVTKYTSSK

D. GenBank database Accession No. P84243 (H33_HUMAN) (SEQ ID NO: 4)

MARTKQTARKSTGGKAPRKQLATKAARKSAPSTGGVKKPHRYRPGTVALREIRRYQKSTELLIRKLPFQR
LVREIAQDFKTDLRFQSAAIGALQEASEAYLVGLFEDTNLCAIHAKRVTIMPKDIQLARRIRGERA

E. GenBank database Accession No. P62805 (H4_HUMAN) (SEQ ID NO: 5)

MSGRGKGGKGLGKGGAKRHRKVLRDNIQGITKPAIRRLARRGGVKRISGLIYEETRGVLKVFLENVIRD
AVTYTEHAKRKTVTAMDVVYALKRQGRTLYGFGG

FIG. 8

A. GenBank database Accession No. P15864 (H12_MOUSE) (SEQ ID NO: 6)

MSEAAPAAPAAAPPAEKAPAKKKAAKKPAGVRRKASGPPVSELITKAVAASKERSGVSLAALKKALAAA
GYDVEKNNSRIKLGLKSLVSKGILVQTKGTGASGSFKLNKKAASGEAKPQAKKAGAAKAKKPAGAAKK
PKKATGAATPKKAAKKTPKKAKKPAAAAVTKKVAKSPKKAKVTKPKKVKSASKAVKPKAAKPKVAKAKK
VAAKKK

B. GenBank database Accession No. P22752 (H2A1_MOUSE) (SEQ ID NO: 7)

MSGRGKQGGKARAKAKTRSSRAGLQFPVGRVHRLLRKGNYSERVGAGAPVYLAAVLEYLTAEILELAGN
AARDNKKTRIIPRHLQLAIRNDEELNKLLGRVTIAQGGVLPNIQAVLLPKKTESHHKAKGK

C. GenBank database Accession No. P10853 (H2B1F/G/L_MOUSE) (SEQ ID NO: 8)

MPEPAKSAPAPKKGSKKAVTKAQKKDGKKRKRSRKESYSVYVYKVLKQVHPDTGISSKAM
GIMNSFVNDIFERIASEASR LAHYNKRSTITSREIQTAVRLLLPGELAKHAVSEGTKAVTKYTSSK

D. GenBank database Accession No. P84244 (H33_MOUSE) (SEQ ID NO: 9)

MARTKQTARKSTGGKAPRKQLATKAARKSAPSTGGVKKPHRYRPGTVALREIRRYQKSTELLIRKLPFQR
LVREIAQDFKTDLRFQSAAIGALQEASEAYLVGLFEDTNLCAIHAKRVTIMPKDIQLARRIRGERA

E. GenBank database Accession No. P62806 (H4_MOUSE) (SEQ ID NO: 10)

MSGRGKGGKGLGKGGAKRHRKVLRDNIQGITKPAIRRLARRGGVKRISGLIYEETRGVLKVFLENVIRD
AVTYTEHAKRKTVTAMDVVYALKRQGRTLYGFGG

FIG. 9

*S. cerevisiae*

A. GenBank database Accession No. P04911 (H2A.1) (SEQ ID NO: 11)

MSGGKGGKAGSAAKASQSRSAKAGLTFPVGRVHRLLRRGNYAQRIGSGAPVYLTAVLEYLAAEILELAG
NAARDNKKTRIIPRHLQLAIRNDDELNKLLGNVTIAQGGVLPNIHQNLLPKKSAKATKASQEL

B. GenBank database Accession No. P02294 (H2B.2) (SEQ ID NO: 12)

MSSAAEKKPASKAPAEKKPAAKKTSTSVDGKKRSKVRKETYSSYIYKVLKQTHPDTGISQKSMSILNSF
VNDIFERIATEASKLAAYNKKSTISAREIQTAVRLILPGELAKHAVSEGTRAVTKYSSSTQA

C. GenBank database Accession No. P61830 (H3) (SEQ ID NO: 13)

MARTKQTARKSTGGKAPRKQLASKAARKSAPSTGGVKKPHRYKPGTVALREIRRFQKSTELLIRKLPFQ
RLVREIAQDFKTDLRFQSSAIGALQESVEAYLVSLFEDTNLAAIHAKRVTIQKKDIKLARRLRGERS

D. GenBank database Accession No. P02309 (H4) (SEQ ID NO: 14)

MSGRGKGGKGLGKGGAKRHRKILRDNIQGITKPAIRRLARRGGVKRISGLIYEEVRAVLKSFLESVIRDS
VTYTEHAKRKTVTSLDVVYALKRQGRTLYGFGG

FIG. 10

*Tetrahymena thermophila*

A. GenBank database Accession No. P35065 (H2A.1) (SEQ ID NO: 15)

MSTTGKGGKA KGKTASSKQV SRSARAGLQF PVGRISRFLK NGRYSERIGT
GAPVYLAAVLEYLAAEVLEL AGNAAKDNKK TRIVPRHILL AIRNDEELNK LMANTTIADG
GVLPNINPML LPSKTKKSTE PEH

B. GenBank database Accession No. P08993 (H2B.1) (SEQ ID NO: 16)

MAPKKAPAAA AEKKVKKAPT TEKKNKKKRS ETFAIYIFKV LKQVHPDVGI SKKAMNIMNS
FINDSFERIA LESSKLVRFN KRRTLSSREV QTAVKLLLPG ELARHAISEG TKAVTKFSSS

C. GenBank database Accession No. I7LUZ3 (H3) (SEQ ID NO: 17)

MARTKQTARK STGAKAPRKQ LASKAARKSA PATGGIKKPH RFRPGTVALR EIRKYQKSTD
LLIRKLPFQR LVRDIAHEFK AELRFQSSAV LALQEAAEAY LVGLFEDTNL CAIHARRVTI
MTKDMQLARR IRGERF

D. GenBank database Accession No. P69152 (H4) (SEQ ID NO: 18)

MAGGKGGKGM GKVGAKRHSR KSNKASIEGI TKPAIRRLAR RGGVKRISSF IYDDSRQVLK
SFLENVVRDA VTYTEHARRK TVTAMDVVYA LKRQGRTLYG FGG

FIG. 11

*D. melanogaster*

A. GenBank database Accession No. P02255 (H1) (SEQ ID NO: 19)

MSDSAVATSASPVAAPPATVEKKVVQKKASGSAGTKAKKASATPSHPPTQQMVDASIKNLKERGGSSL
LAIKKYITATYKCDAQKLAPFIKKYLKSAVVNGKLIQTKGKGASGSFKLSASAKKEKDPKAKSKVLSAEK
KVQSKKVASKKIGVSSKKTAVGAADKKPKAKKAVATKKTAENKKTEKAKAKDAKKTGIIKSKPAATKAK
VTAAKPKAVVAKASKAKPAVSAKPKKTVKKASVSATAKKPKAKTTAAKK

B. GenBank database Accession No. P08985 (H2A.V) (SEQ ID NO: 20)

MAGGKAGKDSGKAKAKAVSRSARAGLQFPVGRIHRHLKSRTTSHGRVGATAAVYSAAILEYLTAEVLEL
AGNASKDLKVKRITPRHLQLAIRGDEELDSLIKATIAGGGVIPHIHKSLIGKKEETVQDPQRKGNVILSQA
Y

C. GenBank database Accession No. P02283 (H2B) (SEQ ID NO: 21)

MPPKTSGKAAKKAGKAQKNITKTDKKKKRKRKESYAIYIYKVLKQVHPDTGISSKAMSIMNSFVNDIFER
IAAEASRLAHYNKRSTITSREIQTAVRLLLPGELAKHAVSEGTKAVTKYTSSK

D. GenBank database Accession No. P02299 (H3) (SEQ ID NO: 22)

MARTKQTARKSTGGKAPRKQLATKAARKSAPATGGVKKPHRYRPGTVALREIRRYQKSTELLIRKLPFQR
LVREIAQDFKTDLRFQSSAVMALQEASEAYLVGLFEDTNLCAIHAKRVTIMPKDIQLARRIRGERA

E. GenBank database Accession No. P84040 (H4) (SEQ ID NO: 23)

MTGRGKGGKGLGKGGAKRHRKVLRDNIQGITKPAIRRLARRGGVKRISGLIYEETRGVLKVFLENVIRD
AVTYTEHAKRKTVTAMDVVYALKRQGRTLYGFGG

FIG. 12

*c. elegans*

A. GenBank database Accession No. P10771 (H1.1) (SEQ ID NO: 24)

MSDSAVVAAAVEPKVPKAKAAKAAKPTKVAKAKAPVAHPPYINMIKEAIKQLKDRKGASKQAILKFISQN
YKLGDNVIQINAHLRQALKRGVTSKALVQAAGSGANGRFRVPEKAAAAKKPAAAKKPAAAKKPAAAKKA
TGEKKAKKPAAAKPKKAATGDKKVKKAKSPKKVAKPAAKKVAKSPAKKAAPKKIAKPAAKKAAKPAAKA

B. GenBank database Accession No. P09855 (H2A) (SEQ ID NO: 25)

MSGRGKGGKAKTGGKAKSRSSRAGLQFPVGRLHRILRKGNYAQRVGAGAPVYLAAVLEYLAAEVLELA
GNAARDNKKTRIAPRHLQLAVRNDEELNKLLAGVTIAQGGVLPNIQAVLLPKKTGGDKE

C. GenBank database Accession No. P04255 (H2B.1) (SEQ ID NO: 26)

MPPKPSAKGAKKAAKTVTKPKDGKKRRHARKESYSVYIYRVLKQVHPDTGVSSKAMSIMNSFVNDVFE
RIAAEASRLAHYNKRSTISSREIQTAVRLILPGELAKHAVSEGTKAVTKYTSSK

D. GenBank database Accession No. P08898 (H3) (SEQ ID NO: 27)

MARTKQTARKSTGGKAPRKQLATKAARKSAPASGGVKKPHRYRPGTVALREIRRYQKSTELLIRRAPFQ
RLVREIAQDFKTDLRFQSSAVMALQEACEAYLVGLFEDTNLCAIHAKRVTIMPKDIQLARRIRGERA

E. GenBank database Accession No. P62784 (H4) (SEQ ID NO: 28)

MSGRGKGGKGLGKGGAKRHRKVLRDNIQGITKPAIRRLARRGGVKRISGLIYEETRGVLKVFLENVIRD
AVTYCEHAKRKTVTAMDVVYALKRQGRTLYGFGG

REAGENTS AND METHODS FOR DETECTING PROTEIN LYSINE 2-HYDROXYISOBUTYRYLATION

CROSS-REFERENCE TO RELATED APPLICATIONS

This application is a divisional application of U.S. application Ser. No. 13/941,973, filed on Jul. 15, 2013, and the contents of which are incorporated by reference herein, in their entireties and for all purposes.

REFERENCE TO U.S. GOVERNMENT SUPPORT

This invention was made with government support under Grant Nos. DK082664 and RR020389 awarded by the National Institute of Health. The United States has certain rights in the invention.

FIELD OF THE INVENTION

This invention relates to reagents and methods for detecting proteins having post-translational modifications. More particularly, it relates to peptides comprising a 2-hydroxyisobutyrylated lysine, and their uses to develop reagents and methods useful for detecting protein lysine 2-hydroxyisobutyrylation.

BACKGROUND OF THE INVENTION

Chromatin is decorated with a wide variety of protein post-translational modifications (PTMs), such as acetylation, methylation, phosphorylation and recently β-N-acetylglucosamine (O-GlcNAc) modifications. The regulatory potential of histone marks is well illustrated for histone lysine acetylation ($K_{ac}$) and lysine methylation. Small chemical differences at a given lysine residue, e.g., acetylation vs methylation, may associate with very different functional outputs. Moreover, subtle differences within the same family of modifications can be of functional significance. For instance, lysine methylation can be present in three forms: mono-, di- or tri-methylation. Depending on the methylation state and its position, histone lysine methylation can be involved in either the activation or repression of gene expression. For example, lysine monomethylation and lysine trimethylation of histone H3K4 respectively mark enhancers and promoters of active genes. The dysregulation of histone marks can lead to diverse diseases, such as cancer.

The differentiation of male germ cells offers a particularly interesting setting to explore the biological significance of new histone PTM. Indeed, during this process, the male genome undergoes several large-scale structural and functional changes, including the establishment of stage-specific expression patterns, and a genome-wide replacement of histones by transition proteins and protamines.

There remains a need for developing reagents and methods useful for detecting post-translational modifications of histones or nonhistone proteins linked to various diseases and disorders.

SUMMARY OF THE INVENTION

The present invention relates to the use of peptides comprising a 2-hydroxyisobutyrylated lysine ($K_{2ohibu}$) to develop reagents and methods for detecting protein lysine 2-hydroxyisobutyrylation, especially site specific lysine 2-hydroxyisobutyrylation.

An isolated peptide comprising a 2-hydroxyisobutyrylated lysine is provided. The isolated peptide may be derived from a histone protein or a fragment thereof. The histone protein may be derived from an organism selected from the group consisting of human, mouse, S. cerevisiae, Tetrahymena thermophila, D. melanogaster, and C. elegans. The isolated peptide may comprise an amino acid sequence having at least 70% identity to an amino acid sequence selected from the group consisting of SEQ ID NOs: 29-112. The isolated peptide may comprise an amino acid sequence selected from SEQ ID NOs: 29-112. The isolated peptide may comprise at least 2 amino acid residues on each of the N-terminal and C-terminal sides of the 2-hydroxyisobutyrylated lysine.

An isolated lysine 2-hydroxyisobutyrylation specific affinity reagent is also provided. It is capable of binding specifically to a peptide comprising a 2-hydroxyisobutyrylated lysine. The peptide may comprise an amino acid sequence selected from SEQ ID NOs: 29-112. The binding may be dependent on the presence of the 2-hydroxyisobutyrylated lysine but not a surrounding peptide sequence thereof in the peptide. The binding may be dependent on the presence of the 2-hydroxyisobutyrylated lysine and a surrounding peptide sequence thereof in the peptide. The lysine 2-hydroxyisobutyrylation specific affinity reagent may be a protein or an antibody.

A method for producing a lysine 2-hydroxyisobutyrylation specific affinity reagent that is a protein is provided. The method comprises screening a protein library using a peptide comprising a 2-hydroxyisobutyrylated lysine and at least two amino acid residues on each of the N-terminal and C-terminal sides of the 2-hydroxyisobutyrylated lysine. The protein library may be selected from the group consisting of a phage display library, a yeast display library, a bacterial display library, and a ribosome display library.

A method for producing a lysine 2-hydroxyisobutyrylation specific affinity reagent that is an antibody is also provided. The method comprises immunizing a host with a peptide comprising a 2-hydroxyisobutyrylated lysine and at least two amino acid residues on each of the N-terminal and C-terminal sides of the 2-hydroxyisobutyrylated lysine.

A method for detecting a 2-hydroxyisobutyrylated lysine in a protein or a fragment thereof is provided. The method comprises contacting the protein or a fragment thereof with the isolated lysine 2-hydroxyisobutyrylation specific affinity reagent capable of binding specifically to a peptide comprising a 2-hydroxyisobutyrylated lysine. The lysine 2-hydroxyisobutyrylation specific affinity reagent and the protein or a fragment thereof forms a binding complex. The method further comprise detecting the binding complex. The presence of the binding complex indicates the presence of a 2-hydroxyisobutyrylated lysine in the protein or a fragment thereof. In this method, the lysine 2-hydroxyisobutyrylation specific affinity reagent may be a protein or an antibody.

A method for determining the level of protein lysine 2-hydroxyisobutyrylation in a sample is provided. The method comprises detecting a 2-hydroxyisobutyrylated lysine in the sample.

A kit for detecting a 2-hydroxyisobutyrylated lysine in a protein of a fragment thereof is provided. The kit comprises an isolated lysine 2-hydroxyisobutyrylation specific affinity reagent capable of binding specifically to a peptide comprising a 2-hydroxyisobutyrylated lysine.

A kit for isolating a peptide containing a 2-hydroxyisobutyrylated lysine is also provided. The kit comprises an isolated lysine 2-hydroxyisobutyrylation specific affinity reagent capable of binding specifically to a peptide comprising a 2-hydroxyisobutyrylated lysine.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 7 shows protein sequences of human histone proteins (A) H1.2 (SEQ ID NO: 1), (B) H2A (SEQ ID NO: 2), (C) H2B (SEQ ID NO: 3), (D) H3 (SEQ ID NO: 4), and (E) H4 (SEQ ID NO. 5).

FIG. 8 shows protein sequences of mouse histone proteins (A) H1.2 (SEQ ID NO: 6), (B) H2A (SEQ ID NO: 7), (C) H2B (SEQ ID NO: 8), (D) H3 (SEQ ID NO: 9), and (E) H4 (SEQ ID NO: 10).

FIG. 9 shows protein sequences of *S. cerevisiae* histone proteins (A) H2A (SEQ ID NO: 11), (B) H2B (SEQ ID NO: 12), (C) H3 (SEQ ID NO: 13), and (D) H4 (SEQ ID NO: 14).

FIG. 10 shows protein sequences of *Tetrahymena* histone proteins (A) H2A (SEQ ID NO: 15), (B) H2B (SEQ ID NO: 16), (C) H3 (SEQ ID NO: 17), and (D) H4 (SEQ ID NO: 18).

FIG. 11 shows protein sequences of *D. melanogaster* histone proteins (A) H1 (SEQ ID NO: 19), (B) H2A (SEQ ID NO: 20), (C) H2B (SEQ ID NO: 21), (D) H3 (SEQ ID NO: 22), and (E) H4 (SEQ ID NO: 23).

FIG. 12 shows protein sequences of *c. elegans* histone proteins (A) H1 (SEQ ID NO: 24), (B) H2A (SEQ ID NO:

Figure 1:
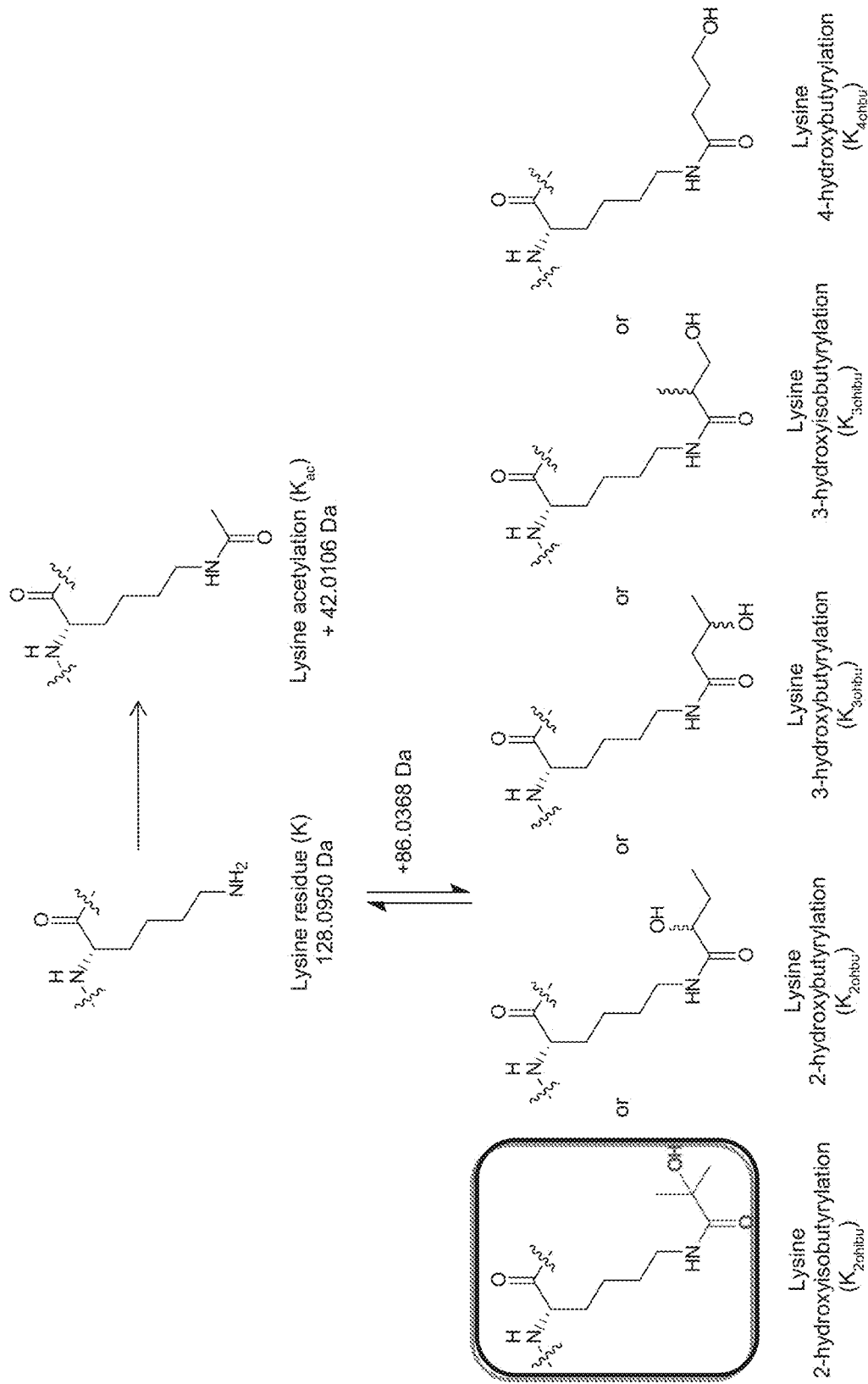
FIG. 1 shows chemical structures of lysine, acetyllysine, and other possible chemical structures of lysine modifications that may have the elemental composition of $C_4H_7O_2$ and induce a mass shift of +86.0368 Da.

25), (C) H2B (SEQ ID NO: 26), (D) H3 (SEQ ID NO: 27), and (E) H4 (SEQ ID NO: 28).

DETAILED DESCRIPTION OF THE INVENTION

The present invention is based on the discovery of a new type of histone marks, lysine 2-hydroxyisobutyrylation. In particular, over 60 novel histone lysine 2-hydroxyisobutyrylation sites in human and mouse cells have been identified. Genome-wide mapping of histone H4 lysine 8 2-hydroxyisobutyrylation (H4K8$_{2ohibu}$), in parallel with histone H4 lysine 8 acetylation (H4K8$_{ac}$), in spermatogenic cells, shows that H4K8$_{2ohibu}$ is a new indicator of gene transcriptional activity, demonstrating that lysine 2-hydroxyisobutyrylation represents a novel active histone mark with important functions in the physiological setting of male germ cell differentiation. Peptides derived from histone proteins or fragments thereof comprising a K$_{2ohibu}$ site may be used to generate reagents useful for detecting protein lysine 2-hydroxyisobutyrylation, especially for detecting site specific protein lysine 2-hydroxyisobutyrylation.

The term "peptide" used herein refers to a linear chain of two or more amino acids linked by peptide bonds. A peptide may have about 2, 3, 4, 5, 6, 7, 8, 9, 10, 11, 12, 13, 14, 15, 16, 17, 18, 19, 20, 25, 30, 40, 50, 100, 200 or more amino acids. The amino acids of a peptide may be modified, deleted, added or substituted. A peptide may be obtained using conventional techniques known in the art. For example, a peptide may be synthesized or obtained from a native or recombinant protein by enzymatic digestion.

The term "polypeptide" used herein refers to a peptide having at least 4 amino acids, preferably at least about 20 amino acids, regardless of post-translational modification. The term "protein" used herein refers to a biological molecule consisting of one or more polypeptides, regardless of post-translational modification. Each polypeptide in a protein may be a subunit. The polypeptide or protein may be in a native or modified form, and may exhibit a biological function or characteristics.

Where a protein is a single polypeptide, the terms "protein" and "polypeptide" are used herein interchangeably. A fragment of a polypeptide or protein refers to a portion of the polypeptide or protein having an amino acid sequence that is the same as a part, but not all, of the amino acid sequence of the polypeptide or protein. Preferably, a fragment of a polypeptide or protein exhibits a biological function or characteristics identical or similar to that of the polypeptide or protein.

The term "derived from" used herein refers to the origin or source from which a biological molecule is obtained, and may include naturally occurring, recombinant, unpurified or purified molecules. A biological molecule such as a peptide (e.g., a polypeptide or protein) may be derived from an original molecule, becoming identical to the original molecule or a variant of the original molecule. For example, a peptide derived from an original peptide may have an amino acid sequence identical or similar to the amino acid sequence of its original peptide, with at least one amino acid modified, deleted, inserted, or substituted. A derived peptide may have an amino acid sequence at least about 5%, 10%, 20%, 30%, 40%, 50%, 60%, 70%, 80%, 90%, 95%, 99% or 100%, preferably at least about 50%, more preferably at least about 80%, most preferably at least about 90%, identical to the amino acid sequence of its original peptide, regardless of post-translational modification. Preferably, a derived biological molecule (e.g., a peptide) may exhibit a biological function or characteristics identical or similar to that of the original biological molecule.

The term "antibody" used herein includes whole antibodies, and antigen binding fragments (or antigen-binding portions) and single chains thereof. A whole antibody can be either one of the two types. The first type refers to a glycoprotein typically having two heavy chains and two light chains, and includes an antigen binding portion. For example, the antibody may be a polyclonal or monoclonal antibody. The term "antigen binding portion" of an antibody used herein refers to one or more fragments of the antibody that retain the ability of specifically binding to an antigen. The second type refers to a heavy-chain antibody occurring in camelids that is also called Nanobody. The term "single-chain variable fragment" of an antibody used herein refers to a fusion protein of the variable regions of the heavy and light chains of the antibody, connected with a short linker peptide, for example, of about 20-25 amino acids, that retains the ability of specifically binding to an antigen.

An isolated peptide comprising a 2-hydroxyisobutyrylated lysine is provided. The term "2-hydroxyisobutyrylated lysine" used herein refers to a lysine residue that is 2-hydroxyisobutyrylated on its epsilon-amine group. It is also known as a 2-hydroxyisobutyryl lysine residue. The term "lysine 2-hydroxyisobutyrylation site" used herein refers to a lysine residue in a peptide, polypeptide or protein that may be 2-hydroxyisobutyrylated on the epsilon-amine group of the lysine residue. The term "lysine 2-hydroxyisobutyrylation" used herein refers to 2-hydroxyisobutyrylation on the epsilon-amine group of a lysine residue that generates a 2-hydroxyisobutyryl lysine residue or 2-hydroxyisobutyrylated lysine.

The peptide of the present invention may have at least about 3, 4, 5, 6, 7, 8, 9, 10, 11, 12, 13, 14, 15, 16, 17, 18, 19, 20, 30, 40, 50, 60, 70, 80, 90, 100, 150 or 200 amino acids. The peptide may have about 3-25 amino acids, preferably 5-20 amino acids, more preferably 6-14 amino acids.

The peptide of the present invention may be prepared using conventional techniques known in the art. The peptide may be derived from a protein, for example, a histone protein, or a fragment thereof, having a lysine 2-hydroxyisobutyrylation site. The histone protein may be derived from a eukaryotic cell. Examples of a eukaryotic cell include cells from a yeast (e.g., S. cerevisiae), an C. elegans, a Drosophila (e.g., D. melanogaster (S2)), a Tetrahymena (e.g., Tetrahymena thermophila), a mouse (e.g., M. musculus (MEF)), or a human. Preferably, the eukaryotic cell is a mammalian cell, for example, a human, primate, mouse, rat, horse, cow, pig, sheep, goat, chicken, dog or cat cell. More preferably, the eukaryotic cell is a human cell.

The histone protein may be a histone linker protein or a histone core protein. A histone linker protein may be selected from the members of the H1 family, including the H1F subfamily (e.g., H1F0, H1FNT, H1FOO, and H1FX) and the H1H1 subfamily (e.g., HIST1H1A, HIST1H1B, HIST1H1C, HIST1H1D, HIST1H1E and HIST1H1T). A histone core protein may a member of the H2A, H2B, H3 or H4 family. A histone core protein in the H2A family may be a member of the H2AF subfamily (e.g., H2AFB1, H2AFB2, H2AFB3, H2AFJ, H2AFV, H2AFX, H2AFY, H2AFY2, and H2AFZ), the H2A1 subfamily (e.g., HIST1H2AA, HIST1H2AB, HIST1H2AC, HIST1H2AD, HIST1H2AE, HIST1H2AG, HIST1H2AH, HIST1H2AI, HIST1H2AJ, HIST1H2AK, HIST1H2AL, and HIST1H2AM), or the H2A2 subfamily (e.g., HIST2H2AA3, HIST2H2AA4, HIST2H2AB, and HIST2H2AC). A histone core protein in the H2B family may be a member of the H2BF subfamily (e.g., H2BFM and H2BFWT), the H2B1 subfamily (e.g., HIST1H2BA, HIST1H2BB, HIST1H2BC, HIST1H2BD, HIST1H2BE, HIST1H2BF, HIST1H2BG, HIST1H2BH, HIST1H2BI, HIST1H2BJ, HIST1H2BK, HIST1H2BL, HIST1H2BM, HIST1H2BN, and HIST1H2BO), or the H2B2 subfamily (e.g., HIST2H2BE and HIST2H2BF). A histone core protein in the H3 family may be a member of the H3A1 subfamily (e.g., HIST1H3A, HIST1H3B, HIST1H3C, HIST1H3D, HIST1H3E, HIST1H3F, HIST1H3G, HIST1H3H, HIST1H3I, and HIST1H3J), the H3A2 subfamily (e.g., HIST2H3A, HIST2H3C, and HIST2H3D), or the H3A3 subfamily (e.g., HIST3H3), the H3A3 subfamily (e.g., H3F3A, H3F3B, and H3F3C). A histone core protein in the H4 family may be a member of the H41 subfamily (e.g., HIST1H4A, HIST1H4B, HIST1H4C, HIST1H4D, HIST1H4E, HIST1H4F, HIST1H4G, HIST1H4H, HIST1H4I, HIST1H4J, HIST1H4K, and HIST1H4L), or the H44 subfamily (e.g., HIST4H4).

The protein and gene sequences of histone proteins in various species are known in the art. For example, protein sequences of human H1.2, H2A, H2B, H3 and H4 histone proteins can be found in GenBank database Accession Nos. P16403 (H12_HUMAN) having SEQ ID NO: 1 (FIG. 7A), P04908 (H2A1B_HUMAN) having SEQ ID NO: 2 (FIG. 7B), P33778 (H2B1B_HUMAN) having SEQ ID NO: 3 (FIG. 7C), P84243 (H33_HUMAN) having SEQ ID NO: 4 (FIG. 7D) and P62805 (H4 HUMAN) having SEQ ID NO: 5 (FIG. 7E) respectively. The protein sequences of mouse histone proteins H1.2, H2A, H2B, H3 and H4 can be found in the GenBank database Accession Nos. P15864 (H12_MOUSE) having SEQ ID NO: 6 (FIG. 8A), P22752 (H2A1_MOUSE) having SEQ ID NO: 7 (FIG. 8B), Q64475 (H2B1B_MOUSE) having SEQ ID NO: 8 (FIG. 8C), P84244 (H33_MOUSE) having SEQ ID NO: 9 (FIG. 8D) and P62806 (H4_MOUSE) having SEQ ID NO: 10 (FIG. 8E), respectively. Histone protein sequences of other species such as *S. cerevisiae* (FIG. 9), *Tetrahymena* (FIG. 10), *D. melanogaster* (FIG. 11), and *C. elegans* (FIG. 12) are also known.

A fragment of a histone protein may have an amino acid sequence that is the same as a part, not all, of the amino acid sequence of the histone protein comprising at least one lysine 2-hydroxyisobutyrylation site. The histone protein fragment may have at least about 1, 2, 3, 4, 5, 6, 7, 8, 9, 10, 11, 12, 13, 14, 15, 16, 17, 18, 19, 20, 30, 40, 50, 60, 70, 80, 90, 100, 150 or 200 amino acids. The histone fragment may have about 3-25 contiguous amino acids, preferably about 5-20 contiguous amino acids, more preferably about 6-14 contiguous amino acids, of the histone protein covering at least one lysine 2-hydroxyisobutyrylation site in the histone protein.

The histone protein or fragment may have a 2-hydroxyisobutyrylated lysine at a lysine 2-hydroxyisobutyrylation site. The lysine 2-hydroxyisobutyrylation site may be any one of the lysine 2-hydroxyisobutyrylation sites in exemplary histone proteins of human (Table 1), mouse (Table 2), *S. cerevisiae* (Table 3), and *Tetrahymena* (Table 4).

A histone protein may be obtained from a biological sample or prepared using recombinant techniques. A histone protein fragment may be prepared by recombinant techniques, or by digesting the histone protein with an enzyme (e.g., trypsin). The lysine 2-hydroxyisobutyrylation site in the histone protein or fragment may be lysine 2-hydroxyisobutyrylated naturally or artificially. The presence of a 2-hydroxyisobutyrylated lysine may be confirmed by using conventional techniques known in the art, for example, mass spectrometry.

The peptide of the present invention may comprise an amino acid sequence having at least about 70%, 80%, 90%, 95% or 99%, preferably at least about 90%, more preferably 100%, identity to an amino acid sequence selected from the group consisting of SEQ ID NOs: 29-112. The peptide may encompass any lysine 2-hydroxyisobutyrylation site with or without its surrounding sequences from a histone proteins. The peptide may comprise more than one 2-hydroxyisobutyrylated lysine. The peptide may also comprise a protein post-translational modification other than 2-hydroxyisobutyrylated lysine, such as acetylated lysine or methylated lysine. The peptides may further comprise at least about 1, 2, 3, 4, 5, 5, 6, 7, 8, 9, 10 or more residues on either or both of N-terminal and C-terminal sides of the 2-hydroxyisobutyrylated lysine. Preferably, the peptide may comprise at least 2 amino acid residues on each of the N-terminal and C-terminal side of the 2-hydroxyisobutyrylated lysine. Exemplary peptides of the present invention are shown in Tables 1-4.

An isolated lysine 2-hydroxyisobutyrylation specific affinity reagent is also provided. The term "lysine 2-hydroxyisobutyrylation specific affinity reagent" used herein refers to a molecule that is capable of binding to a peptide, polypeptide or protein having a lysine 2-hydroxyisobutyrylation site, which may be a histone protein or a peptide of the present invention. The lysine 2-hydroxyisobutyrylation specific affinity reagent may be a protein, for example, an antibody. The lysine 2-hydroxyisobutyrylation site may be any lysine 2-hydroxyisobutyrylation site in any histone protein from any species. Examples of the lysine 2-hydroxyisobutyrylation sites include those in human (Table 1), mouse (Table 2), *S. cerevisiae* (Table 3), and *Tetrahymena* (Table 4), and homologous lysine sites in corresponding eukaryotic histone proteins.

In some embodiments, the lysine 2-hydroxyisobutyrylation specific affinity reagent binds a peptide, polypeptide or protein having a lysine 2-hydroxyisobutyrylation site that is 2-hydroxyisobutyrylated, having an affinity that is at least about 10, 50, 100, 500, 1000 or 5000 times higher than that for its counterpart when the site is not 2-hydroxyisobutyrylated.

In other embodiments, the lysine 2-hydroxyisobutyrylation specific affinity reagent binds a peptide, polypeptide or protein having a lysine 2-hydroxyisobutyrylation site that is not 2-hydroxyisobutyrylated, having an affinity that is at least about 10, 50, 100, 500, 1000 or 5000 times higher than that for its counterpart when the site is 2-hydroxyisobutyrylated. The lysine 2-hydroxyisobutyrylation specific affinity reagent may be a peptide, polypeptide or protein, which may be an antibody. Preferably, the peptide is a peptide of the present invention.

The lysine 2-hydroxyisobutyrylation specific affinity reagent may be site specific, i.e., the binding is dependent on the presence of the 2-hydroxyisobutyrylated lysine and its surrounding peptide sequence. The surrounding peptide sequence may include at least about 1, 2, 3, 4, 5, 5, 6, 7, 8, 9, 10 or more residues on either or both of N-terminal and C-terminal sides of the 2-hydroxyisobutyrylated lysine. For example, the binding depends on the presence of the 2-hydroxyisobutyrylated lysine and at least 2 amino acid residues on each of the N-terminal and C-terminal side of the 2-hydroxyisobutyrylated lysine.

The lysine 2-hydroxyisobutyrylation specific affinity reagent may not be site specific, i.e., the binding is dependent on the presence of the 2-hydroxyisobutyrylated lysine but not its surrounding peptide sequence. One example is an anti-lysine-2-hydroxyisobutyrylation pan antibody.

A method for producing the lysine 2-hydroxyisobutyrylation specific affinity reagent of the present invention is further provided.

Where the lysine 2-hydroxyisobutyrylation specific affinity reagent is a protein, the protein may be produced by screening a protein library (also known as a display library or a degenerated protein library) using the peptide of the present invention. The peptide may have at least two amino acid residues one each of the N-terminal and C-terminal sides of the 2-hydroxyisobutyrylated lysine. The protein library may consist of many degenerated protein sequences, which may comprise two regions: one or more fixed peptide sequence regions and a plurality of degenerated amino acid sequences. The protein library may be a phage protein library, a yeast protein library, bacterial protein library, ribosome protein library, or other synthetic protein library comprising peptides having randomized amino acid sequences.

Where the lysine 2-hydroxyisobutyrylation specific affinity reagent is an antibody, the antibody may be produced by different methods known in the art. For example, the production method may comprise immunizing a host with an antigenic peptide to produce the antibody. The method may further comprise collecting antisera from the host. The host may be a mammal suitable for producing antibodies. For example, the host may be a mouse, rabbit, goat, Camelidae family animal (such as Lama and camel), or cartilaginous fishes. Dependent on the host used, the generated antibody can contain either two chains (a heavy chain and a light chain) or one chain (or heavy chain-only antibody occurring in camelids) that is also called Nanobody.

The antigenic peptide may be derived from a histone protein or a fragment thereof comprising a lysine 2-hydroxyisobutyrylation site, which may be 2-hydroxyisobutyrylated or not. The antigenic peptide may comprise a peptide of the present invention. Examples of antigenic peptides having 2-hydroxyisobutyrylated lysine may comprise one or more of the peptides in Tables 1 and 2. Examples of antigenic peptides not having 2-hydroxyisobutyrylated lysine may have an amino acid sequence identical to those in Tables 1 and 2, except that the lysine 2-hydroxyisobutyrylation site is not 2-hydroxyisobutyrylated. The N-terminal or C-terminal end of any of these peptides may be extended by 1-20 residues.

The method may further comprise purifying the antibody from the antisera. The method may further comprise utilizing spleen cells from the host to generate a monoclonal antibody. In some embodiments, the antibody specifically binds to a histone protein or fragment having a lysine 2-hydroxyisobutyrylation site when the site is 2-hydroxyisobutyrylated, but not when the site is not 2-hydroxyisobutyrylated. In other embodiments, the antibody specifically binds to a histone protein or fragment having a lysine 2-hydroxyisobutyrylation site when the site is not 2-hydroxyisobutyrylated, but not when the site is 2-hydroxyisobutyrylated.

The method may further comprise deduce the antibody sequences by high-performance liquid chromatography (HPLC)-mass spectrometry analysis of the isolated antibodies and followed by protein sequence database search against all the possible IgG protein sequences (derived from cDNA sequences) from bone marrow (or B cells) of the immunized host. The IgG cDNA sequences can be obtained from conventional DNA sequencing technologies from IgG cDNAs that are generated by RT-PCR using the known art. The derived heavy- and light-chain variable regions (VH and VL) can be further paired (in case the IgG is from a two-chain antibodies from a host like mice or rabbit). Such a pairing is not necessary for those IgG derived from heavy chain-only antibody (or Nonabody) from Lama. The antibody can then be generated using the antibody sequence information using the known art.

A method for detecting a 2-hydroxyisobutyrylated lysine in a protein or its fragment is provided. The method comprises (a) contacting the protein or its fragment with a lysine 2-hydroxyisobutyrylation specific affinity reagent of the present invention to form a binding complex, and (b) detecting the binding complex. The presence of the binding complex indicates the presence of the 2-hydroxyisobutyrylated lysine in the protein or its fragment. The binding complex may be detected by using various conventional methods in the art. The protein may be a histone protein. The method may further comprise quantifying the amount of the binding complex. The amount of the binding complex may indicate the level of lysine 2-hydroxyisobutyrylation in the protein or its fragment.

For each detection method of the present invention, a kit is provided. The kit comprises a lysine 2-hydroxyisobutyrylation specific affinity reagent of the present invention. The kit may further comprise an instruction directing how to carry out the method.

A fusion protein reporter is provided. The fusion protein reporter comprises a core flanked by a donor fluorescent moiety and an acceptor fluorescent moiety. The core includes a peptide, which comprises a lysine 2-hydroxyisobutyrylation site and a lysine 2-hydroxyisobutyrylation binding domain. The term "lysine 2-hydroxyisobutyrylation binding domain" used herein refers to a region in a protein sequence capable of specific binding to the lysine 2-hydroxyisobutyrylation site.

The fusion protein reporter of the present invention may be useful for determining protein lysine 2-hydroxyisobutyrylation level in a sample or screening for an agent that regulates protein lysine 2-hydroxyisobutyrylation by using the fluorescence resonance energy transfer (FRET). The FRET involves the transfer of photonic energy between fluorophores when in close proximity. Donor fluorescent moieties and acceptor fluorescent moieties suitable for FRET are known in the art. In the fusion protein reporter, the donor fluorescent moiety may be selected from the group consisting of cyan fluorescent protein (CFP), enhanced cyan fluorescent protein (ECFP), and A206K mutants thereof, and the acceptor fluorescent moiety may be selected from the group consisting of yellow fluorescent protein (YFP), enhanced yellow fluorescence protein (EYFP), Citrine, Venus, and A206K mutants thereof.

The peptide in the fusion protein reporter may comprise a peptide of the present invention. It may be derived from a histone protein or fragment comprising a lysine 2-hydroxyisobutyrylation site, where the histone protein or fragment may be 2-hydroxyisobutyrylated or not at the lysine 2-hydroxyisobutyrylation site.

The lysine 2-hydroxyisobutyrylation site may be located in the N-terminus, C-terminus or the core region of a histone protein. The N-terminus, C-terminus, and core regions of histone proteins (e.g., human or mouse H1.2, H2A, H2B, H3 or H4) are known in the art.

The fusion protein reporter may comprise one or more lysine 2-hydroxyisobutyrylation binding domains. A lysine 2-hydroxyisobutyrylation binding domain may be derived from a lysine 2-hydroxyisobutyrylation specific affinity reagent of the present invention.

In some embodiments, the lysine 2-hydroxyisobutyrylation site in the peptide is not 2-hydroxyisobutyrylated, and the lysine 2-hydroxyisobutyrylation binding domain specifically binds to the lysine 2-hydroxyisobutyrylation site when the site is 2-hydroxyisobutyrylated, but not when the sites is not 2-hydroxyisobutyrylated.

In other embodiments, the lysine 2-hydroxyisobutyrylation site in the peptide is 2-hydroxyisobutyrylated, and the lysine 2-hydroxyisobutyrylation binding domain specifically binds to the lysine 2-hydroxyisobutyrylation site when the peptide is not lysine 2-hydroxyisobutyrylated, but not when the site is 2-hydroxyisobutyrylated.

The lysine 2-hydroxyisobutyrylation site may be conjugated to the lysine 2-hydroxyisobutyrylation binding domain with a linker molecule. The linker molecule may be a peptide have any amino acid sequence, and may have about 1-50 amino acids, preferably 1-30 amino acids, more preferably 2-15. In some embodiments, the linker molecule may be -Gly-Gly-. The length and contents of a linker molecule may be adjusted to optimize potential fluorescence resonance energy transfer (FRET) between the donor fluorescent moiety and the acceptor fluorescent moiety when the lysine 2-hydroxyisobutyrylation site in the fusion protein reporter is 2-hydroxyisobutyrylated or not, and bound by the lysine 2-hydroxyisobutyrylating binding domain.

The fusion protein reporter may further comprise a targeting polypeptide. The targeting polypeptide may be selected from the group consisting of a receptor ligand, a nuclear localization sequence (NLS), a nuclear export signal (NES), a plasma membrane targeting signal, a histone binding protein, and a nuclear protein.

A method for determining the level of protein lysine 2-hydroxyisobutyrylation in a sample. The method comprises detecting a 2-hydroxyisobutyrylated lysine in the sample. The method may comprise (a) contacting the sample with a fusion protein reporter of the present invention, and (b) comparing the level of fluorescence resonance energy transfer (FRET) between the donor fluorescent moiety and the acceptor fluorescent moiety after contacting with that before contacting. The level of FRET indicates the level of protein lysine 2-hydroxyisobutyrylation in the sample. The level of FRET may be increased or decreased after contacting.

A method for determining the level of protein de-lysine-2-hydroxyisobutyrylation in a sample is also provided. The method comprises (a) contacting the sample with a fusion protein reporter of the present invention, and (b) comparing the level of fluorescence resonance energy transfer (FRET) between the donor fluorescent moiety and the acceptor fluorescent moiety after contacting with that before contacting. The level of FRET indicates the level of protein de-lysine-2-hydroxyisobutyrylation in the sample. The level of FRET may be increased or decreased after contacting.

For the determination method of the present invention, a sample may be a biological sample (e.g., bodily fluid or serum). The biological sample may comprise a cell, a tissue biopsy, or a clinical fluid. The biological sample may be obtained from a subject (e.g., a mouse, rat, or human). The subject is healthy. The subject may have suffered from or may be predisposed to a protein lysine 2-hydroxyisobutyrylation or de-lysine-2-hydroxyisobutyrylation related disorder, which may be any disorder or disease linked to abnormal regulation of protein lysine 2-hydroxyisobutyrylation or de-lysine-2-hydroxyisobutyrylation, respectively. Examples of such disorder or disease may include cancer, neurodegenerative diseases, aging, metabolic disorder, and dysgenesis.

The determination method of the present invention may further comprise comparing the FRET level in the sample with a control FRET level. The control FRET level may be the FRET level in a control sample obtained from a subject, who is healthy or has not suffered from or predisposed to a protein lysine 2-hydroxyisobutyrylation related disorder. The FRET level in the sample may be higher or lower than the control FRET level.

The determination method of the present invention may further comprise adding an agent to the sample. In some embodiments, the agent is known to promote or inhibit protein lysine 2-hydroxyisobutyrylation. In other embodiments, the agent is a screening candidate for a regulator of protein lysine 2-hydroxyisobutyrylation. The screening candidate may be a compound or a biological molecule.

For each determination method of the present invention, a kit is provided. The kit comprises a fusion protein of the present invention. The kit may further comprise an instruction directing how to carry out the method.

A kit for isolating a peptide containing a 2-hydroxyisobutyrylated lysine is also provided. The kit comprises an isolated lysine 2-hydroxyisobutyrylation specific affinity reagent capable of binding specifically to a peptide comprising a 2-hydroxyisobutyrylated lysine.

A method for treating or preventing a protein lysine 2-hydroxyisobutyrylation related disease in a subject in need thereof is provided. The method comprises administering to the subject an effective amount of a composition comprising an agent that regulates protein lysine 2-hydroxyisobutyrylation. The agent may be a screen candidate identified by a determination method of the present invention. The protein lysine-2-hydroxyisobutyrylation may be histone lysine-2-hydroxyisobutyrylation.

A method for treating or preventing a protein or de-lysine-2-hydroxyisobutyrylation related disease in a subject in need thereof is provided. The method comprises administering to the subject an effective amount of a composition comprising an agent that regulates protein de-lysine-2-hydroxyisobutyrylation. The agent may be a screen candidate identified by a determination method of the present invention. The protein de-lysine-2-hydroxyisobutyrylation may be histone de-lysine-2-hydroxyisobutyrylation.

Example 1

Materials
Cell Culture and Synchronization.

HeLa cells were cultured in DMEM containing 10% FBS, 1% penicillin/streptomycin at 37° C., 5% $CO_2$. HeLa cells were arrested at G2/M phase by a thymidine-nocodazole block. Briefly, at 50% confluency, HeLa cells were treated with 2 mM thymidine (Sigma, St Louis, Mo., USA) for 24 hours. After releasing cells from the thymidine block for 3 hours, Nocodazole (Sigma, St Louis, Mo., USA) with a final concentration of 100 ng/ml was added for another 12 hours. The dish was gently shaken and the medium containing the mitotic cells were collected. The cells were washed with cold 1×PBS (137 mmol/L NaCl, 2.7 mmol/L KCl, 10.0 mmol/L $Na_2HPO_4$, 1.76 mmol/L $NaH_2PO_4$, pH=7.4) for 3 times and used for further downstream experiments.

Silac Labeling.

The SILAC media is formulated with SILAC Flex media supplemented with 10 ml 200 g/liter glucose, 10 ml 200 mM L-glutamine, 1.5 ml 10 g/L Phenol Red solution, 100 ml Dialyzed FBS, 10 ml 100× penicillin-Streptomycin, and 100 mg/L $^{13}C_6$-L-lysine.HCl or 100 mg/liter non-labeled $^{12}C_6$-L-lysine.HCl. The Final volume is 1 L after the above required components have been added. All reagents were purchased from Invitrogen. The media were sterile filtered. Cells were washed with 1×PBS buffer prior to exposure to SILAC Flex media. Cells were passaged 1:3 through dissociation in 0.25% trypsin. In the HeLa cells synchronization experiment, the thymine was dissolved in water without lysine and nocodazole was dissolved in DMSO without lysine. HeLa Cells underwent many passages before synchronization to achieve high isotopic amino acid incorporation. The incorporation efficiency was determined by mass spectrometry.

Chemical Propionylation.

Chemical propionylation before trypsin digestion procedure was showed as below: To 1.0 mg of histone sample dissolved in 300 μL of 0.1 M $NH_4HCO_3$ buffer (pH=8.0), 5.0 μL propionic anhydride was added. The pH of mixture was adjusted to keep pH between 8 and 9 by addition of 1 M NaOH with instant monitor. When the pH didn't decrease to below 8, another 5.0 μL propionic anhydride was added, and the pH of mixture was still kept pH between 8 and 9 by addition of 1 M NaOH until the pH didn't decrease. The propionylated histones were digested with trypsin (histone: trypsin=20:1) and used for immunoprecipitation. In chemical propionylation after trypsin digestion procedure, 20 μL instead of 5.0 μL propionic anhydride was used in each step.

Immunoprecipitation.

Briefly, anti-$K_{2ohibu}$ (PTM Biolabs, Inc. (Chicago, Ill.)), anti-$K_{cr}$ or anti-$K_{ac}$ antibodies was first immobilized to prewashed protein A agarose beads (GE Healthcare Biosciences, Pittsburgh, Pa.) at a density of 5 mg of antibody per ml drained beads. The tryptic peptides in $NH_4HCO_3$ solution were incubated with 15 μL antibody immobilized protein A beads at 4° C. overnight with gentle shaking. After incubation, the beads were washed three times with NETN buffer (50 mM Tris.HCl [pH 8.0], 100 mM NaCl, 1 mM EDTA, 0.5% NP40), twice with ETN buffer (50 mM Tris.HCl [pH 8.0], 100 mM NaCl, 1 mM EDTA) and once with water. The bound peptides were eluted from the beads by washing three times with 30 μL of 0.1 M glycine solution (pH=2.5). The elutes were combined and dried in a SpeedVac.

Results

Identification of a Mass Shift of +86.0354 Da at a Histone Lysine Residue

In order to discover new histone PTMs, the histone proteins from mouse spermatogenic cells, where a unique and genome-wide chromatin remodeling occurs, were digested with trypsin and the resulting tryptic peptides were analyzed by HPLC/MS/MS. The acquired MS/MS data was analyzed by the PTMap software, a non-restrictive sequence alignment algorithm that enables to detect a mass shift caused by a PTM. The analysis identified a modified H4 peptide, DAVTYTEHAKR (SEQ ID NO: 29), containing a mass shift of +86.0354 Da at its lysine residue (or H4K77). The only reasonable elemental composition responsible for this mass shift was $C_4H_7O_2$ (mass shift plus one proton) using ±0.02 Da mass tolerance and a maximum of 2 nitrogen atoms. According to the formula, we proposed five possible structures for the lysine modification: 2-hydroxyisobutyryl ($K_{2ohibu}$), 2-hydroxybutyryl ($K_{2ohbu}$), 3-hydroxybutyryl ($K_{3ohbu}$), 3-hydroxyisobutyryl ($K_{3ohibu}$) and 4-hydroxybutyryl ($K_{4ohbu}$) groups (FIG. 1).

The Mass Shift of +86.0354 Da is Caused by $K_{2ohibu}$

It is generally accepted that, if two peptides have the same MS/MS fragmentation patterns and are indistinguishable in HPLC chromatographic profiles, they have identical structures. To determine which of the five structure isomers is responsible for the mass shift, we first synthesized five Fmoc-protected lysine derivatives each bearing one of the five possible modifications. We then used them for the synthesis of five peptides that have the same peptide sequence (DAVTYTEHAKR) (SEQ ID NO: 29), but the different hypothesized modifications added at lysine residues, respectively.

We analyzed these synthetic peptides as well as the in vivo peptide by high-resolution MS. The MS/MS spectrum of the in vivo peptide (FIG. 2A) matched exactly with four of the synthetic peptides: DAVTYTEHAK$_{2ohibu}$R (DAVTYTEHAKR; SEQ ID NO: 29) (FIG. 2A), DAVTYTEHAK$_{(\pm)-2ohibu}$R (DAVTYTEHAKR; SEQ ID NO: 29), DAVTYTEHAK$_{(r)-3ohbu}$R (DAVTYTEHAKR; SEQ ID NO: 29) and DAVTYTEHAK$_{(s)-3ohbu}$R (DAVTYTEHAKR; SEQ ID NO: 29). However, the MS/MS spectrum of the 4-hydroxybutyrylated peptide (DAVTYTEHAK$_{4ohbu}$R (DAVTYTEHAKR; SEQ ID NO: 29)) had a significant neutral loss peak resulting from a weight loss of 86.03 Da based on its calculated molecular weight, leading to a different spectrum from that of the in vivo peptide. Thus, we concluded that the PTM in the in vivo peptide is not lysine 4-hydroxybutyrylation.

Figure 2:
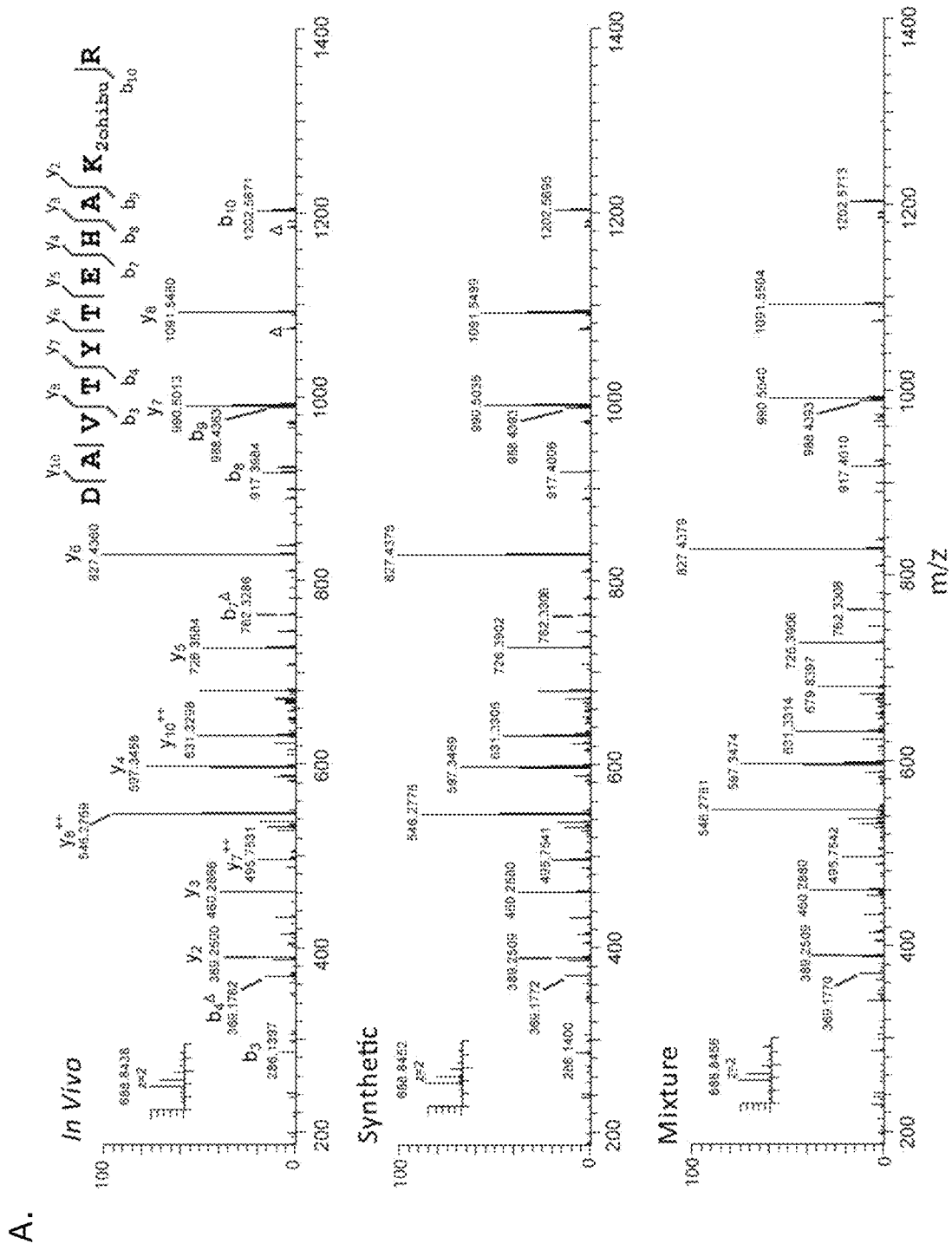
FIG. 2 shows verification of 2-hydroxyisobutyrylation at histone H4K77. (A) The MS/MS spectra of an in vivo peptide bearing a PTM (DAVTYTEHAK$_{+86.0354}$R) (DAVTYTEHAKR; SEQ ID NO: 29) (top), a synthetic lysine 2-hydroxyisobutyrylated peptide corresponding to the sequence of the in vivo peptide (middle), and a mixture of the two peptides (bottom). The label Δ designates b or y ions with water and/or ammonia loss. Insets show the precursor ion masses. (B) Extracted ion chromatograms (XICs) of a mixture of four synthetic peptides (DAVTYTEHAK$_{(\pm)-2ohibu}$R (DAVTYTEHAKR; SEQ ID NO: 29), DAVTYTEHAK$_{(r)-3ohibu}$R (DAVTYTEHAKR; SEQ ID NO: 29), DAVTYTEHAK$_{(s)-3ohibu}$R (DAVTYTEHAKR; SEQ ID NO: 29) and DAVTYTEHAK$_{4ohbu}$R (DAVTYTEHAKR; SEQ ID NO: 29)) and the in vivo peptide. (C) Extracted ion chromatograms (XIC) of the in vivo peptide (top), the synthetic peptide DAVTYTEHAK$_{2ohibu}$R (DAVTYTEHAKR; SEQ ID NO: 29) (middle), and the mixture of the both peptides (bottom).

Theoretically, two peptides with the same amino acid sequence and enantiomeric groups at the same PTM site will have the same retention times on a nonchiral HPLC column. This conclusion was confirmed in our co-elution experiment using the peptides DAVTYTEHAK$_{(r)-3ohbu}$R (DAVTYTEHAKR; SEQ ID NO: 29) and DAVTYTEHAK$_{(s)-3ohbu}$R (DAVTYTEHAKR; SEQ ID NO: 29). Therefore, in subsequent co-elution experiments, the use of racemic or enantiomeric peptides should have no influence on the co-elution results. To examine HPLC chromatographic profiles of the four synthetic peptides, we mixed the four remaining synthetic peptides (DAVTYTEHAK$_{2ohibu}$R (DAVTYTEHAKR; SEQ ID NO: 29), DAVTYTEHAK$_{(\pm)-2ohibu}$R (DAVTYTEHAKR; SEQ ID NO: 29), DAVTYTEHAK$_{(r)-3ohbu}$R (DAVTYTEHAKR; SEQ ID NO: 29), and DAVTYTEHAK$_{(s)-3ohbu}$R (DAVTYTEHAKR; SEQ ID NO: 29)) together with the in vivo one. The HPLC/MS/MS results revealed that these four peptides had different retention times and could be distinguished from the in vivo peptide bearing a mass shift of +86.0354 Da in the HPLC system (FIG. 2B). Accordingly, the pair-wise co-elution experiments can be used to determine the four putative structures.

Among the four possible structures, we found that the in vivo peptide co-eluted perfectly with the synthetic 2-hydroxyisobutyrylated peptide DAVTYTEHAK$_{2ohibu}$R (DAVTYTEHAKR; SEQ ID NO: 29) (FIG. 2C). However, the other three synthetic peptides, DAVTYTEHAK$_{(\pm)-2ohibu}$R (DAVTYTEHAKR; SEQ ID NO: 29), DAVTYTEHAK$_{(r)-3ohibu}$R (DAVTYTEHAKR; SEQ ID NO: 29), and DAVTYTEHAK$_{(s)-3ohibu}$R (DAVTYTEHAKR; SEQ ID NO: 29), did not co-elute with the in vivo peptide. These results indicate that the mass shift of the in vivo peptide is caused by $K_{2ohibu}$ instead of lysine 2-hydroxybutyrylation, 3-hydroxybutyrylation, and 3-hydroxyisobutyrylation. Together, the MS/MS and HPLC co-elution experiments demonstrated that the mass shift of +86.0354 Da at the lysine residue of the peptide DAVTYTEHAKR (SEQ ID NO: 29) is caused by $K_{2ohibu}$.

To further confirm the new modification $K_{2ohibu}$, we examined an additional peptide, VTIMPK$_{+86.03}$DIQLAR (SEQ ID NO: 47) with a mass shift of +86.03 Da, which were derived from mouse spermatogenic cells histones H3.

These experiments again unambiguously demonstrated that the mass shift of +86.03 Da was caused by $K_{2ohibu}$. Taken together, we tested the five possible structures of a lysine PTM caused by a mass shift of +86.03 Da in three in vivo peptides by MS/MS and HPLC co-elution experiments. Our results clearly showed that the mass shift of +86.03 Da at histone lysine residues is caused by $K_{2ohibu}$.

Verification of Histone $K_{2ohibu}$ by Western Blotting

Figure 3:
FIG. 3 shows histone K$_{2ohibu}$ in eukaryotic cells. (A) Western blotting analysis of the recombinant H4 and HeLa cell core histones. Immunoblot against H4 was used as a loading control. (B) Detection of K$_{2ohibu}$ and H4K8$_{2ohibu}$ in human HeLa cells, MEF cells, *Drosophila* S2 cells and yeast *S. cerevisiae* cells by Western blotting. (C) The K$_{2ohibu}$ sites from lysine 34 to lysine 120 in histone H2B shown in 3D structure of mouse nucleosome. H2B in the nucleosome is in ribbon shape and the other histones are displayed as backbones. The K$_{2ohibu}$ residues are highlighted in molecular ball shapes. (D) The lysine residues of all the K$_{2ohibu}$ sites in human and mouse histones are shown in red and bold: H1.2 corresponding to residues 2-212 of H12_MOUSE (SEQ ID NO: 6), H2A corresponding to residues 2-130 of H2A.1_HUMAN (SEQ ID NO: 2), H2B corresponding to residues 2-126 of H2B.1B-HUMAN (SEQ ID NO: 3), H3 corresponding to residues 2-136 of H33_HUMAN (SEQ ID NO: 4) and H4 corresponding to residues 2-103 of H4_HUMAN (SEQ ID NO: 5). The unique sites with K$_{2ohibu}$, but without K$_{cr}$ and K$_{ac}$ being reported are labeled with underscore. To make a comparison, the known K$_{ac}$ sites (labeled with a black triangle) and K$_{cr}$ sites (labeled with a green star) described in the literature were also listed.
Figure 3:
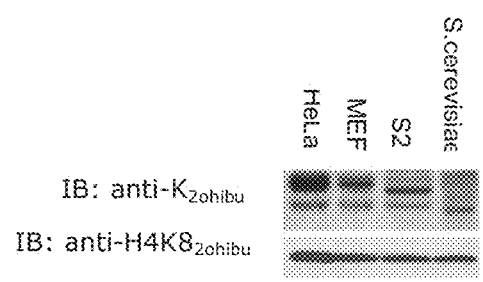
Figure 3:
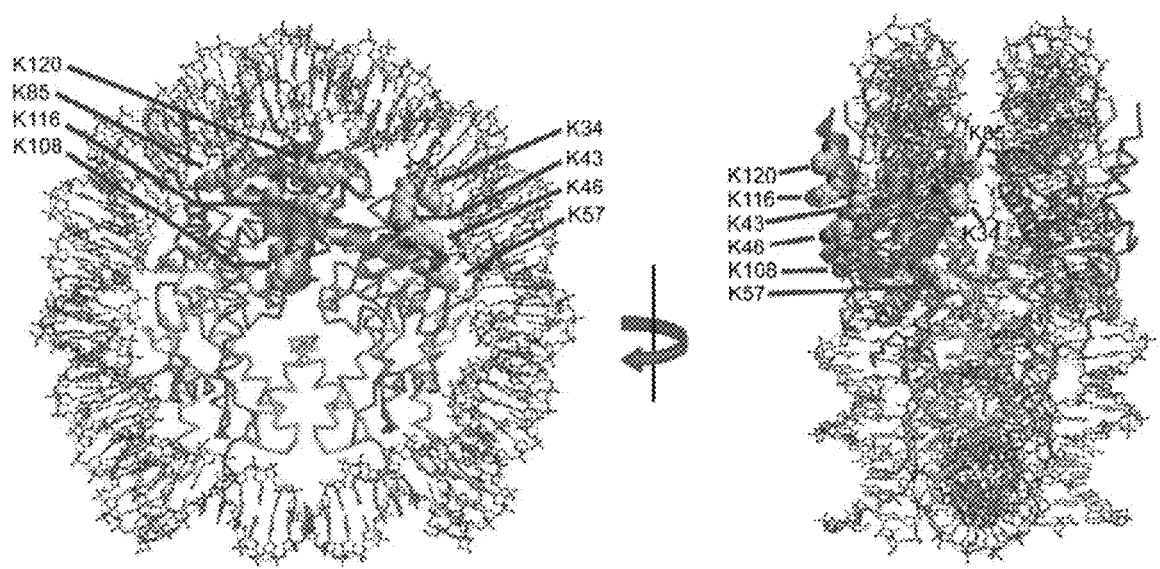
Figure 3:
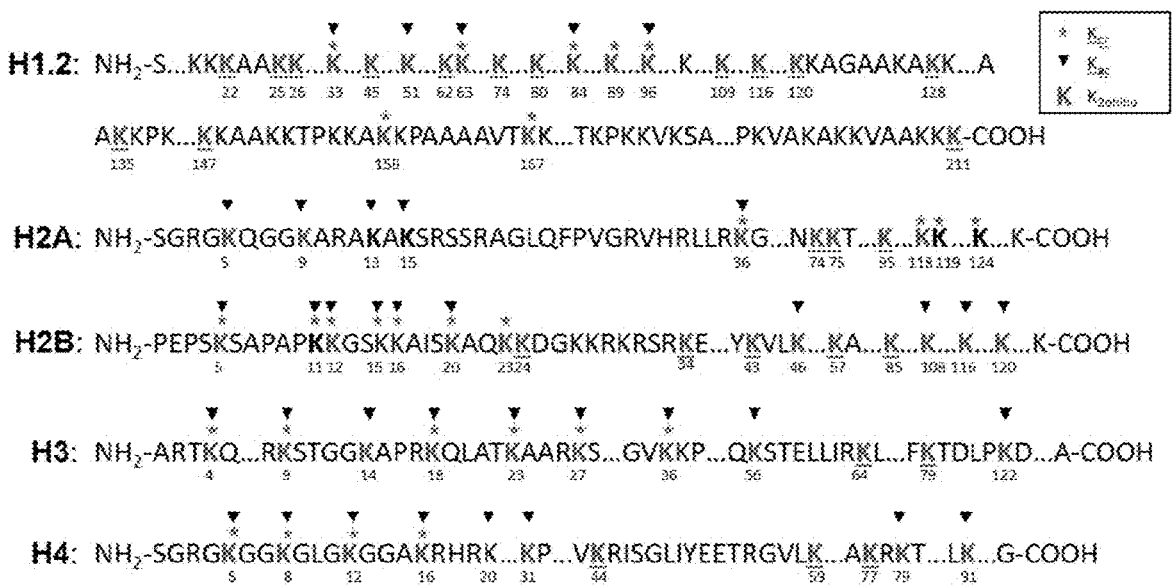

To corroborate the new PTM, we generated a pan anti-$K_{2ohibu}$ antibody and a sequence-specific antibody against H4K8$_{2ohibu}$. Both antibodies have good specificities based on dot-spot assays. Using Western blot, we specifically detected $K_{2ohibu}$ signal among all the HeLa cells core histone proteins. Likewise, using anti-H4K8$_{2ohibu}$ antibody, we detected H4K8$_{2ohibu}$ in HeLa cell histones, but not recombinant H4 (FIG. 3A). These results clearly demonstrate the existence of $K_{2ohibu}$ on human histones.

Histone $K_{2ohibu}$ is an Evolutionarily Conserved Mark

Using the pan anti-$K_{2ohibu}$ and sequence-specific anti-H4K8$_{2ohibu}$ antibodies, we detected $K_{2ohibu}$ on histones not only from HeLa cells, but also from mouse embryonic fibroblast (MEF) cells, Drosophila S2 cells and yeast S. cerevisiae cells (FIG. 3B). This result clearly indicates that $K_{2ohibu}$ is an evolutionarily-conserved in eukaryotic cells. To identify histone $K_{2ohibu}$ sites, we used an affinity-directed MS method, involving tryptic digestion of the extracted histones from the cells of interest, enrichment of $K_{2ohibu}$ peptides with anti-$K_{2ohibu}$ antibody, HPLC/MS/MS analysis and protein sequence database search. This study led to identification of 60 histone $K_{2ohibu}$ sites in mouse male germ cells (Table 1) and 22 histone $K_{2ohibu}$ sites in HeLa cells (Table 2).

Several interesting features were observed among histone $K_{2ohibu}$ sites. First, we detected 63 $K_{2ohibu}$ sites in human and mouse histones. For 27 of these 63 sites, neither acetylation nor crotonylation had been reported by the research community (FIG. 3D). Second, $K_{2ohibu}$ is located not only in N-terminal domains but also in other regions of core histones, a profile different from $K_{ac}$. As an example, eight $K_{2ohibu}$ sites were found to be located in the H2B globular domain between lysine 34 to lysine 120. We further examined the locations of $K_{2ohibu}$ lysine residues in the H2B core region and found that they are precisely located at surfaces involved in inter- or intra-nucleosome interactions in mouse spermatogenic cells (FIG. 3C). For example, H2BK43 in the L1 loop, H2BK85 in the L2 loop and H2BK34 are in direct contact with DNA. Accordingly, a change of charge state from positive (protonated amine group) to neutralized state (2-hydroxyisobutyrylated lysine) is highly likely to impact the association of H2B with DNA. These observations suggest different roles of histone $K_{2ohibu}$ from histone $K_{ac}$ and $K_{cr}$ in the regulation of chromatin structure and function. More interestingly, the occurrence of these nucleosome-destabilizing PTMs in the mouse spermatogenic cells is indicative of their potential role in the large-scale nucleosome disassembly that takes place in the post-meiotic cells.

To determine the stoichiometry of histone $K_{2ohibu}$ marks, we analyzed tryptic digests of core histones from unsynchronized and synchronized HeLa cells using a Stable isotope labeling by amino acids in cell culture (SILAC)-based method. Table 5 shows the absolute stoichiometry analysis of $K_{2ohibu}$ sites during mitosis. The stoichiometries of histone $K_{2ohibu}$ sites were calculated based on a previously published method which requires the quantification ratios of proteins, $K_{2ohibu}$ peptides and the corresponding unmodified tryptic peptides. Both $K_{2ohibu}$ peptides and protein quantification ratios were measured by Maxquant (v1.0.13.13) and the protein ratios were calculated using only unmodified peptides. The quantification ratios of the corresponding unmodified tryptic peptides were based on the Maxquant quantification ratios of the longest completely-cleaved tryptic form of $K_{2ohibu}$-bearing peptides. We were able to determine stoichiometry of four $K_{2ohibu}$ sites, H3K79, H2BK108, H4K91 and H1.2K63. Their stoichiometry reaches to 5.33% and 7.79% for H4K91 and H1.2K63, respectively, in the cells that were synchronized to G2/M phase. Stoichiometries for many $K_{ac}$ and methylation sites are lower than a few percentages. As an example, it was reported that the abundance of histone H3 lysine 56 acetylation (H3K56$_{ac}$), a histone mark with a role in genomic stability, is less than 0.1%. Our results suggest that the abundance of histone $K_{2ohibu}$ marks is likely to be in line with that of histone acetylation and methylation marks with low to medium abundance.

Labeling of Histone $K_{2ohibu}$ Marks by Isotopic 2-Hydroxyisobutyrate

The short-chain acyl-CoAs are the donor molecules for lysine acylations, e.g., acetyl-CoA for $K_{ac}$ reaction. Thus, most likely, 2-hydroxyisobutyryl-CoA is the cofactor for $K_{2ohibu}$ reaction. 2-Hydroxyisobutyryl-CoA is an intermediate in bacteria for the production of 2-hydroxyisobutyric acid, a building block for industrial polymer synthesis, and for the degradation of fuel oxygenates, methyl and ethyl tert-butyl ether, in bacteria and yeast. In human, 2-hydroxyisobutyric acid is one of the detectable organic acids that are associated with lactic acidosis.

To test if 2-hydroxyisobutyrate could be used by cells for $K_{2ohibu}$ via 2-hydroxyisobutyryl-CoA in a similar way as cells use acetate for lysine acetylation, we treated HeLa cells with 50 mM $D_6$-2-hydroxyisobutyrate for 72 hours. The isotopically labeled histone $K_{2ohibu}$ peptides were analyzed using MS. Our analysis detected $D_6$-labeled histone peptides. Table 6 shows the mass spectrometric analysis of the isotopic HeLa cells histone sample. The HeLa cells were treated with 50 mM $D_6$-2-hydroxyisobutyrate for 72 hours in DMEM medium. Only $D_6$-labeled $K_{2ohibu}$ sites were shown. This result implies that 2-hydroxyisobutyryl-CoA, originated from the precursor 2-hydroxyisobutyrate, is likely the cofactor for $K_{2ohibu}$.

Spatio-Temporal Labeling of Histone H4K8 by 2-Hydroxyisobutyrylation and Acetylation in Spermatogenic Cells We then examined the roles of H4K8$_{2ohibu}$ in the male germ cell specific transcriptional activities and chromatin remodeling. Indeed, our previous investigations of a critical spermatogenic factor, Brdt, specifically recognizing histone H4 lysine 5 acetylation (H4K5$_{ac}$) and H4K8$_{ac}$, indicate the important function of these two H4 lysine residues, in the control of male germ cell gene expression.

Figure 4:
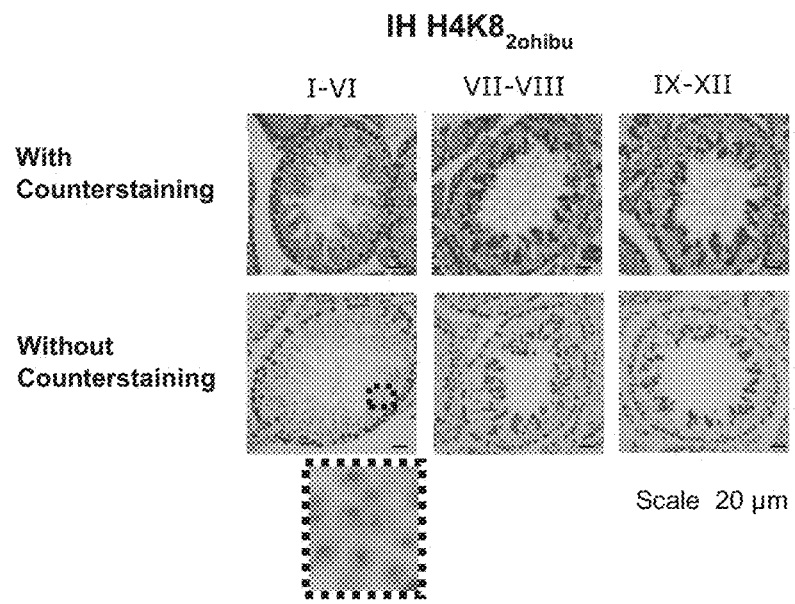
FIG. 4 shows spatiotemporal analyses of H4K8$_{2ohibu}$ and H4K8$_{ac}$ in mouse sperm cells. Sections from paraffin embedded testes were used for the detection of H4K8$_{2ohibu}$ (A) and H4K8$_{ac}$ (B) by immunohistochemistry (IH), with or without counterstaining. The tubule stages are indicated above each panel. The insets show a higher magnification of a dot-like structure observed in round spermatids. (C) Both H4K8$_{2ohibu}$ and H4K8$_{ac}$ marks are visualized by immunofluorescence (IF) in round spermatids from seminiferous tubule preparations. In each panel, the indicated PTMs (green) are co-detected along with HP1gamma (red).
Figure 4:
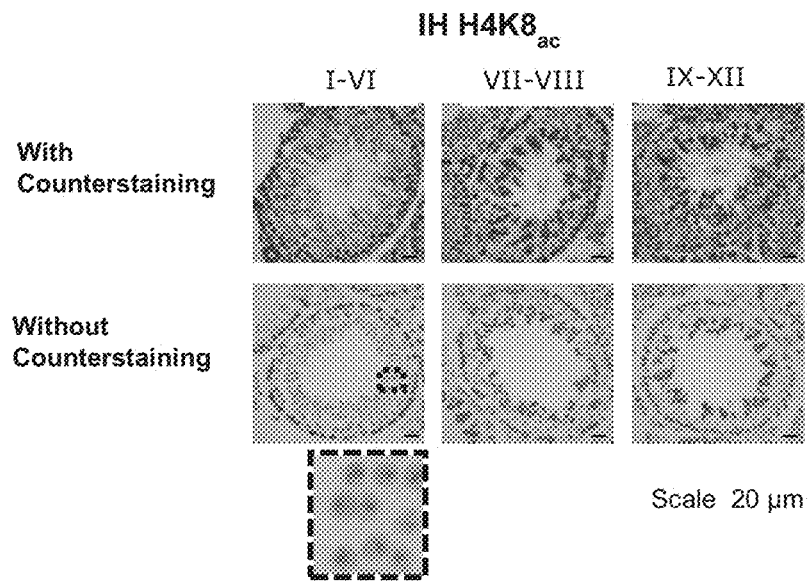
Figure 4:
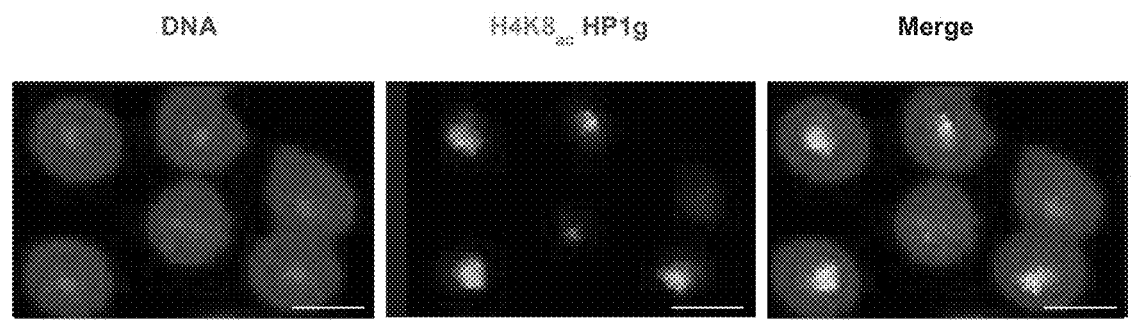
Figure 4:
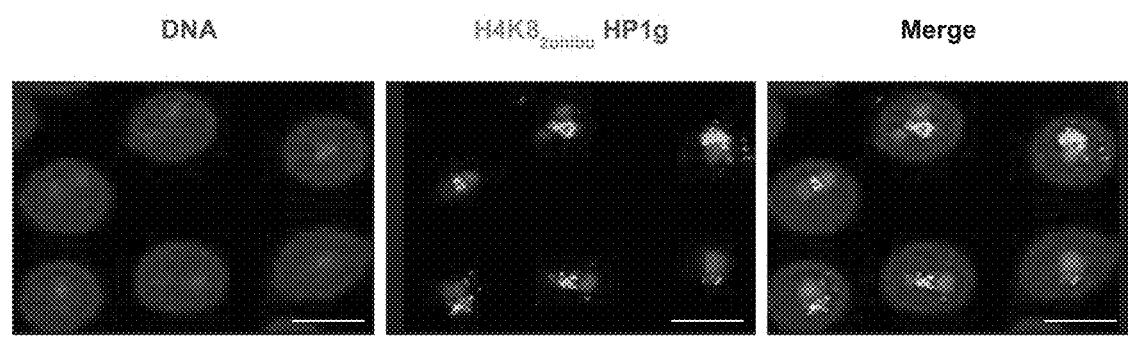

Toward this goal, we first analyzed spermatogenic cells by immunohistochemistry (IH) to examine the global dynamics of H4K8$_{2ohibu}$. The genome-wide distribution of this histone mark is dynamic and varies as a function of male germ cell differentiation (FIG. 4A). A clear labeling is observed in spermatogonia, which decreases in meiotic cells. In spermatocytes, the H4K8$_{2ohibu}$ labeling does not show any particular pattern, while in round spermatids, H4K8$_{2ohibu}$ forms a dot-like nuclear structure. At later stages, in elongating spermatids undergoing histone-to-transition protein (TP) replacement, the labeling becomes intense and genome-wide (FIG. 4A). Remarkably, a parallel analysis of H4K8$_{ac}$, a mark previously studied in spermatogenic cells, revealed a similar pattern of staining as H4K8$_{2ohibu}$ (FIG.

4B). Interestingly, the specific pattern of H4K8$_{ac}$ labeling in round spermatids was also observed.

In order to understand the nature of the dot-like structure observed in round spermatids on the histological testis sections, we investigated the dynamics of H4K8$_{2ohibu}$ using fluorescent immunodetection. In the mouse round spermatids, both H4K8$_{2ohibu}$ and H4K8$_{ac}$ marked a unique nuclear structure. In addition, the chromocenter, formed by the aggregation of all centromeric and pericentric chromosomal domains, forms a unique large heterochromatic structure, which is clearly visible by DAPI staining. The analysis of this structure with H4K8$_{2ohibu}$ staining shows the absence of this mark from the chromocenter, but the antibody labels an adjacent structure (FIG. 4C). The co-detection of HP1gamma, known to mark both the chromocenter and the adjacent sex chromosomes, together with H4K8$_{2ohibu}$, demonstrated that the H4K8$_{2ohibu}$-enriched structure corresponds to the sex chromosome, since it is absent from the chromocenter and perfectly co-localizes with the sex chromosomes. Interestingly, here again, the H4K8$_{ac}$ mark shows a similar pattern as H4K8$_{2ohibu}$, which is consistent with previous observations on the preferential association of this mark with sex chromosomes.

Figure 5:
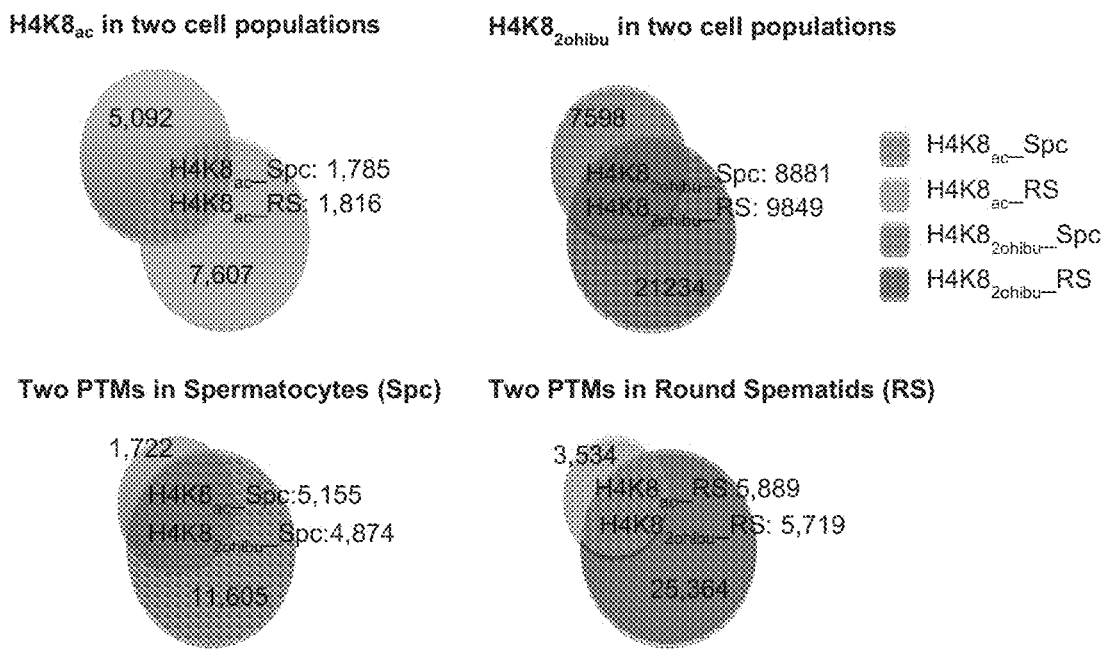
FIG. 5 shows high-Resolution mapping of H4K8$_{2ohibu}$ and H4K8$_{ac}$ in spermatocytes (meiotic cells) and round spermatids (post-meiotic cells). (A) The upper panels show the distributions of H4K8$_{2ohibu}$ (right) and H4K8$_{ac}$ (left) peaks between the two cell populations (spermatocytes (Spc) and round spermatids (RS)), while the lower panels show the distributions of overlapped and unique peaks for H4K8$_{2ohibu}$ and H4K8$_{ac}$ in Spc (left) and RS (right). (B) Metagene analysis of H4K8$_{2ohibu}$ and H4K8$_{ac}$ peaks with respect to their associated genes' transcription starting site (TSS). Color code for cell types and the histone marks are indicated. TES means transcription end site. (C) and (D) Distributions per chromosome of H4K8$_{ac}$ peaks (C) and H4K8$_{2ohibu}$ peaks (D). Peaks observed in spermatocytes and spermatids are represented in blue and red, respectively. The sex chromosomes are highlighted to emphasize the evolution of peak intensities on these chromosomes between spermatocytes and round spermatids.
Figure 5:
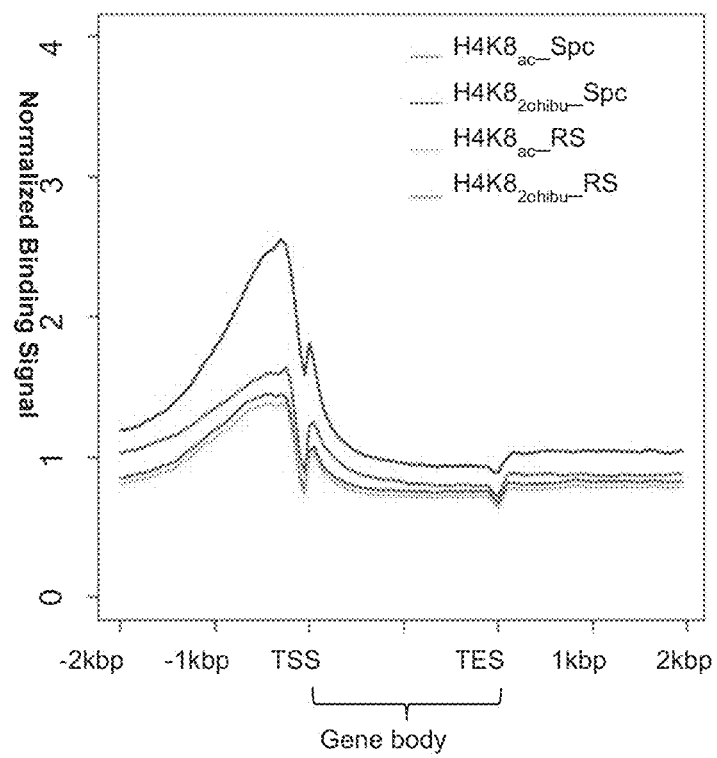
Figure 5:
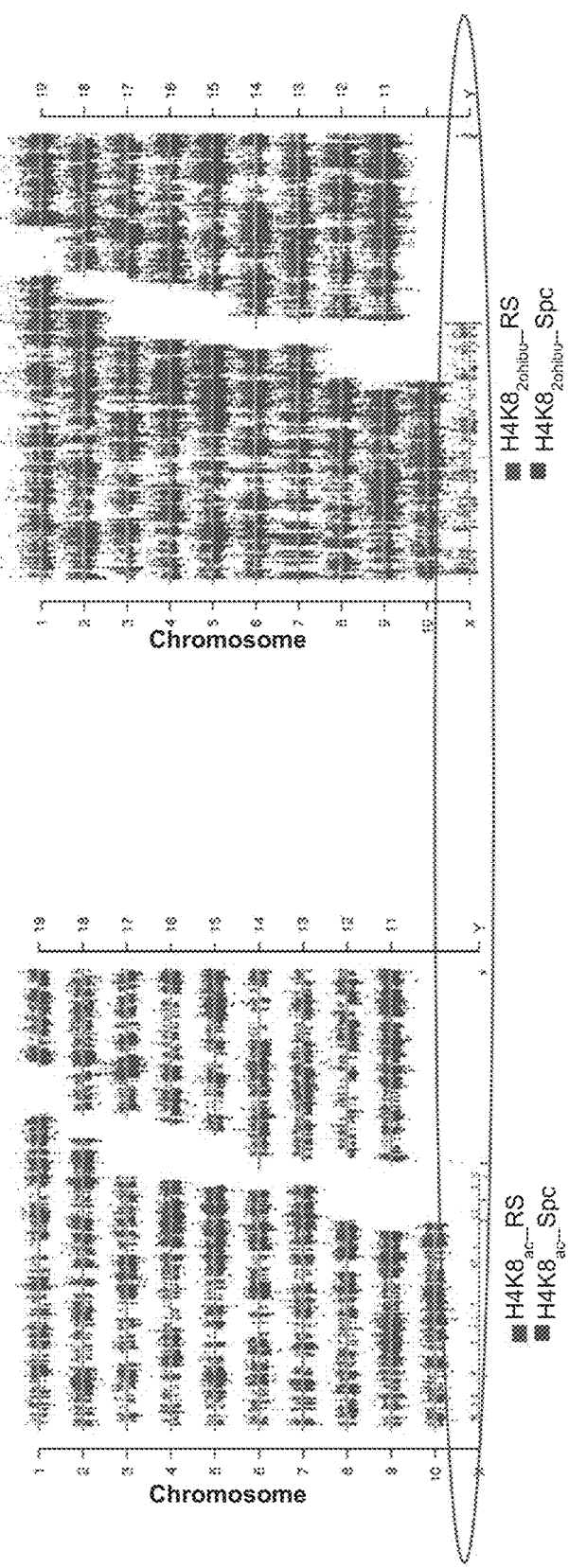

High-Resolution Genome-Wide Mapping of H4K8$_{2ohibu}$ and H4K8$_{ac}$ in Meiotic and Post-Meiotic Cells To gain functional insights into histone H4K8$_{2ohibu}$ and H4K8$_{ac}$, we prepared nuclei from enriched meiotic (spermatocytes) and post-meiotic (round spermatids) cells and used them for a high-resolution mapping of these marks in genomic localization by ChIP-seq. Our study shows that both marks are dynamic and that there is a significant re-distribution of H4K8$_{2ohibu}$ peaks between spermatocytes and round spermatids (FIG. 5A, upper). In addition, more than half of H4K8$_{ac}$ peaks are associated with nucleosomes bearing H4K8$_{2ohibu}$ mark (FIG. 5A, bottom).

The sex chromosomes (mainly the X) have a distinct global peaks distribution, where both marks are depleted compared to the autosomes, especially in spermatocytes (FIGS. 5C and 5D). This observation suggested that H4K8$_{2ohibu}$, like H4K8$_{ac}$, could be associated with the transcriptional activity of the chromosomes and that the relative depletion of these marks, on the X chromosome in spermatocytes, could be linked to the sex chromosome inactivation in these cells. Interestingly, in agreement with the immunodetection data, an increase of H4K8$_{2ohibu}$ peaks was observed on the X chromosome after the completion of meiosis (FIG. 5D). A similar phenomenon was observed for H4K8$_{ac}$, although with a much lesser degree than H4K8$_{2ohibu}$ (FIG. 5C).

Depletion of H4K8$_{ac}$ in the sex chromosomes in meiotic and post-meiotic cells is generally associated with the transcriptional silencing of the chromosomes. The similar observation for the depletion of H4K8$_{2ohibu}$ in spermatogenic cells suggests an association of this histone mark with gene expression. Indeed, a metagene analysis supported this hypothesis, showing that H4K8$_{2ohibu}$ and H4K8$_{ac}$ are both enriched at the transcriptional start sites (TSSs) of genes (FIG. 5B). Therefore, this result highlights H4K8$_{2ohibu}$'s possible roles in transcriptional control.

Figure 6:
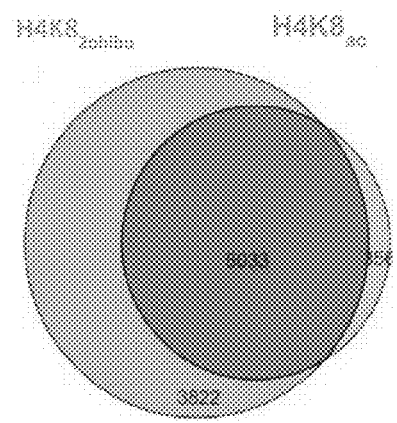
FIG. 6 shows that H4K8$_{2ohibu}$ is associated with genes with high transcriptional activity in male germ cells. (A) Number of genes associated with H4K8$_{2ohibu}$ and/or H4K8$_{ac}$ peaks in male germ cells (spermatocytes and/or round spermatids). (B) Expression of genes associated with H4K8$_{2ohibu}$ peaks in mouse tissues: distribution of H4K8$_{2ohibu}$ associated genes according to their sites of predominant expression in mouse tissues. (C) Gene expression patterns of testis-specific genes associated with H4K8$_{2ohibu}$ in spermatogenic cells: the heatmap shows the expression levels of H4K8$_{2ohibu}$ associated genes with a testis predominant expression in meiotic cells (spermatocytes: Spc) and post-meiotic cells (round spermatids: RS). Color scale: from green (low expression) to red (high expression). (D) Box plots comparing the distribution of expression levels of genes associated with H4K8$_{2ohibu}$ and/or H4K8$_{ac}$ peaks in meiotic cells (Spermatocytes: Spc) and in post-meiotic cells (Round spermatids: RS). *p<0.001 (unpaired t-test) showing a significant difference with the reference group of genes (not associated with H4K8$_{2ohibu}$ or H4K8$_{ac}$ peaks); **p<0.001 (unpaired t-test) showing a significant difference with all the other groups of genes including the reference group of genes (not associated with H4K8$_{2ohibu}$ or H4K8$_{ac}$ peaks) and the genes associated with either H4K8$_{ac}$ or H4K8$_{2ohibu}$ alone. (E) Proportions of X-linked genes and autosomal genes associated with H4K8$_{2ohibu}$ (left panel) or H4K8$_{ac}$ (right panel).
Figure 6:
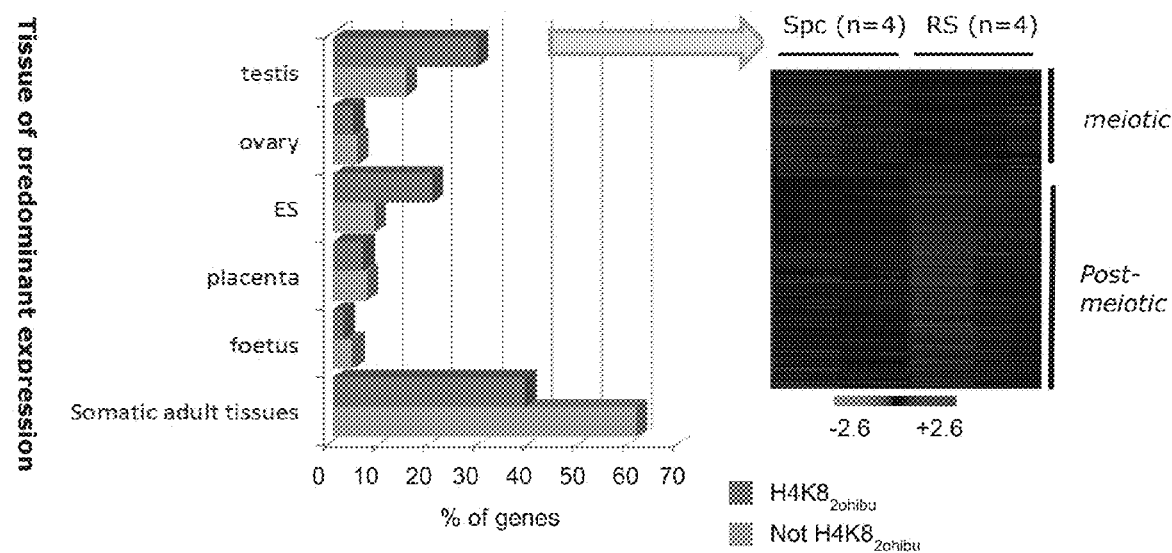
Figure 6:
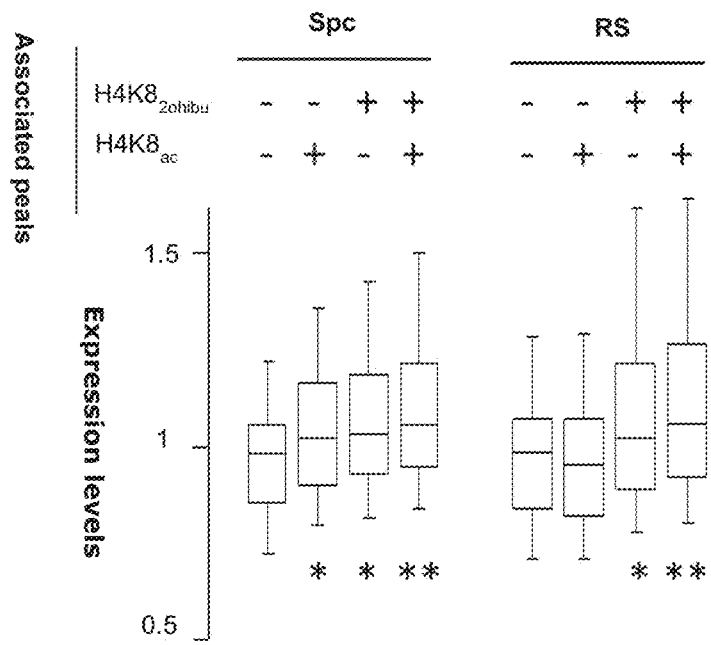
Figure 6:
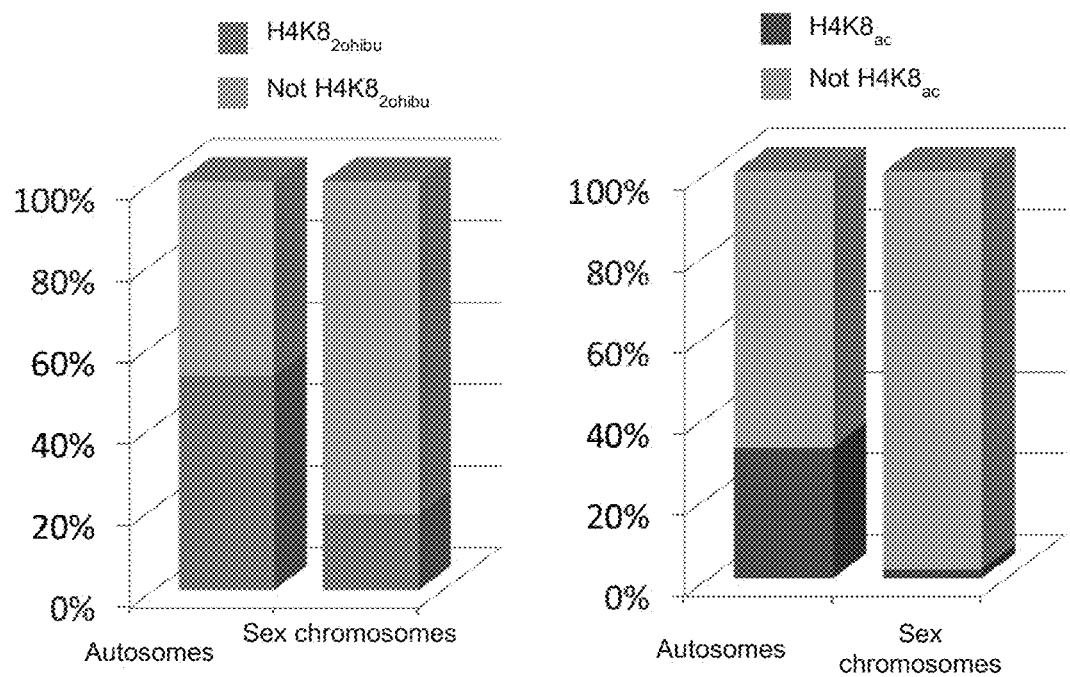

Epigenetic Gene Signposting by H4K8$_{2ohibu}$ and H4K8$_{ac}$ in Meiotic and Post-Meiotic Cells These data prompted us to examine the gene-containing fractions of the genome that are associated with these two marks. H4K8$_{2ohibu}$ peaks were found associated to 8855 genes in meiotic or post-meiotic spermatogenic cells (FIG. 6A). In both spermatocytes and in round spermatids, only a minor fraction of genes was associated with nucleosomes bearing H4K8$_{ac}$ alone, while the vast majority of the H4K8$_{ac}$-associated genes (93%) were co-localized in the genome with H4K8$_{2ohibu}$ (FIG. 6A). The gene expression patterns of the genes marked by H4K8$_{2ohibu}$, either alone or with H4K8$_{ac}$ (43% and 57% of H4K8$_{2ohibu}$-associated genes, respectively) were analyzed using transcriptomic data derived from normal mouse tissues (data available on the GEO website, GSE10744, GSE9954, GSE4193 and GSE21749), as previously described. Briefly, within the list of genes found associated with H4K8$_{2ohibu}$, we looked for those preferentially expressed in testis compared to other tissues. This study showed that 29% the H4K8$_{2ohibu}$-associated genes are testis-specific, and include meiotic and post-meiotic genes (FIGS. 6B and 6C).

Next, we examined if the genes associated with these two marks, alone or in combination, would show different transcriptional activities. To do so, stage-specific spermatogenic transcriptomes were downloaded (from the same studies as described above) and the mean expression levels of the gene categories associated with one or two marks were calculated. In spermatocytes, the expression levels of the genes bearing H4K8$_{2ohibu}$ alone are higher than those bearing none of the two H4K8 histone marks (FIG. 6D). In addition, combination of both marks slightly increases the effect. Unexpectedly, in round spermatids, H4K8$_{ac}$-marked genes do not show a different transcriptional activity compared to genes devoid of the two marks, which is different from our observations in spermatocytes (FIG. 6D, right). Interestingly, in these cells, the association of H4K8$_{2ohibu}$ alone with genes appeared as a strong indicator of a higher transcriptional activity and a combination of both marks further enhance gene expression.

Because of the relative enrichment of H4K8$_{2ohibu}$ in the post-meiotic sex chromosomes observed by both ChIP-seq and immunodetection, we wondered if there could be a relationship between H4K8$_{2ohibu}$ and histone crotonylation, a histone mark that has previously been shown increased on the sex chromosomes in post-meiotic cells. Interestingly, nearly no sex-linked gene was found associated with H4K8$_{ac}$ alone (FIG. 6E, right panel), despite a moderate enrichment of this mark in post-meiotic sex chromosomes and its apparent concentration on the sex chromosomes by immunodetection observed by us here and by others. Moreover, a relatively low proportion of sex chromosome-linked genes (18%) were associated with H4K8$_{2ohibu}$, while, in contrast, this mark was present on half of the autosomal genes (FIG. 6E, left panel). Interestingly, nearly all sex chromosome-linked genes associated with H4K8$_{2ohibu}$ were also included in the list of genes associated with histone crotonylation, where a pan—instead of sequence-specific anti-H4K8$_{cr}$ antibody was used. Taking into account the fact that no histone acetylation was found associated with these genes, this observation suggests that histone K$_{2ohibu}$, could be actually more directly involved than acetylation in activating the expression of at least a fraction of these genes in round spermatids, in the repressive context of the sex chromosomes.

Discussion

In this study, we identified the in vivo histone K$_{2ohibu}$ as a new histone mark. This PTM was robustly validated by (i) MS/MS analysis, (ii) HPLC co-elution, and (iii) Western blotting using pan and sequence-specific anti-K$_{2ohibu}$ antibodies. We subsequently identified 63 K$_{2ohibu}$ sites in histones, including 60 sites in mouse spermatogenic cells and 22 sites in human HeLa cells, more than the total number of histone $K_{ac}$ sites. Therefore, these histone $K_{2ohibu}$ sites add new elements to "histone language" and significantly enhance its complexity.

Diverse differences were observed among $K_{2ohibu}$, $K_{ac}$ and $K_{cr}$. First, the three histone marks show different patterns in different spermatogenic stages. These differences were consistently observed using ChIP-seq experiment. The immunostaining demonstrated that the histone $H4K8_{2ohibu}$ mark does not show any particular pattern in spermatocytes, but forms a dot-like nuclear structure in round spermatids cells, before becoming genome-wide at the time of histone replacement. Thus, $K_{2ohibu}$ is not only functionally distinct from $K_{ac}$, but also has regulatory mechanisms different from those of $K_{ac}$.

Second, $K_{2ohibu}$, $K_{ac}$ and $K_{cr}$ are located at different residues of histones (FIG. 3C). Our study identified 63 histone $K_{2ohibu}$ marks, more than the number of known histone $K_{ac}$ marks. The $K_{2ohibu}$ not only exists at the N-termini of the histones, but also at their main globular domains, while the majority of known $K_{cr}$ and $K_{ac}$ occur at the N-termini of the histones. Importantly, the stoichiometry of four $K_{2ohibu}$ sites (H3K79, H2BK108, H4K91 and H1.2K63) is comparable or even higher than that of many histone $K_{ac}$ marks with known biological functions.

Third, $K_{ac}$ and $K_{2ohibu}$ mark different groups of genes in spermatocytes. Interestingly, our study of genes associated with $H4K8_{2ohibu}$ show that this mark is a better indicator of their transcriptional activity in post-meiotic round spermatids than the acetylation at the same position.

Fourth, $K_{2ohibu}$ is structurally very different from lysine methylation, $K_{ac}$, or $K_{cr}$. Table 7 shows a comparison of changes of charge status, size, hydrophobicity caused by lysine, lysine dimethylation, $K_{ac}$, $K_{2ohibu}$ and $K_{cr}$. The hydrophobicity is determined based on calculated Log P value using Chemdraw software, in which the protonated residues were used for unmodified lysine and dimethylated lysine residues. "+" means a tendency to increase. "−" means a tendency to decrease. $K_{2ohibu}$ not only neutralizes the positive charge of lysine, but also induces much large change of its size. More importantly, $K_{2ohibu}$ has a hydroxyl group that enables the modified lysine to form hydrogen bonds with other molecules. Such a hydroxyl group is known to be important for the regulation of protein functions, e.g., HIF1.

Finally, $K_{2ohibu}$ is likely to result from the use of 2-hydroxyisobutyryl-CoA. Cellular metabolism has been suggested to be closely linked with epigenetic mechanisms. Thus, the $K_{2ohibu}$ pathway could provide an opportunity for cells to reprogram epigenetics networks through histone modifications, in response to the dynamic change of a cellular metabolite, 2-hydroxyisobutyryl-CoA.

A detailed analysis of $H4K8_{2ohibu}$ in parallel with $H4K8_{ac}$ allowed us to highlight a new epigenetic determinant of transcriptional activation. Indeed, when we consider the gene fraction of our ChIP-seq data, we found that $H4K8_{2ohibu}$ is a major mark associated with gene transcriptional activity and that $H4K8_{ac}$-bearing genes are largely included in this category constituting a sub-population of the $H4K_{2ohibu}$-labelled genes. Interestingly, in post-meiotic cells, $H4K8_{2ohibu}$, but not $H4K8_{ac}$ alone, indicates gene activity and the addition of $H4K8_{ac}$ is associated to a group of genes with higher activity. These observations suggest that the major transcription-associated mark in the post-meiotic spermatogenic cells is unexpectedly not $H4K8_{ac}$ but $H4K8_{2ohibu}$. This hypothesis receives strong support from a precise analysis of the situation of the sex chromosomes. Indeed, the chromosome-wide transcriptional inactivation that occurs in meiotic cells is found here associated with a depletion of both marks, in agreement with their involvement in gene activity.

However, we also show here that in post-meiotic round spermatids, $H4K8_{2ohibu}$, but not $H4K8_{cr}$, becomes associated with a faction of X-linked genes that is also labeled with histone crotonylation. There might be in fact a functional redundancy between $H4K8_{2ohibu}$ and $K_{cr}$ in this process. However, since pan anti-$K_{cr}$ antibody was used in the previous ChIP-seq study, some specific histone $K_{cr}$ sites other than H4K8, may mark similar genomic locations as histone $H4K8_{2ohibu}$. Based on these observations, we propose that $H4K_{2ohibu}$, although functionally similar to $H4K8_{ac}$ in terms of transcriptional activation, is of much wider use and ensures unique functions when gene activation needs to take place under general repressive conditions.

Another interesting observation is the disparity between ChIP-seq data and immunostaining data obtained in the post-meiotic sex chromosomes with anti-$H4K8_{2ohibu}$ and $H4K8_{ac}$ antibodies. Indeed, intense labeling of the sex chromosomes with the two histone marks was detected on testis sections by IH or by IF on seminiferous tubule sections. However, ChIP-seq data show that, although these marks are relatively enriched on the post-meiotic compared to the meiotic sex chromosomes, they remain relatively depleted on these chromosomes compared to the autosomes. Interestingly, the apparent enrichment of $H4K8_{ac}$ in the post-meiotic sex chromosomes observed by in situ staining has been previously described. This may be caused by a specific 3D organization of the sex chromosomes in round spermatids, which would create a local region with a high density of histone marks or with chromatin organization-dependent histone marks exposed for antibody recognition. We had previously described a similar phenomenon regarding the macroH2A histone variant. While the inactive X chromosome was intensely-labeled with anti-macroH2A antibodies, the enrichment of this histone variant on the X chromosome-linked genes was only moderate compared to autosomal genes.

The discovery of $K_{2ohibu}$ is just the beginning of the journey to study the possible diverse functions of this new modification. Extensive study of histone $K_{ac}$ and methylation in the past few decades has revealed their critical roles in epigenetics and transcriptional control. A similar biological potential is likely to exist for histone $K_{2ohibu}$. In addition, given the fact that all the known histone PTMs are also present in non-histone proteins, it is anticipated that $K_{2ohibu}$ should be present in non-histone proteins and should have nucleosome-independent functions as well. Future identification of the regulatory enzymes for $K_{2ohibu}$ and of its non-histone substrates will accelerate the characterization of its chromosome-independent functions.

The term "about" as used herein when referring to a measurable value such as an amount, a percentage, and the like, is meant to encompass variations of ±20% or ±10%, more preferably ±5%, even more preferably ±1%, and still more preferably ±0.1% from the specified value, as such variations are appropriate.

All documents, books, manuals, papers, patents, published patent applications, guides, abstracts, and other references cited herein are incorporated by reference in their entirety. Other embodiments of the invention will be apparent to those skilled in the art from consideration of the specification and practice of the invention disclosed herein. It is intended that the specification and examples be considered as exemplary only, with the true scope and spirit of the invention being indicated by the following claims.

REFERENCES

1. Chi, P., Allis, C. D. & Wang, G. G. Covalent histone modifications—miswritten, misinterpreted and miserased in human cancers. *Nat Rev Cancer* 10, 457-69 (2010).

2. Berger, S. L. The complex language of chromatin regulation during transcription. *Nature* 447, 407-12 (2007).
3. Martin, C. & Zhang, Y. The diverse functions of histone lysine methylation. *Nat. Rev. Mol. Cell Biol.* 6, 838-849 (2005).
4. Heintzman, N. D. et al. Distinct and predictive chromatin signatures of transcriptional promoters and enhancers in the human genome. *Nat. Genet.* 39, 311-318 (2007).
5. Montellier, E., Rousseaux, S., Zhao, Y. & Khochbin, S. Histone crotonylation specifically marks the haploid male germ cell gene expression program Post-meiotic male-specific gene expression. *BioEssays* 34, 187-193 (2012).
6. Chen, Y., Chen, W., Cobb, M. H. & Zhao, Y. PTMap-A sequence alignment software for unrestricted, accurate, and full-spectrum identification of post-translational modification sites. *Proc. Natl. Acad. Sci. U.S.A.* 106, 761-766 (2009).
7. Freitas, M. A., Sklenar, A. R. & Parthun, M. R. Application of mass spectrometry to the identification and quantification of histone post-translational modifications. *J. Cell. Biochem.* 92, 691-700 (2004).
8. Wisniewski, J. R., Zougman, A. & Mann, M. Nepsilon-formylation of lysine is a widespread post-translational modification of nuclear proteins occurring at residues involved in regulation of chromatin function. *Nucleic Acids Res* 36, 570-7 (2008).
9. Olsen, J. V. et al. Quantitative phosphoproteomics reveals widespread full phosphorylation site occupancy during mitosis. *Sci. Signaling* 3, No pp. given (2010).
10. Drogaris, P. et al. Histone deacetylase inhibitors globally enhance H3/H4 tail acetylation without affecting H3 lysine 56 acetylation. *Sci. Rep.* 2, 220, 12 pp. (2012).
11. Rohwerder, T. & Mueller, R. H. Biosynthesis of 2-hydroxyisobutyric acid (2-HIBA) from renewable carbon. *Microb. Cell Fact.* 9, No pp. given (2010).
12. Kumps, A., Duez, P. & Mardens, Y. Metabolic, nutritional, iatrogenic, and artifactual sources of urinary organic acids: a comprehensive table. *Clin Chem* 48, 708-17 (2002).
13. Moriniere, J. et al. Cooperative binding of two acetylation marks on a histone tail by a single bromodomain. *Nature* 461, 664-8 (2009).
14. Gaucher, J. et al. Bromodomain-dependent stage-specific male genome programming by Brdt. *EMBO J* 31, 3809-20 (2012).
15. Reynard, L. N. & Turner, J. M. A. Increased sex chromosome expression and epigenetic abnormalities in spermatids from male mice with Y chromosome deletions. *J. Cell Sci.* 122, 4239-4248 (2009).
16. Tan, M.-J. et al. Identification of 67 histone marks and histone lysine crotonylation as a new type of histone modification. *Cell* (Cambridge, Mass., U. S.) 146, 1016-1028 (2011).
17. Maxwell, P. H. et al. The tumour suppressor protein VHL targets hypoxia-inducible factors for oxygen-dependent proteolysis. *Nature* 399, 271-5 (1999).
18. Perche, P. Y. et al. Higher concentrations of histone macroH2A in the Barr body are correlated with higher nucleosome density. *Curr. Biol.* 10, 1531-1534 (2000).
19. Mietton, F. et al. Weak but uniform enrichment of the histone variant macroH2A1 along the inactive X chromosome. *Mol. Cell. Biol.* 29, 150-156 (2009).
20. Whitfield, M. L. et al. Identification of genes periodically expressed in the human cell cycle and their expression in tumors. *Mol. Biol. Cell* 13, 1977-2000 (2002).

TABLE 1

$K_{2ohibu}$ sites in human histone proteins

| Human Histone Protein | $K_{2ohibu}$ sites | Peptide sequences | SEQ ID NO |
|---|---|---|---|
| H1.2 | H1.2K45 | ASGPPVSELITK$_{2ohibu}$AVAASK | 30 |
| H1.2 | H1.2K51 | AVAASK$_{2ohibu}$ER | 31 |
| H1.2 | H1.2K62 | SGVSLAALK$_{2ohibu}$K | 32 |
| H1.2 | H1.2K63 | K$_{2ohibu}$ALAAAGYDVEK | 33 |
| H1.2 | H1.2K84 | LGLK$_{2ohibu}$SLVSK | 34 |
| H1.2 | H1.2K89 | SLVSK$_{2ohibu}$GTLVQTK | 35 |
| H1.2 | H1.2K96 | GTLVQTK$_{2ohibu}$GTGASGSFK | 36 |
| H2A | H2AK95 | NDEELNK$_{2ohibu}$LLGK | 37 |
| H2B | H2BK5 | PEPSK$_{2ohibu}$SAPAPK | 38 |
| H2B | H2BK46 | VLK$_{2ohibu}$QVHPDTGISSK | 39 |
| H2B | H2BK85 | LAHYNK$_{2ohibu}$R | 40 |
| H2B | H2BK108 | LLLPGELAK$_{2ohibu}$HAVSEGTK | 41 |
| H2B | H2BK116 | HAVSEGTK$_{2ohibu}$AVTK | 42 |
| H2B | H2BK120 | AVTK$_{2ohibu}$YTSSK | 43 |
| H3 | H3K23 | QLATK$_{2ohibu}$AAR | 44 |
| H3 | H3K56 | YQK$_{2ohibu}$STELLIR | 45 |
| H3 | H3K79 | EIAQDFK$_{2ohibu}$TDLR | 46 |
| H3 | H3K122 | VTIMPK$_{2ohibu}$DIQLAR | 47 |
| H4 | H4K31 | DNIQGITK$_{2ohibu}$PAIR | 48 |
| H4 | H4K77 | DAVTYTEHAK$_{2ohibu}$R | 29 |
| H4 | H4K79 | $_{2ohibu}$KTVTAMDVVYALK | 49 |
| H4 | H4K91 | TVTAMDVVYALK$_{2ohibu}$R | 50 |

TABLE 2

$K_{2ohibu}$ sites in mouse histone proteins

| Mouse Histone Protein | $K_{2ohibu}$ sites | Peptide sequences | SEQ ID NO |
|---|---|---|---|
| H1.2 | H1.2K22 | K$_{prop}$K$_{2ohibu}$AAK$_{prop}$K$_{prop}$PAGVR | 51 |
| H1.2 | H1.2K25 | K$_{prop}$K$_{prop}$AAK$_{2ohibu}$K$_{prop}$PAGVR | 51 |

TABLE 2-continued $K_{2ohibu}$ sites in mouse histone proteins

| Mouse Histone Protein | $K_{2ohibu}$ sites | Peptide sequences | SEQ ID NO |
|---|---|---|---|
| H1.2 | H1.2K26 | $K_{prop}$AA$K_{prop}K_{2ohibu}$PAGVR | 52 |
| H1.2 | H1.2K33 | $K_{2ohibu}$ASGPPVSELIT$K_{prop}$AVAAS$K_{2ohibu}$ | 53 |
| H1.2 | H1.2K51 | $K_{prop}$ASGPPVSELIT$K_{prop}$AVAAS$K_{2ohibu}$ER | 54 |
| H1.2 | H1.2K62 | SGVSLAAL$K_{2ohibu}$K | 32 |
| H1.2 | H1.2K74 | ALAAAGYDVE$K_{2ohibu}$NNSR | 55 |
| H1.2 | H1.2K80 | I$K_{2ohibu}$LGLK | 56 |
| H1.2 | H1.2K84 | $_{prop}$LGL$K_{2ohibu}$SLVS$K_{prop}$ | 34 |
| H1.2 | H1.2K96 | $_{prop}$GILVQT$K_{2ohibu}$GTGASGSF$K_{prop}$ | 57 |
| H1.2 | H1.2K109 | $_{prop}K_{2ohibu}$ASGEA$K_{prop}$PQA$K_{prop}$ | 58 |
| H1.2 | H1.2K116 | $_{prop}$AASGEA$K_{2ohibu}$PQA$K_{prop}$ | 59 |
| H1.2 | H1.2K120 | $_{prop}$AASGEA$K_{prop}$PQA$K_{2ohibu}K_{prop}$ | 60 |
| H1.2 | H1.2K128 | $_{prop}$A$K_{2ohibu}K_{prop}$PAGAA$K_{prop}$ | 61 |
| H1.2 | H1.2K135 | $_{prop}$A$K_{prop}K_{prop}$PAGAA$K_{2ohibu}K_{prop}$P$K_{prop}$ | 62 |
| H1.2 | H1.2K147 | $_{prop}K_{prop}$ATGAATP$K_{2ohibu}K_{prop}$ | 63 |
| H1.2 | H1.2K158 | $_{prop}K_{prop}$A$K_{2ohibu}K_{prop}$PAAAAVT$K_{prop}$ | 64 |
| H1.2 | H1.2K167 | $_{prop}K_{prop}$PAAAAVT$K_{2ohibu}K_{prop}$ | 65 |
| H1.2 | H1.2K211 | $K_{prop}$VAA$K_{prop}K_{prop}K_{2ohibu}$ | 66 |
| H2A | H1.2AK5, K9 | G$K_{2ohibu}$QGG$K_{2ohibu}$AR | 67 |
| H2A | H2AK36 | $K_{2ohibu}$GNYSER | 68 |
| H2A | H2AK74, K75 | DN$K_{2ohibu}K_{2ohibu}$TR | 69 |
| H2A | H2AK95 | NDEELN$K_{2ohibu}$LLGR | 70 |
| H2A | H2AK118 | VTIAQGGVLPNIQAVLLP$K_{2ohibu}$K | 71 |
| H2B | H2BK5 | $_{prop}$PEPA$K_{2ohibu}$SAPAP$K_{prop}$ | 72 |
| H2B | H2BK12 | $_{prop}$PEPA$K_{prop}$SAPAP$K_{prop}K_{2ohibu}$GSK | 73 |
| H2B | H2BK20 | $K_{prop}$AIS$K_{2ohibu}$AQ$K_{prop}$ | 74 |
| H2B | H2BK23 | AVT$K_{prop}$AQ$K_{2ohibu}K_{prop}$DG$K_{prop}K_{prop}$R | 75 |
| H2B | H2BK24 | AVT$K_{prop}$AQ$K_{prop}K_{2ohibu}$DG$K_{prop}K_{prop}$R | 75 |
| H2B | H2BK34 | $K_{2ohibu}$ESYSVYVYK | 76 |
| H2B | H2BK43 | KESYSVYVY$K_{2ohibu}$VLK | 77 |
| H2B | H2BK46 | VL$K_{2ohibu}$QVHPDTGISSK | 39 |
| H2B | H2BK57 | QVHPDTGISS$K_{2ohibu}$AMGIMNSFVNDIFER | 78 |
| H2B | H2BK85 | LAHYN$K_{2ohibu}$R | 40 |
| H2B | H2BK108 | LLLPGELA$K_{2ohibu}$HAVSEGTK | 41 |
| H2B | H2BK116 | HAVSEGT$K_{2ohibu}$AVTK | 42 |
| H2B | H2BK120 | AVT$K_{2ohibu}$YTSSK | 43 |
| H3 | H3K4 | T$K_{2ohibu}$QTAR | 79 |

TABLE 2-continued

$K_{2ohibu}$ sites in mouse histone proteins

| Mouse Histone Protein | $K_{2ohibu}$ sites | Peptide sequences | SEQ ID NO |
|---|---|---|---|
| H3 | H3K9 | $K_{2ohibu}$STGG$K_{ac}$APR | 80 |
| H3 | H3K14 | $K_{prop}$STGG$K_{2ohibu}$APR | 80 |
| H3 | H3K18 | $K_{2ohibu}$QLAT$K_{ac}$AAR | 81 |
| H3 | H3K23 | KQLAT$K_{2ohibu}$AAR | 81 |
| H3 | H3K27 | $K_{2ohibu}$SAPATGGV$K_{prop}K_{prop}$PHR | 82 |
| H3 | H3K36 | $K_{prop}$SAPATGGV$K_{2ohibu}K_{prop}$PHR | 82 |
| H3 | H3K56 | YQ$K_{2ohibu}$STELLIR | 45 |
| H3 | H3K64 | $K_{2ohibu}$LPFQR | 83 |
| H3 | H3K79 | EIAQDF$K_{2ohibu}$TDLR | 46 |
| H3 | H3K122 | VTIMP$K_{2ohibu}$DIQLAR | 47 |
| H4 | H4K5 | $K_{2ohibu}$GG$K_{ac}$GLG$K_{ac}$GGA$K_{ac}$R | 84 |
| H4 | H4K8 | G$K_{ac}$GG$K_{2ohibu}$GLG$K_{ac}$GGA$K_{ac}$R | 85 |
| H4 | H4K12 | GLG$K_{2ohibu}$GGA$K_{ac}$R | 86 |
| H4 | H4K16 | GG$K_{prop}$GLG$K_{prop}$GGA$K_{2ohibu}$R | 87 |
| H4 | H4K31 | DNIQGIT$K_{2ohibu}$PAIR | 48 |
| H4 | H4K44 | RGGV$K_{2ohibu}$R | 88 |
| H4 | H4K59 | GVL$K_{2ohibu}$VFLENVIR | 89 |
| H4 | H4K77 | DAVTYEHA$K_{2ohibu}$R | 29 |
| H4 | H4K79 | $K_{2ohibu}$TVTAMDVVYALK | 49 |
| H4 | H4K91 | KTVTAMDVVYAL$K_{2ohibu}$R | 90 |

TABLE 3

$K_{2ohibu}$ sites in S. cerevisiae histone proteins

| S. cerevisiae Histone Protein | $K_{2ohibu}$ sites | Peptide sequences | SEQ ID NO |
|---|---|---|---|
| H2A | H2AK13 | AGSAA$K_{2ohibu}$ASQSR | 91 |
| H2B | H2BK37 | $K_{2ohibu}$ETYSSYIYK | 92 |
| H2B | H2BK46 | ETYSSYIY$K_{2ohibu}$VLK | 93 |
| H2B | H2BK82 | IATEAS$K_{2ohibu}$LAAYNK | 94 |
| H2B | H2BK111 | LILPGELA$K_{2ohibu}$HAVSEGTR | 95 |
| H3 | H3K56 | FQ$K_{2ohibu}$STELLIR | 96 |
| H4 | H4K31 | DNIQGIT$K_{2ohibu}$PAIR | 48 |
| H4 | H4K77 | DSVTYTEHA$K_{2ohibu}$R | 97 |
| H4 | H4K79 | $K_{2ohibu}$TVTSLDVVYALK | 98 |
| H4 | H4K91 | TVTSLDVVYAL$K_{2ohibu}$R | 99 |

TABLE 4

$K_{2ohibu}$ sites in Tetrahymena macronuclear histone proteins

| Tetrahymena Histone Protein | $K_{2ohibu}$ sites | Peptide sequences | SEQ ID NO |
|---|---|---|---|
| H4 | H4K11 | GMG$K_{2ohibu}$VGAK | 100 |
| H4 | H4K79 | $K_{2ohibu}$TVTAMDVVYALK | 49 |
| H4 | H4K91 | TVTAMDVVYAL$K_{2ohibu}$R | 50 |
| H3 | H3K27 | $K_{2ohibu}$SAPATGGIK | 101 |
| H3 | H3K56 | YQ$K_{2ohibu}$STDLLIR | 102 |
| H3 | H3K64 | $K_{2ohibu}$LPFQR | 83 |
| H3 | H3K122 | VTIMT$K_{2ohibu}$DMQLAR | 103 |
| H2B | H2BK4 | $K_{2ohibu}$APAAAAEK | 104 |
| H2B | H2BK12 | $K_{ac}$APAAAAE$K_{2ohibu}$K | 105 |
| H2B | H2BK41 | VL$K_{2ohibu}$QVHPDVGISK | 106 |
| H2B | H2BK74 | IALESS$K_{2ohibu}$LVR | 107 |

TABLE 4-continued $K_{2ohibu}$ sites in *Tetrahymena* macronuclear histone proteins

| *Tetrahymena* Histone Protein | $K_{2ohibu}$ sites | Peptide sequences | SEQ ID NO |
|---|---|---|---|
| H2B | H2BK111 | HAISEGTK$_{2ohibu}$AVTK | 108 |
| H2B | H2BK115 | AVTK$_{2ohibu}$FSSSTN | 109 |
| H2A | H2AK17 | TASSK$_{2ohibu}$QVSR | 110 |

TABLE 5

Absolute stoichiometry analysis of $K_{2ohibu}$ sites during mitosis.

| $K_{2ohibu}$ sites | Peptide sequences | Stoichiometry of $K_{2ohibu}$ in unsynchronized HeLa cells | Stoichiometry of $K_{2ohibu}$ in G2/M phase HeLa cells |
|---|---|---|---|
| H3K79 | EIAQDFK$_{2ohibu}$TDLR | 0.60% | 1.45% |
| H2BK108 | LLLPGELAK$_{2ohibu}$HAVSEGTK | 0.64% | 1.54% |
| H4K91 | TVTAMDVVYALK$_{2ohibu}$R | 3.16% | 5.33% |
| H1.2K63 | SGVSLAALK$_{2ohibu}$K | 3.34% | 7.79% |

TABLE 6

Mass spectrometric analysis of the isotopic HeLa cells histone sample.

| $D_6$-labeled $K_{2ohibu}$ sites | Peptide sequences | SEQ ID NO |
|---|---|---|
| H2AK7 | AGGK$_{ac}$AGK$_{2ohibu}$DSGK | 111 |
| H2AK4 | AGGK$_{2ohibu}$AGK$_{ac}$DSGK | 111 |
| H4K8 | GGK$_{2ohibu}$GLGK$_{ac}$GGAK$_{ac}$R | 87 |
| H4K12 | GGK$_{ac}$GLGK$_{2ohibu}$GGAK$_{ac}$R | 87 |
| H4K12 | GLGK$_{2ohibu}$GGAK$_{ac}$R | 86 |
| H3K23 | K$_{ac}$QLATK$_{2ohibu}$AAR | 81 |
| H2BK5 | PEPAK$_{2ohibu}$SAPAPK | 72 |
| H2BK11 | SAPAPK$_{2ohibu}$K$_{ac}$GSK | 112 |

TABLE 7

A comparison of changes of charge status, size, hydrophobicity caused by lysine, lysine dimethylation, $K_{ac}$, $K_{2ohibu}$ and $K_{cr}$.

| comparison | PTMs | | | | |
|---|---|---|---|---|---|
| | K | $K_{me2}$ | $K_{ac}$ | $K_{2ohibu}$ | $K_{cr}$ |
| pI | 0 | + | − | − | − |
| Size | 0 | + | + | +++ | ++ |
| Hydrophobicity | 0 | +++ | + | ++ | ++++ |

What is claimed:

1. A method for producing an isolated affinity reagent, comprising immunizing a host with an isolated peptide comprising a 2-hydroxyisobutyrylated lysine, wherein the peptide comprises the amino acid sequence selected from the group consisting of DAVTYTEHAK$_{2ohibu}$R (SEQ ID NO: 29), ASGPPVSELITK$_{2ohibu}$AVAAS (SEQ ID NO: 30), AVAASK$_{2ohibu}$ER (SEQ ID NO: 31), SGVSLAALK$_{2ohibu}$K (SEQ ID NO: 32), K$_{2ohibu}$ALAAAGYDVEK (SEQ ID NO: 33), LGLK$_{2ohibu}$SLVSK (SEQ ID NO: 34), $_{prop}$LGLK$_{2ohibu}$SLVSK$_{prop}$ (SEQ ID NO: 34), SLVSK$_{2ohibu}$GTLVQTK (SEQ ID NO: 35), GTLVQTK$_{2ohibu}$GTGASGSFK (SEQ ID NO: 36), NDEELNK$_{2ohibu}$LLGK (SEQ ID NO: 37), PEPSK$_{2ohibu}$SAPAPK (SEQ ID NO: 38), VLK$_{2ohibu}$QVHPDTGISSK (SEQ ID NO: 39), LAHYNK$_{2ohibu}$R (SEQ ID NO: 40), LLLPGELAK$_{2ohibu}$HAVSEGTK (SEQ ID NO: 41), HAVSEGTK$_{2ohibu}$AVTK (SEQ ID NO: 42), AVTK$_{2ohibu}$YTSSK (SEQ ID NO: 43), QLATK$_{2ohibu}$AAR (SEQ ID NO: 44), YQK$_{2ohibu}$STELLIR (SEQ ID NO: 45), EIAQDFK$_{2ohibu}$TDLR (SEQ ID NO: 46), VTIMPK$_{2ohibu}$DIQLAR (SEQ ID NO: 47), DNIQGITK$_{2ohibu}$PAIR (SEQ ID NO: 48), K$_{2ohibu}$TVTAMDVVYALK (SEQ ID NO: 49), TVTAMDVVYALK$_{2ohibu}$R (SEQ ID NO: 50), K$_{prop}$K$_{2ohibu}$AAK$_{prop}$K$_{prop}$PAGVR (SEQ ID NO: 51), K$_{prop}$K$_{prop}$AAK$_{2ohibu}$K$_{prop}$PAGVR (SEQ ID NO: 51), K$_{prop}$AAK$_{prop}$K$_{2ohibu}$PAGVR (SEQ ID NO: 52), K$_{2ohibu}$ASGPPVSELITK$_{prop}$AVAASK$_{2ohibu}$ (SEQ ID NO: 53), K$_{prop}$ASGPPVSELITK$_{prop}$AVAASK$_{2ohibu}$ER (SEQ ID NO: 54), ALAAAGYDVEK$_{2ohibu}$NNSR (SEQ ID NO: 55), IK$_{2ohibu}$LGLK (SEQ ID NO: 56), $_{prop}$GILVQTK$_{2ohibu}$GTGASGSFK$_{prop}$ (SEQ ID NO: 57), $_{prop}$K$_{2ohibu}$AASGEAK$_{prop}$PQAK$_{prop}$ (SEQ ID NO: 58), $_{prop}$AASGEAK$_{2ohibu}$PQAK$_{prop}$ (SEQ ID NO: 59), $_{prop}$AASGEAK$_{prop}$PQAK$_{2ohibu}$K$_{prop}$ (SEQ ID NO: 60), $_{prop}$AK$_{2ohibu}$K$_{prop}$PAGAAK$_{prop}$ (SEQ ID NO: 61), $_{prop}$AK$_{prop}$K$_{prop}$PAGAAK$_{2ohibu}$K$_{prop}$PK$_{prop}$ (SEQ ID NO: 62), $_{prop}$K$_{prop}$ATGAATPK$_{2ohibu}$K$_{prop}$ (SEQ ID NO: 63), $_{prop}$K$_{prop}$AK$_{2ohibu}$K$_{prop}$PAAAAVTK$_{prop}$ (SEQ ID NO: 64), $_{prop}$K$_{prop}$PAAAAVTK$_{2ohibu}$K$_{prop}$ (SEQ ID NO: 65), K$_{prop}$VAAK$_{prop}$K$_{prop}$K$_{2ohibu}$ (SEQ ID NO: 66), GK$_{2ohibu}$QGGK$_{2ohibu}$AR (SEQ ID NO: 67), K$_{2ohibu}$GNYSER (SEQ ID NO: 68), DNK$_{2ohibu}$K$_{2ohibu}$TR (SEQ ID NO: 69), NDEELNK$_{2ohibu}$LLGR (SEQ ID NO: 70), VTIAQGGVLPNIQAVLLPK$_{2ohibu}$K (SEQ ID NO: 71), $_{prop}$PEPAK$_{2ohibu}$SAPAPK$_{prop}$ (SEQ ID NO: 72), PEPAK$_{2ohibu}$SAPAPK (SEQ ID NO: 72), $_{prop}$PEPAK$_{prop}$SAPAPK$_{prop}$K$_{2ohibu}$GSK (SEQ ID NO: 73), K$_{prop}$AISK$_{2ohibu}$AQK$_{prop}$ (SEQ ID NO: 74), AVTK$_{prop}$AQK$_{2ohibu}$K$_{prop}$DGK$_{prop}$K$_{prop}$R (SEQ ID NO:

75), AVTK$_{prop}$AQK$_{prop}$K$_{2ohibu}$DGK$_{prop}$K$_{prop}$R (SEQ ID NO: 75), K$_{2ohibu}$ESYSVYVYK (SEQ ID NO: 76), KESYSVYVYK$_{2ohibu}$VLK (SEQ ID NO: 77), QVHPDTGISSK$_{2ohibu}$AMGIMNSFVNDIFER (SEQ ID NO: 78), TK$_{2ohibu}$QTAR (SEQ ID NO: 79), K$_{2ohibu}$STGGK$_{ac}$APR (SEQ ID NO: 80), K$_{prop}$STGGK$_{2ohibu}$APR (SEQ ID NO: 80), K$_{2ohibu}$QLATK$_{ac}$AAR (SEQ ID NO: 81), KQLATK$_{2ohibu}$AAR (SEQ ID NO: 81), K$_{ac}$QLATK$_{2ohibu}$AAR (SEQ ID NO: 81), K$_{2ohibu}$SAPATGGVK$_{prop}$K$_{prop}$PHR (SEQ ID NO: 82), K$_{prop}$SAPATGGVK$_{2ohibu}$K$_{prop}$PHR (SEQ ID NO: 82), K$_{2ohibu}$LPFQR (SEQ ID NO: 83), K$_{2ohibu}$GGK$_{ac}$GLGK$_{ac}$GGAK$_{ac}$R (SEQ ID NO: 84), GK$_{ac}$GGK$_{2ohibu}$GLGK$_{ac}$GGAK$_{ac}$R (SEQ ID NO: 85), GLGK$_{2ohibu}$GGAK$_{ac}$R (SEQ ID NO: 86), GGK$_{prop}$GLGK$_{prop}$GGAK$_{2ohibu}$R (SEQ ID NO: 87), GGK$_{2ohibu}$GLGK$_{ac}$GGAK$_{ac}$R (SEQ ID NO: 87), GGK$_{ac}$GLGK$_{2ohibu}$GGAK$_{ac}$R (SEQ ID NO: 87), RGGVK$_{2ohibu}$R (SEQ ID NO: 88), GVLK$_{2ohibu}$VFLENVIR (SEQ ID NO: 89), KTVTAMDVVYALK$_{2ohibu}$R (SEQ ID NO: 90), AGSAAK$_{2ohibu}$ASQSR (SEQ ID NO: 91), K$_{2ohibu}$ETYSSYIYK (SEQ ID NO: 92), ETYSSYIYK$_{2ohibu}$VLK (SEQ ID NO: 93), IATEASK$_{2ohibu}$LAAYNK (SEQ ID NO: 94), LILPGELAK$_{2ohibu}$HAVSEGTR (SEQ ID NO: 95), FQK$_{2ohibu}$STELLIR (SEQ ID NO: 96), DSVTYTEHAK$_{2ohibu}$R (SEQ ID NO: 97), K$_{2ohibu}$TVTSLDVVYALK (SEQ ID NO: 98), TVTSLDVVYALK$_{2ohibu}$R (SEQ ID NO: 99), GMGK$_{2ohibu}$VGAK (SEQ ID NO: 100), K$_{2ohibu}$SAPATGGIK (SEQ ID NO: 101), YQK$_{2ohibu}$STDLLIR (SEQ ID NO: 102), VTIMTK$_{2ohibu}$DMQLAR (SEQ ID NO: 103), K$_{2ohibu}$APAAAAEK (SEQ ID NO: 104), K$_{ac}$APAAAAEK$_{2ohibu}$K (SEQ ID NO: 105), VLK$_{2ohibu}$QVHPDVGISK (SEQ ID NO: 106), IALESSK$_{2ohibu}$LVR (SEQ ID NO: 107), HAISEGTK$_{2ohibu}$AVTK (SEQ ID NO: 108), AVTK$_{2ohibu}$FSSSTN (SEQ ID NO: 109), TASSK$_{2ohibu}$QVSR (SEQ ID NO: 110), AGGK$_{ac}$AGK$_{2ohibu}$DSGK (SEQ ID NO: 111), AGGK$_{2ohibu}$AGK$_{ac}$DSGK (SEQ ID NO: 111) and SAPAPK$_{2ohibu}$K$_{ac}$GSK (SEQ ID NO: 112), wherein K$_{prop}$ is a propionylated lysine and K$_{ac}$ is an acetylated lysine, whereby an affinity reagent that binds specifically to the peptide is produced.

2. The method of claim 1, wherein the peptide consists of an amino acid sequence selected from the group consisting of DAVTYTEHAK$_{2ohibu}$R (SEQ ID NO: 29), ASGPPVSELITK$_{2ohibu}$AVAAS (SEQ ID NO: 30), AVAASK$_{2ohibu}$ER (SEQ ID NO: 31), SGVSLAALK$_{2ohibu}$K (SEQ ID NO: 32), K$_{2ohibu}$ALAAAGYDVEK (SEQ ID NO: 33), LGLK$_{2ohibu}$SLVSK (SEQ ID NO: 34), LGLK$_{2ohibu}$SLVSK$_{prop}$ (SEQ ID NO: 34), SLVSK$_{2ohibu}$GTLVQTK (SEQ ID NO: 35), GTLVQTK$_{2ohibu}$GTGASGSFK (SEQ ID NO: 36), NDEELNK$_{2ohibu}$LLGK (SEQ ID NO: 37), PEPSK$_{2ohibu}$SAPAPK (SEQ ID NO: 38), VLK$_{2ohibu}$QVHPDTGISSK (SEQ ID NO: 39), LAHYNK$_{2ohibu}$R (SEQ ID NO: 40), LLLPGELAK$_{2ohibu}$HAVSEGTK (SEQ ID NO: 41), HAVSEGTK$_{2ohibu}$AVTK (SEQ ID NO: 42), AVTK$_{2ohibu}$YTSSK (SEQ ID NO: 43), QLATK$_{2ohibu}$AAR (SEQ ID NO: 44), YQK$_{2ohibu}$STELLIR (SEQ ID NO: 45), EIAQDFK$_{2ohibu}$TDLR (SEQ ID NO: 46), VTIMPK$_{2ohibu}$DIQLAR (SEQ ID NO: 47), DNIQGITK$_{2ohibu}$PAIR (SEQ ID NO: 48), K$_{2ohibu}$TVTAMDVVYALK (SEQ ID NO: 49), TVTAMDVVYALK$_{2ohibu}$R (SEQ ID NO: 50), K$_{prop}$K$_{2ohibu}$AAK$_{prop}$K$_{prop}$PAGVR (SEQ ID NO: 51), K$_{prop}$K$_{prop}$AAK$_{2ohibu}$K$_{prop}$PAGVR (SEQ ID NO: 51), K$_{prop}$AAK$_{prop}$K$_{2ohibu}$PAGVR (SEQ ID NO: 52), K$_{2ohibu}$ASGPPVSELITK$_{prop}$AVAASK$_{2ohibu}$ (SEQ ID NO: 53), K$_{prop}$ASGPPVSELITK$_{prop}$AVAASK$_{2ohibu}$ER (SEQ ID NO: 54), ALAAAGYDVEK$_{2ohibu}$NNSR (SEQ ID NO: 55), IK$_{2ohibu}$LGLK (SEQ ID NO: 56), $_{prop}$GILVQTK$_{2ohibu}$GTGASGSFK$_{prop}$ (SEQ ID NO: 57), $_{prop}$K$_{2ohibu}$AASGEAK$_{prop}$PQAK$_{prop}$ (SEQ ID NO: 58), $_{prop}$AASGEAK$_{2ohibu}$PQAK$_{prop}$ (SEQ ID NO: 59), $_{prop}$AASGEAK$_{prop}$PQAK$_{2ohibu}$K$_{prop}$ (SEQ ID NO: 60), $_{prop}$AK$_{2ohibu}$K$_{prop}$PAGAAK$_{prop}$ (SEQ ID NO: 61), $_{prop}$AK$_{prop}$K$_{prop}$PAGAAK$_{2ohibu}$K$_{prop}$PK$_{prop}$ (SEQ ID NO: 62), $_{prop}$K$_{prop}$ATGAATPK$_{2ohibu}$K$_{prop}$ (SEQ ID NO: 63), $_{prop}$K$_{prop}$AK$_{2ohibu}$K$_{prop}$PAAAAVTK$_{prop}$ (SEQ ID NO: 64), $_{prop}$K$_{prop}$PAAAAVTK$_{2ohibu}$K$_{prop}$ (SEQ ID NO: 65), K$_{prop}$VAAK$_{prop}$K$_{prop}$K$_{2ohibu}$ (SEQ ID NO: 66), GK$_{2ohibu}$QGGK$_{2ohibu}$AR (SEQ ID NO: 67), K$_{2ohibu}$GNYSER (SEQ ID NO: 68), DNK$_{2ohibu}$K$_{2ohibu}$TR (SEQ ID NO: 69), NDEELNK$_{2ohibu}$LLGR (SEQ ID NO: 70), VTIAQGGVLPNIQAVLLPK$_{2ohibu}$K (SEQ ID NO: 71), $_{prop}$PEPAK$_{2ohibu}$SAPAPK$_{prop}$ (SEQ ID NO: 72), PEPAK$_{2ohibu}$SAPAPK (SEQ ID NO: 72), $_{prop}$PEPAK$_{prop}$SAPAPK$_{prop}$K$_{2ohibu}$GSK (SEQ ID NO: 73), K$_{prop}$AISK$_{2ohibu}$AQK$_{prop}$ (SEQ ID NO: 74), AVTK$_{prop}$AQK$_{2ohibu}$K$_{prop}$DGK$_{prop}$K$_{prop}$R (SEQ ID NO: 75), AVTK$_{prop}$AQK$_{prop}$K$_{2ohibu}$DGK$_{prop}$K$_{prop}$R (SEQ ID NO: 75), K$_{2ohibu}$ESYSVYVYK (SEQ ID NO: 76), KESYSVYVYK$_{2ohibu}$VLK (SEQ ID NO: 77), QVHPDTGISSK$_{2ohibu}$AMGIMNSFVNDIFER (SEQ ID NO: 78), TK$_{2ohibu}$QTAR (SEQ ID NO: 79), K$_{2ohibu}$STGGK$_{ac}$APR (SEQ ID NO: 80), K$_{prop}$STGGK$_{2ohibu}$APR (SEQ ID NO: 80), K$_{2ohibu}$QLATK$_{ac}$AAR (SEQ ID NO: 81), KQLATK$_{2ohibu}$AAR (SEQ ID NO: 81), K$_{ac}$QLATK$_{2ohibu}$AAR (SEQ ID NO: 81), K$_{2ohibu}$SAPATGGVK$_{prop}$K$_{prop}$PHR (SEQ ID NO: 82), K$_{prop}$SAPATGGVK$_{2ohibu}$K$_{prop}$PHR (SEQ ID NO: 82), K$_{2ohibu}$LPFQR (SEQ ID NO: 83), K$_{2ohibu}$GGK$_{ac}$GLGK$_{ac}$GGAK$_{ac}$R (SEQ ID NO: 84), GK$_{ac}$GGK$_{2ohibu}$GLGK$_{ac}$GGAK$_{ac}$R (SEQ ID NO: 85), GLGK$_{2ohibu}$GGAK$_{ac}$R (SEQ ID NO: 86), GGK$_{prop}$GLGK$_{prop}$GGAK$_{2ohibu}$R (SEQ ID NO: 87), GGK$_{2ohibu}$GLGK$_{ac}$GGAK$_{ac}$R (SEQ ID NO: 87), GGK$_{ac}$GLGK$_{2ohibu}$GGAK$_{ac}$R (SEQ ID NO: 87), RGGVK$_{2ohibu}$R (SEQ ID NO: 88), GVLK$_{2ohibu}$VFLENVIR (SEQ ID NO: 89), KTVTAMDVVYALK$_{2ohibu}$R (SEQ ID NO: 90), AGSAAK$_{2ohibu}$ASQSR (SEQ ID NO: 91), K$_{2ohibu}$ETYSSYIYK (SEQ ID NO: 92), ETYSSYIYK$_{2ohibu}$VLK (SEQ ID NO: 93), IATEASK$_{2ohibu}$LAAYNK (SEQ ID NO: 94), LILPGELAK$_{2ohibu}$HAVSEGTR (SEQ ID NO: 95), FQK$_{2ohibu}$STELLIR (SEQ ID NO: 96), DSVTYTEHAK$_{2ohibu}$R (SEQ ID NO: 97), K$_{2ohibu}$TVTSLDVVYALK (SEQ ID NO: 98), TVTSLDVVYALK$_{2ohibu}$R (SEQ ID NO: 99), GMGK$_{2ohibu}$VGAK (SEQ ID NO: 100), K$_{2ohibu}$SAPATGGIK (SEQ ID NO: 101), YQK$_{2ohibu}$STDLLIR (SEQ ID NO: 102), VTIMTK$_{2ohibu}$DMQLAR (SEQ ID NO: 103), K$_{2ohibu}$APAAAAEK (SEQ ID NO: 104), K$_{ac}$APAAAAEK$_{2ohibu}$K (SEQ ID NO: 105), VLK$_{2ohibu}$QVHPDVGISK (SEQ ID NO: 106), IALESSK$_{2ohibu}$LVR (SEQ ID NO: 107), HAISEGTK$_{2ohibu}$AVTK (SEQ ID NO: 108), AVTK$_{2ohibu}$FSSSTN (SEQ ID NO: 109), TASSK$_{2ohibu}$QVSR (SEQ ID NO: 110), AGGK$_{ac}$AGK$_{2ohibu}$DSGK (SEQ ID NO: 111), AGGK$_{2ohibu}$AGK$_{ac}$DSGK (SEQ ID NO: 111) and SAPAPK$_{2ohibu}$K$_{ac}$GSK (SEQ ID NO: 112), wherein K$_{prop}$ is a propionylated lysine and K$_{ac}$ is an acetylated lysine.

3. A method for producing an isolated affinity reagent, comprising screening a protein library using an isolated peptide comprising a 2-hydroxyisobutyrylated lysine, wherein the peptide comprises the amino acid sequence selected from the group consisting of DAVTYTEHAK$_{2ohibu}$R (SEQ ID NO: 29), ASGPPVSELITK$_{2ohibu}$AVAAS (SEQ ID NO: 30), AVAASK$_{2ohibu}$ER (SEQ ID NO: 31), SGVSLAALK$_{2ohibu}$K (SEQ ID NO: 32), K$_{2ohibu}$ALAAAGYDVEK (SEQ ID NO: 33), LGLK$_{2ohibu}$SLVSK (SEQ ID NO: 34), LGLK$_{2ohibu}$SLVSK$_{prop}$ (SEQ ID NO: 34), SLVSK$_{2ohibu}$GTLVQTK (SEQ ID NO: 35), GTLVQTK$_{2ohibu}$GTGASGSFK (SEQ ID NO: 36), NDEELNK$_{2ohibu}$LLGK (SEQ ID NO: 37), PEPSK$_{2ohibu}$SAPAPK (SEQ ID NO: 38), VLK$_{2ohibu}$QVHPDTGISSK (SEQ ID NO: 39), LAHYNK$_{2ohibu}$R (SEQ ID NO: 40), LLLPGELAK$_{2ohibu}$HAVSEGTK (SEQ ID NO: 41), HAVSEGTK$_{2ohibu}$AVTK (SEQ ID NO: 42), AVTK$_{2ohibu}$YTSSK (SEQ ID NO: 43), QLATK$_{2ohibu}$AAR (SEQ ID NO: 44), YQK$_{2ohibu}$STELLIR (SEQ ID NO: 45), EIAQDFK$_{2ohibu}$TDLR (SEQ ID NO: 46), VTIMPK$_{2ohibu}$DIQLAR (SEQ ID NO: 47), DNIQGITK$_{2ohibu}$PAIR (SEQ ID NO: 48), K$_{2ohibu}$TVTAMDVVYALK (SEQ ID NO: 49), TVTAMDVVYALK$_{2ohibu}$R (SEQ ID NO: 50), K$_{prop}$K$_{2ohibu}$AAK$_{prop}$K$_{prop}$PAGVR (SEQ ID NO: 51), K$_{prop}$K$_{prop}$AAK$_{2ohibu}$K$_{prop}$PAGVR (SEQ ID NO: 51), K$_{prop}$AAK$_{prop}$K$_{2ohibu}$PAGVR (SEQ ID NO: 52), K$_{2ohibu}$ASGPPVSELITK$_{prop}$AVAASK$_{2ohibu}$ (SEQ ID NO: 53), K$_{prop}$ASGPPVSELITK$_{prop}$AVAASK$_{2ohibu}$ER (SEQ ID NO: 54), ALAAAGYDVEK$_{2ohibu}$NNSR (SEQ ID NO: 55), IK$_{2ohibu}$LGLK (SEQ ID NO: 56), $_{prop}$GILVQTK$_{2ohibu}$GTGASGSFK$_{prop}$ (SEQ ID NO: 57), $_{prop}$K$_{2ohibu}$AASGEAK$_{prop}$PQAK$_{prop}$ (SEQ ID NO: 58), $_{prop}$AASGEAK$_{2ohibu}$PQAK$_{prop}$ (SEQ ID NO: 59), $_{prop}$AASGEAK$_{prop}$PQAK$_{2ohibu}$K$_{prop}$ (SEQ ID NO: 60), $_{prop}$AK$_{2ohibu}$K$_{prop}$PAGAAK$_{prop}$ (SEQ ID NO: 61), $_{prop}$AK$_{prop}$K$_{prop}$PAGAAK$_{2ohibu}$K$_{prop}$PK$_{prop}$ (SEQ ID NO: 62), $_{prop}$K$_{prop}$ATGAATPK$_{2ohibu}$K$_{prop}$ (SEQ ID NO: 63), $_{prop}$K$_{prop}$AK$_{2ohibu}$K$_{prop}$PAAAAVTK$_{prop}$ (SEQ ID NO: 64), $_{prop}$K$_{prop}$PAAAAVTK$_{2ohibu}$K$_{prop}$ (SEQ ID NO: 65), K$_{prop}$VAAK$_{prop}$K$_{prop}$K$_{2ohibu}$ (SEQ ID NO: 66), GK$_{2ohibu}$QGGK$_{2ohibu}$AR (SEQ ID NO: 67), K$_{2ohibu}$GNYSER (SEQ ID NO: 68), DNK$_{2ohibu}$K$_{2ohibu}$TR (SEQ ID NO: 69), NDEELNK$_{2ohibu}$LLGR (SEQ ID NO: 70), VTIAQGGVLPNIQAVLLPK$_{2ohibu}$K (SEQ ID NO: 71), $_{prop}$PEPAK$_{2ohibu}$SAPAPK$_{prop}$ (SEQ ID NO: 72), PEPAK$_{2ohibu}$SAPAPK (SEQ ID NO: 72), $_{prop}$PEPAK$_{prop}$SAPAPK$_{prop}$K$_{2ohibu}$GSK (SEQ ID NO: 73), K$_{prop}$AISK$_{2ohibu}$AQK$_{prop}$ (SEQ ID NO: 74), AVTK$_{prop}$AQK$_{2ohibu}$K$_{prop}$DGK$_{prop}$K$_{prop}$R (SEQ ID NO: 75), AVTK$_{prop}$AQK$_{prop}$K$_{2ohibu}$DGK$_{prop}$K$_{prop}$R (SEQ ID NO: 75), K$_{2ohibu}$ESYSVYVYK (SEQ ID NO: 76), KESYSVYVYK$_{2ohibu}$VLK (SEQ ID NO: 77), QVHPDTGISSK$_{2ohibu}$AMGIMNSFVNDIFER (SEQ ID NO: 78), TK$_{2ohibu}$QTAR (SEQ ID NO: 79), K$_{2ohibu}$STGGK$_{ac}$APR (SEQ ID NO: 80), K$_{prop}$STGGK$_{2ohibu}$APR (SEQ ID NO: 80), K$_{2ohibu}$QLATK$_{ac}$AAR (SEQ ID NO: 81), KQLATK$_{2ohibu}$AAR (SEQ ID NO: 81), K$_{ac}$QLATK$_{2ohibu}$AAR (SEQ ID NO: 81), K$_{2ohibu}$SAPATGGVK$_{prop}$K$_{prop}$PHR (SEQ ID NO: 82), K$_{prop}$SAPATGGVK$_{2ohibu}$K$_{prop}$PHR (SEQ ID NO: 82), K$_{2ohibu}$LPFQR (SEQ ID NO: 83), K$_{2ohibu}$GGK$_{ac}$GLGK$_{ac}$GGAK$_{ac}$R (SEQ ID NO: 84), GK$_{ac}$GGK$_{2ohibu}$GLGK$_{ac}$GGAK$_{ac}$R (SEQ ID NO: 85), GLGK$_{2ohibu}$GGAK$_{ac}$R (SEQ ID NO: 86), GGK$_{prop}$GLGK$_{prop}$GGAK$_{2ohibu}$R (SEQ ID NO: 87), GGK$_{2ohibu}$GLGK$_{ac}$GGAK$_{ac}$R (SEQ ID NO: 87), GGK$_{ac}$GLGK$_{2ohibu}$GGAK$_{ac}$R (SEQ ID NO: 87), RGGVK$_{2ohibu}$R (SEQ ID NO: 88), GVLK$_{2ohibu}$VFLENVIR (SEQ ID NO: 89), KTVTAMDVVYALK$_{2ohibu}$R (SEQ ID NO: 90), AGSAAK$_{2ohibu}$ASQSR (SEQ ID NO: 91), K$_{2ohibu}$ETYSSYIYK (SEQ ID NO: 92), ETYSSYIYK$_{2ohibu}$VLK (SEQ ID NO: 93), IATEASK$_{2ohibu}$LAAYNK (SEQ ID NO: 94), LILPGELAK$_{2ohibu}$HAVSEGTR (SEQ ID NO: 95), FQK$_{2ohibu}$STELLIR (SEQ ID NO: 96), DSVTYTEHAK$_{2ohibu}$R (SEQ ID NO: 97), K$_{2ohibu}$TVTSLDVVYALK (SEQ ID NO: 98), TVTSLDVVYALK$_{2ohibu}$R (SEQ ID NO: 99), GMGK$_{2ohibu}$VGAK (SEQ ID NO: 100), K$_{2ohibu}$SAPATGGIK (SEQ ID NO: 101), YQK$_{2ohibu}$STDLLIR (SEQ ID NO: 102), VTIMTK$_{2ohibu}$DMQLAR (SEQ ID NO: 103), K$_{2ohibu}$APAAAAEK (SEQ ID NO: 104), K$_{ac}$APAAAAEK$_{2ohibu}$K (SEQ ID NO: 105), VLK$_{2ohibu}$QVHPDVGISK (SEQ ID NO: 106), IALESSK$_{2ohibu}$LVR (SEQ ID NO: 107), HAISEGTK$_{2ohibu}$AVTK (SEQ ID NO: 108), AVTK$_{2ohibu}$FSSSTN (SEQ ID NO: 109), TASSK$_{2ohibu}$OVSR (SEQ ID NO: 110), AGGK$_{ac}$AGK$_{2ohibu}$DSGK (SEQ ID NO: 111), AGGK$_{2ohibu}$AGK$_{ac}$DSGK (SEQ ID NO: 111) and SAPAPK$_{2ohibu}$K$_{ac}$GSK (SEQ ID NO: 112), wherein K$_{prop}$ is a propionylated lysine and K$_{ac}$ is an acetylated lysine, whereby an affinity reagent that binds specifically to the peptide is produced.

4. The method of claim 3, wherein the peptide consists of an amino acid sequence selected from the group consisting of DAVTYTEHAK$_{2ohibu}$R (SEQ ID NO: 29), ASGPPVSELITK$_{2ohibu}$AVAAS (SEQ ID NO: 30), AVAASK$_{2ohibu}$ER (SEQ ID NO: 31), SGVSLAALK$_{2ohibu}$K (SEQ ID NO: 32), K$_{2ohibu}$ALAAAGYDVEK (SEQ ID NO: 33), LGLK$_{2ohibu}$SLVSK (SEQ ID NO: 34), LGLK$_{2ohibu}$SLVSK$_{prop}$ (SEQ ID NO: 34), SLVSK$_{2ohibu}$GTLVQTK (SEQ ID NO: 35), GTLVQTK$_{2ohibu}$GTGASGSFK (SEQ ID NO: 36), NDEELNK$_{2ohibu}$LLGK (SEQ ID NO: 37), PEPSK$_{2ohibu}$SAPAPK (SEQ ID NO: 38), VLK$_{2ohibu}$QVHPDTGISSK (SEQ ID NO: 39), LAHYNK$_{2ohibu}$R (SEQ ID NO: 40), LLLPGELAK$_{2ohibu}$HAVSEGTK (SEQ ID NO: 41), HAVSEGTK$_{2ohibu}$AVTK (SEQ ID NO: 42), AVTK$_{2ohibu}$YTSSK (SEQ ID NO: 43), QLATK$_{2ohibu}$AAR (SEQ ID NO: 44), YQK$_{2ohibu}$STELLIR (SEQ ID NO: 45), EIAQDFK$_{2ohibu}$TDLR (SEQ ID NO: 46), VTIMPK$_{2ohibu}$DIQLAR (SEQ ID NO: 47), DNIQGITK$_{2ohibu}$PAIR (SEQ ID NO: 48), K$_{2ohibu}$TVTAMDVVYALK (SEQ ID NO: 49), TVTAMDVVYALK$_{2ohibu}$R (SEQ ID NO: 50), K$_{prop}$K$_{2ohibu}$AAK$_{prop}$K$_{prop}$PAGVR (SEQ ID NO: 51), K$_{prop}$K$_{prop}$AAK$_{2ohibu}$K$_{prop}$PAGVR (SEQ ID NO: 51), K$_{prop}$AAK$_{prop}$K$_{2ohibu}$PAGVR (SEQ ID NO: 52), K$_{2ohibu}$ASGPPVSELITK$_{prop}$AVAASK$_{2ohibu}$ (SEQ ID NO: 53), K$_{prop}$ASGPPVSELITK$_{prop}$AVAASK$_{2ohibu}$ER (SEQ ID NO: 54), ALAAAGYDVEK$_{2ohibu}$NNSR (SEQ ID NO: 55), IK$_{2ohibu}$LGLK (SEQ ID NO: 56), $_{prop}$GILVQTK$_{2ohibu}$GTGASGSFK$_{prop}$ (SEQ ID NO: 57), $_{prop}$K$_{2ohibu}$AASGEAK$_{prop}$PQAK$_{prop}$ (SEQ ID NO: 58), $_{prop}$AASGEAK$_{2ohibu}$PQAK$_{prop}$ (SEQ ID NO: 59), $_{prop}$AASGEAK$_{prop}$PQAK$_{2ohibu}$K$_{prop}$ (SEQ ID NO: 60), $_{prop}$AK$_{2ohibu}$K$_{prop}$PAGAAK$_{prop}$ (SEQ ID NO: 61), $_{prop}$AK$_{prop}$K$_{prop}$PAGAAK$_{2ohibu}$K$_{prop}$PK$_{prop}$ (SEQ ID NO: 62), $_{prop}$K$_{prop}$ATGAATPK$_{2ohibu}$K$_{prop}$ (SEQ ID NO: 63), $_{prop}$K$_{prop}$AK$_{2ohibu}$K$_{prop}$PAAAAVTK$_{prop}$ (SEQ ID NO: 64), $_{prop}$K$_{prop}$PAAAAVTK$_{2ohibu}$K$_{prop}$ (SEQ ID NO: 65), K$_{prop}$VAAK$_{prop}$K$_{prop}$K$_{2ohibu}$ (SEQ ID NO: 66), GK$_{2ohibu}$QGGK$_{2ohibu}$AR (SEQ ID NO: 67), K$_{2ohibu}$GNYSER (SEQ ID NO: 68), DNK$_{2ohibu}$K$_{2ohibu}$TR (SEQ ID NO: 69), NDEELNK$_{2ohibu}$LLGR (SEQ ID NO: 70), VTIAQGGVLPNIQAVLLPK$_{2ohibu}$K (SEQ ID NO: 71), $_{prop}$PEPAK$_{2ohibu}$SAPAPK$_{prop}$ (SEQ ID NO: 72), PEPAK$_{2ohibu}$SAPAPK (SEQ ID NO: 72), $_{prop}$PEPAK$_{prop}$SAPAPK$_{prop}$K$_{2ohibu}$GSK (SEQ ID NO: 73), K$_{prop}$AISK$_{2ohibu}$AQK$_{prop}$ (SEQ ID NO: 74), AVTK$_{prop}$AQK$_{2ohibu}$K$_{prop}$DGK$_{prop}$K$_{prop}$R (SEQ ID NO: 75), AVTK$_{prop}$AQK$_{prop}$K$_{2ohibu}$DGK$_{prop}$K$_{prop}$R (SEQ ID NO: 75), K$_{2ohibu}$ESYSVYVYK (SEQ ID NO: 76), KESYSVYVYK$_{2ohibu}$VLK (SEQ ID NO: 77), QVHPDTGISSK$_{2ohibu}$AMGIMNSFVNDIFER (SEQ ID NO: 78), TK$_{2ohibu}$QTAR (SEQ ID NO: 79), K$_{2ohibu}$STGGK$_{ac}$APR (SEQ ID NO: 80), K$_{prop}$STGGK$_{2ohibu}$APR (SEQ ID NO: 80), K$_{2ohibu}$QLATK$_{ac}$AAR (SEQ ID NO: 81), KQLATK$_{2ohibu}$AAR (SEQ ID NO: 81), K$_{ac}$QLATK$_{2ohibu}$AAR (SEQ ID NO: 81), K$_{2ohibu}$SAPATGGVK$_{prop}$K$_{prop}$PHR (SEQ ID NO: 82), K$_{prop}$SAPATGGVK$_{2ohibu}$K$_{prop}$PHR (SEQ ID NO: 82), K$_{2ohibu}$ LPFQR (SEQ ID NO: 83), K$_{2ohibu}$GGK$_{ac}$GLGK$_{ac}$GGAK$_{ac}$R (SEQ ID NO: 84), GK$_{ac}$GGK$_{2ohibu}$GLGK$_{ac}$GGAK$_{ac}$R (SEQ ID NO: 85), GLGK$_{2ohibu}$GGAK$_{ac}$R (SEQ ID NO: 86), GGK$_{prop}$GLGK$_{prop}$GGAK$_{2ohibu}$R (SEQ ID NO: 87), GGK$_{2ohibu}$GLGK$_{ac}$GGAK$_{ac}$R (SEQ ID NO: 87), GGK$_{ac}$GLGK$_{2ohibu}$GGAK$_{ac}$R (SEQ ID NO: 87), RGGVK$_{2ohibu}$R (SEQ ID NO: 88), GVLK$_{2ohibu}$VFLENVIR (SEQ ID NO: 89), KTVTAMDVVYALK$_{2ohibu}$R (SEQ ID NO: 90), AGSAAK$_{2ohibu}$ASQSR (SEQ ID NO: 91), K$_{2ohibu}$ETYSSYIYK (SEQ ID NO: 92), ETYSSYIYK$_{2ohibu}$VLK (SEQ ID NO: 93), IATEASK$_{2ohibu}$LAAYNK (SEQ ID NO: 94), LILPGELAK$_{2ohibu}$HAVSEGTR (SEQ ID NO: 95), FQK$_{2ohibu}$STELLIR (SEQ ID NO: 96), DSVTYTEHAK$_{2ohibu}$R (SEQ ID NO: 97), K$_{2ohibu}$TVTSLDVVYALK (SEQ ID NO: 98), TVTSLDVVYALK$_{2ohibu}$R (SEQ ID NO: 99), GMGK$_{2ohibu}$VGAK (SEQ ID NO: 100), K$_{2ohibu}$SAPATGGIK (SEQ ID NO: 101), YQK$_{2ohibu}$STDLLIR (SEQ ID NO: 102), VTIMTK$_{2ohibu}$DMQLAR (SEQ ID NO: 103), K$_{2ohibu}$APAAAAEK (SEQ ID NO: 104), K$_{ac}$APAAAAEK$_{2ohibu}$K (SEQ ID NO: 105), VLK$_{2ohibu}$QVHPDVGISK (SEQ ID NO: 106), IALESSK$_{2ohibu}$LVR (SEQ ID NO: 107), HAISEGTK$_{2ohibu}$AVTK (SEQ ID NO: 108), AVTK$_{2ohibu}$FSSSTN (SEQ ID NO: 109), TASSK$_{2ohibu}$QVSR (SEQ ID NO: 110), AGGK$_{ac}$AGK$_{2ohibu}$DSGK (SEQ ID NO: 111), AGGK$_{2ohibu}$AGK$_{ac}$DSGK (SEQ ID NO: 111) and SAPAPK$_{2ohibu}$K$_{ac}$GSK (SEQ ID NO: 112), wherein K$_{prop}$ is a propionylated lysine and K$_{ac}$ is an acetylated lysine.

5. The method of claim 1, further comprising:
   (a) contacting a protein or a fragment thereof with the isolated affinity reagent, whereby the isolated affinity reagent and the protein or a fragment thereof forms a binding complex, and
   (b) detecting the binding complex.

6. A method of claim 3, further comprising:
   (a) contacting the protein or a fragment thereof with the isolated affinity reagent, whereby the isolated affinity reagent and the protein or a fragment thereof forms a binding complex, and
   (b) detecting the binding complex.

\* \* \* \* \*

SEQUENCE LISTING

<160> NUMBER OF SEQ ID NOS: 112

<210> SEQ ID NO 1
<211> LENGTH: 213
<212> TYPE: PRT
<213> ORGANISM: Homo sapiens

<400> SEQUENCE: 1

Met Ser Glu Thr Ala Pro Ala Ala Pro Ala Ala Pro Pro Ala Glu
1               5                   10                  15

Lys Ala Pro Val Lys Lys Ala Ala Lys Lys Ala Gly Gly Thr Pro
                20                  25                  30

Arg Lys Ala Ser Gly Pro Pro Val Ser Glu Leu Ile Thr Lys Ala Val
            35                  40                  45

Ala Ala Ser Lys Glu Arg Ser Gly Val Ser Leu Ala Ala Leu Lys Lys
        50                  55                  60

Ala Leu Ala Ala Ala Gly Tyr Asp Val Glu Lys Asn Asn Ser Arg Ile
65                  70                  75                  80

Lys Leu Gly Leu Lys Ser Leu Val Ser Lys Gly Thr Leu Val Gln Thr
                85                  90                  95

Lys Gly Thr Gly Ala Ser Gly Ser Phe Lys Leu Asn Lys Lys Ala Ala
            100                 105                 110

Ser Gly Glu Ala Lys Pro Lys Val Lys Lys Ala Gly Gly Thr Lys Pro
        115                 120                 125

Lys Lys Pro Val Gly Ala Ala Lys Lys Pro Lys Lys Ala Ala Gly Gly
    130                 135                 140

Ala Thr Pro Lys Lys Ser Ala Lys Lys Thr Pro Lys Lys Ala Lys Lys
145                 150                 155                 160

Pro Ala Ala Ala Thr Val Thr Lys Lys Val Ala Lys Ser Pro Lys Lys
                165                 170                 175

Ala Lys Val Ala Lys Pro Lys Ala Ala Lys Ser Ala Ala Lys Ala
            180                 185                 190

Val Lys Pro Lys Ala Ala Lys Pro Lys Val Val Lys Pro Lys Lys Ala
        195                 200                 205

Ala Pro Lys Lys Lys
    210

<210> SEQ ID NO 2
<211> LENGTH: 130
<212> TYPE: PRT
<213> ORGANISM: Homo sapiens

<400> SEQUENCE: 2

Met Ser Gly Arg Gly Lys Gln Gly Gly Lys Ala Arg Ala Lys Ala Lys
1               5                   10                  15

Thr Arg Ser Ser Arg Ala Gly Leu Gln Phe Pro Val Gly Arg Val His
                20                  25                  30

Arg Leu Leu Arg Lys Gly Asn Tyr Ala Glu Arg Val Gly Ala Gly Ala
            35                  40                  45

Pro Val Tyr Leu Ala Ala Val Leu Glu Tyr Leu Thr Ala Glu Ile Leu
        50                  55                  60

Glu Leu Ala Gly Asn Ala Ala Arg Asp Asn Lys Lys Thr Arg Ile Ile
65                  70                  75                  80

Pro Arg His Leu Gln Leu Ala Ile Arg Asn Asp Glu Glu Leu Asn Lys
                85                  90                  95

Leu Leu Gly Lys Val Thr Ile Ala Gln Gly Gly Val Leu Pro Asn Ile

```
                         100                 105                 110

Gln Ala Val Leu Leu Pro Lys Lys Thr Glu Ser His His Lys Ala Lys
            115                 120                 125

Gly Lys
    130

<210> SEQ ID NO 3
<211> LENGTH: 126
<212> TYPE: PRT
<213> ORGANISM: Homo sapiens

<400> SEQUENCE: 3

Met Pro Glu Pro Ser Lys Ser Ala Pro Ala Pro Lys Lys Gly Ser Lys
1               5                   10                  15

Lys Ala Ile Thr Lys Ala Gln Lys Lys Asp Gly Lys Lys Arg Lys Arg
            20                  25                  30

Ser Arg Lys Glu Ser Tyr Ser Ile Tyr Val Tyr Lys Val Leu Lys Gln
        35                  40                  45

Val His Pro Asp Thr Gly Ile Ser Ser Lys Ala Met Gly Ile Met Asn
    50                  55                  60

Ser Phe Val Asn Asp Ile Phe Glu Arg Ile Ala Gly Glu Ala Ser Arg
65                  70                  75                  80

Leu Ala His Tyr Asn Lys Arg Ser Thr Ile Thr Ser Arg Glu Ile Gln
                85                  90                  95

Thr Ala Val Arg Leu Leu Leu Pro Gly Glu Leu Ala Lys His Ala Val
            100                 105                 110

Ser Glu Gly Thr Lys Ala Val Thr Lys Tyr Thr Ser Ser Lys
        115                 120                 125

<210> SEQ ID NO 4
<211> LENGTH: 136
<212> TYPE: PRT
<213> ORGANISM: Homo sapiens

<400> SEQUENCE: 4

Met Ala Arg Thr Lys Gln Thr Ala Arg Lys Ser Thr Gly Gly Lys Ala
1               5                   10                  15

Pro Arg Lys Gln Leu Ala Thr Lys Ala Ala Arg Lys Ser Ala Pro Ser
            20                  25                  30

Thr Gly Gly Val Lys Lys Pro His Arg Tyr Arg Pro Gly Thr Val Ala
        35                  40                  45

Leu Arg Glu Ile Arg Arg Tyr Gln Lys Ser Thr Glu Leu Leu Ile Arg
    50                  55                  60

Lys Leu Pro Phe Gln Arg Leu Val Arg Glu Ile Ala Gln Asp Phe Lys
65                  70                  75                  80

Thr Asp Leu Arg Phe Gln Ser Ala Ala Ile Gly Ala Leu Gln Glu Ala
                85                  90                  95

Ser Glu Ala Tyr Leu Val Gly Leu Phe Glu Asp Thr Asn Leu Cys Ala
            100                 105                 110

Ile His Ala Lys Arg Val Thr Ile Met Pro Lys Asp Ile Gln Leu Ala
        115                 120                 125

Arg Arg Ile Arg Gly Glu Arg Ala
    130                 135

<210> SEQ ID NO 5
<211> LENGTH: 103
<212> TYPE: PRT
```

<213> ORGANISM: Homo sapiens

<400> SEQUENCE: 5

Met Ser Gly Arg Gly Lys Gly Gly Lys Gly Leu Gly Lys Gly Gly Ala
1               5                   10                  15

Lys Arg His Arg Lys Val Leu Arg Asp Asn Ile Gln Gly Ile Thr Lys
            20                  25                  30

Pro Ala Ile Arg Arg Leu Ala Arg Arg Gly Gly Val Lys Arg Ile Ser
        35                  40                  45

Gly Leu Ile Tyr Glu Glu Thr Arg Gly Val Leu Lys Val Phe Leu Glu
    50                  55                  60

Asn Val Ile Arg Asp Ala Val Thr Tyr Thr Glu His Ala Lys Arg Lys
65                  70                  75                  80

Thr Val Thr Ala Met Asp Val Val Tyr Ala Leu Lys Arg Gln Gly Arg
                85                  90                  95

Thr Leu Tyr Gly Phe Gly Gly
            100

<210> SEQ ID NO 6
<211> LENGTH: 212
<212> TYPE: PRT
<213> ORGANISM: Mus musculus

<400> SEQUENCE: 6

Met Ser Glu Ala Ala Pro Ala Ala Pro Ala Ala Ala Pro Pro Ala Glu
1               5                   10                  15

Lys Ala Pro Ala Lys Lys Lys Ala Ala Lys Lys Pro Ala Gly Val Arg
            20                  25                  30

Arg Lys Ala Ser Gly Pro Pro Val Ser Glu Leu Ile Thr Lys Ala Val
        35                  40                  45

Ala Ala Ser Lys Glu Arg Ser Gly Val Ser Leu Ala Ala Leu Lys Lys
    50                  55                  60

Ala Leu Ala Ala Ala Gly Tyr Asp Val Glu Lys Asn Asn Ser Arg Ile
65                  70                  75                  80

Lys Leu Gly Leu Lys Ser Leu Val Ser Lys Gly Ile Leu Val Gln Thr
                85                  90                  95

Lys Gly Thr Gly Ala Ser Gly Ser Phe Lys Leu Asn Lys Lys Ala Ala
            100                 105                 110

Ser Gly Glu Ala Lys Pro Gln Ala Lys Lys Ala Gly Ala Ala Lys Ala
        115                 120                 125

Lys Lys Pro Ala Gly Ala Ala Lys Lys Pro Lys Lys Ala Thr Gly Ala
    130                 135                 140

Ala Thr Pro Lys Lys Ala Ala Lys Lys Thr Pro Lys Lys Ala Lys Lys
145                 150                 155                 160

Pro Ala Ala Ala Val Thr Lys Lys Val Lys Ser Pro Lys Lys
                165                 170                 175

Ala Lys Val Thr Lys Pro Lys Lys Val Lys Ser Ala Ser Lys Ala Val
            180                 185                 190

Lys Pro Lys Ala Ala Lys Pro Lys Val Ala Lys Ala Lys Lys Val Ala
        195                 200                 205

Ala Lys Lys Lys
    210

<210> SEQ ID NO 7
<211> LENGTH: 130
<212> TYPE: PRT

<213> ORGANISM: Mus musculus

<400> SEQUENCE: 7

Met Ser Gly Arg Gly Lys Gln Gly Gly Lys Ala Arg Ala Lys Ala Lys
1               5                   10                  15

Thr Arg Ser Ser Arg Ala Gly Leu Gln Phe Pro Val Gly Arg Val His
            20                  25                  30

Arg Leu Leu Arg Lys Gly Asn Tyr Ser Glu Arg Val Gly Ala Gly Ala
        35                  40                  45

Pro Val Tyr Leu Ala Ala Val Leu Glu Tyr Leu Thr Ala Glu Ile Leu
    50                  55                  60

Glu Leu Ala Gly Asn Ala Ala Arg Asp Asn Lys Lys Thr Arg Ile Ile
65                  70                  75                  80

Pro Arg His Leu Gln Leu Ala Ile Arg Asn Asp Glu Glu Leu Asn Lys
                85                  90                  95

Leu Leu Gly Arg Val Thr Ile Ala Gln Gly Gly Val Leu Pro Asn Ile
            100                 105                 110

Gln Ala Val Leu Leu Pro Lys Lys Thr Glu Ser His His Lys Ala Lys
        115                 120                 125

Gly Lys
    130

<210> SEQ ID NO 8
<211> LENGTH: 126
<212> TYPE: PRT
<213> ORGANISM: Mus musculus

<400> SEQUENCE: 8

Met Pro Glu Pro Ala Lys Ser Ala Pro Ala Pro Lys Lys Gly Ser Lys
1               5                   10                  15

Lys Ala Val Thr Lys Ala Gln Lys Lys Asp Gly Lys Lys Arg Lys Arg
            20                  25                  30

Ser Arg Lys Glu Ser Tyr Ser Val Tyr Val Tyr Lys Val Leu Lys Gln
        35                  40                  45

Val His Pro Asp Thr Gly Ile Ser Ser Lys Ala Met Gly Ile Met Asn
    50                  55                  60

Ser Phe Val Asn Asp Ile Phe Glu Arg Ile Ala Ser Glu Ala Ser Arg
65                  70                  75                  80

Leu Ala His Tyr Asn Lys Arg Ser Thr Ile Thr Ser Arg Glu Ile Gln
                85                  90                  95

Thr Ala Val Arg Leu Leu Leu Pro Gly Glu Leu Ala Lys His Ala Val
            100                 105                 110

Ser Glu Gly Thr Lys Ala Val Thr Lys Tyr Thr Ser Ser Lys
        115                 120                 125

<210> SEQ ID NO 9
<211> LENGTH: 136
<212> TYPE: PRT
<213> ORGANISM: Mus musculus

<400> SEQUENCE: 9

Met Ala Arg Thr Lys Gln Thr Ala Arg Lys Ser Thr Gly Gly Lys Ala
1               5                   10                  15

Pro Arg Lys Gln Leu Ala Thr Lys Ala Ala Arg Lys Ser Ala Pro Ser
            20                  25                  30

Thr Gly Gly Val Lys Lys Pro His Arg Tyr Arg Pro Gly Thr Val Ala
        35                  40                  45

```
Leu Arg Glu Ile Arg Arg Tyr Gln Lys Ser Thr Glu Leu Leu Ile Arg
        50                  55                  60

Lys Leu Pro Phe Gln Arg Leu Val Arg Glu Ile Ala Gln Asp Phe Lys
 65                  70                  75                  80

Thr Asp Leu Arg Phe Gln Ser Ala Ala Ile Gly Ala Leu Gln Glu Ala
                85                  90                  95

Ser Glu Ala Tyr Leu Val Gly Leu Phe Glu Asp Thr Asn Leu Cys Ala
            100                 105                 110

Ile His Ala Lys Arg Val Thr Ile Met Pro Lys Asp Ile Gln Leu Ala
        115                 120                 125

Arg Arg Ile Arg Gly Glu Arg Ala
        130                 135

<210> SEQ ID NO 10
<211> LENGTH: 103
<212> TYPE: PRT
<213> ORGANISM: Mus musculus

<400> SEQUENCE: 10

Met Ser Gly Arg Gly Lys Gly Gly Lys Gly Leu Gly Lys Gly Gly Ala
 1               5                  10                  15

Lys Arg His Arg Lys Val Leu Arg Asp Asn Ile Gln Gly Ile Thr Lys
            20                  25                  30

Pro Ala Ile Arg Arg Leu Ala Arg Arg Gly Gly Val Lys Arg Ile Ser
        35                  40                  45

Gly Leu Ile Tyr Glu Glu Thr Arg Gly Val Leu Lys Val Phe Leu Glu
    50                  55                  60

Asn Val Ile Arg Asp Ala Val Thr Tyr Thr Glu His Ala Lys Arg Lys
 65                  70                  75                  80

Thr Val Thr Ala Met Asp Val Val Tyr Ala Leu Lys Arg Gln Gly Arg
                85                  90                  95

Thr Leu Tyr Gly Phe Gly Gly
            100

<210> SEQ ID NO 11
<211> LENGTH: 132
<212> TYPE: PRT
<213> ORGANISM: Saccharomyces cerevisiae

<400> SEQUENCE: 11

Met Ser Gly Gly Lys Gly Gly Lys Ala Gly Ser Ala Ala Lys Ala Ser
 1               5                  10                  15

Gln Ser Arg Ser Ala Lys Ala Gly Leu Thr Phe Pro Val Gly Arg Val
            20                  25                  30

His Arg Leu Leu Arg Arg Gly Asn Tyr Ala Gln Arg Ile Gly Ser Gly
        35                  40                  45

Ala Pro Val Tyr Leu Thr Ala Val Leu Glu Tyr Leu Ala Ala Glu Ile
    50                  55                  60

Leu Glu Leu Ala Gly Asn Ala Ala Arg Asp Asn Lys Lys Thr Arg Ile
 65                  70                  75                  80

Ile Pro Arg His Leu Gln Leu Ala Ile Arg Asn Asp Asp Glu Leu Asn
                85                  90                  95

Lys Leu Leu Gly Asn Val Thr Ile Ala Gln Gly Gly Val Leu Pro Asn
            100                 105                 110

Ile His Gln Asn Leu Leu Pro Lys Lys Ser Ala Lys Ala Thr Lys Ala
        115                 120                 125
```

Ser Gln Glu Leu
    130

<210> SEQ ID NO 12
<211> LENGTH: 131
<212> TYPE: PRT
<213> ORGANISM: Saccharomyces cerevisiae

<400> SEQUENCE: 12

Met Ser Ser Ala Ala Glu Lys Lys Pro Ala Ser Lys Ala Pro Ala Glu
1               5                   10                  15

Lys Lys Pro Ala Ala Lys Lys Thr Ser Thr Ser Val Asp Gly Lys Lys
            20                  25                  30

Arg Ser Lys Val Arg Lys Glu Thr Tyr Ser Ser Tyr Ile Tyr Lys Val
        35                  40                  45

Leu Lys Gln Thr His Pro Asp Thr Gly Ile Ser Gln Lys Ser Met Ser
    50                  55                  60

Ile Leu Asn Ser Phe Val Asn Asp Ile Phe Glu Arg Ile Ala Thr Glu
65                  70                  75                  80

Ala Ser Lys Leu Ala Ala Tyr Asn Lys Lys Ser Thr Ile Ser Ala Arg
                85                  90                  95

Glu Ile Gln Thr Ala Val Arg Leu Ile Leu Pro Gly Glu Leu Ala Lys
            100                 105                 110

His Ala Val Ser Glu Gly Thr Arg Ala Val Thr Lys Tyr Ser Ser Ser
        115                 120                 125

Thr Gln Ala
    130

<210> SEQ ID NO 13
<211> LENGTH: 136
<212> TYPE: PRT
<213> ORGANISM: Saccharomyces cerevisiae

<400> SEQUENCE: 13

Met Ala Arg Thr Lys Gln Thr Ala Arg Lys Ser Thr Gly Gly Lys Ala
1               5                   10                  15

Pro Arg Lys Gln Leu Ala Ser Lys Ala Ala Arg Lys Ser Ala Pro Ser
            20                  25                  30

Thr Gly Gly Val Lys Lys Pro His Arg Tyr Lys Pro Gly Thr Val Ala
        35                  40                  45

Leu Arg Glu Ile Arg Arg Phe Gln Lys Ser Thr Glu Leu Leu Ile Arg
    50                  55                  60

Lys Leu Pro Phe Gln Arg Leu Val Arg Glu Ile Ala Gln Asp Phe Lys
65                  70                  75                  80

Thr Asp Leu Arg Phe Gln Ser Ser Ala Ile Gly Ala Leu Gln Glu Ser
                85                  90                  95

Val Glu Ala Tyr Leu Val Ser Leu Phe Glu Asp Thr Asn Leu Ala Ala
            100                 105                 110

Ile His Ala Lys Arg Val Thr Ile Gln Lys Lys Asp Ile Lys Leu Ala
        115                 120                 125

Arg Arg Leu Arg Gly Glu Arg Ser
    130                 135

<210> SEQ ID NO 14
<211> LENGTH: 103
<212> TYPE: PRT
<213> ORGANISM: Saccharomyces cerevisiae

<400> SEQUENCE: 14

Met Ser Gly Arg Gly Lys Gly Lys Gly Leu Gly Lys Gly Gly Ala
1               5                   10                  15

Lys Arg His Arg Lys Ile Leu Arg Asp Asn Ile Gln Gly Ile Thr Lys
            20                  25                  30

Pro Ala Ile Arg Arg Leu Ala Arg Arg Gly Gly Val Lys Arg Ile Ser
        35                  40                  45

Gly Leu Ile Tyr Glu Glu Val Arg Ala Val Leu Lys Ser Phe Leu Glu
    50                  55                  60

Ser Val Ile Arg Asp Ser Val Thr Tyr Thr Glu His Ala Lys Arg Lys
65                  70                  75                  80

Thr Val Thr Ser Leu Asp Val Val Tyr Ala Leu Lys Arg Gln Gly Arg
                85                  90                  95

Thr Leu Tyr Gly Phe Gly Gly
            100

<210> SEQ ID NO 15
<211> LENGTH: 133
<212> TYPE: PRT
<213> ORGANISM: Tetrahymena thermophila

<400> SEQUENCE: 15

Met Ser Thr Thr Gly Lys Gly Gly Lys Ala Lys Gly Lys Thr Ala Ser
1               5                   10                  15

Ser Lys Gln Val Ser Arg Ser Ala Arg Ala Gly Leu Gln Phe Pro Val
            20                  25                  30

Gly Arg Ile Ser Arg Phe Leu Lys Asn Gly Arg Tyr Ser Glu Arg Ile
        35                  40                  45

Gly Thr Gly Ala Pro Val Tyr Leu Ala Ala Val Leu Glu Tyr Leu Ala
    50                  55                  60

Ala Glu Val Leu Glu Leu Ala Gly Asn Ala Ala Lys Asp Asn Lys Lys
65                  70                  75                  80

Thr Arg Ile Val Pro Arg His Ile Leu Leu Ala Ile Arg Asn Asp Glu
                85                  90                  95

Glu Leu Asn Lys Leu Met Ala Asn Thr Thr Ile Ala Asp Gly Gly Val
            100                 105                 110

Leu Pro Asn Ile Asn Pro Met Leu Leu Pro Ser Lys Thr Lys Lys Ser
        115                 120                 125

Thr Glu Pro Glu His
    130

<210> SEQ ID NO 16
<211> LENGTH: 120
<212> TYPE: PRT
<213> ORGANISM: Tetrahymena thermophila

<400> SEQUENCE: 16

Met Ala Pro Lys Lys Ala Pro Ala Ala Ala Glu Lys Lys Val Lys
1               5                   10                  15

Lys Ala Pro Thr Thr Glu Lys Lys Asn Lys Lys Lys Arg Ser Glu Thr
            20                  25                  30

Phe Ala Ile Tyr Ile Phe Lys Val Leu Lys Gln Val His Pro Asp Val
        35                  40                  45

Gly Ile Ser Lys Lys Ala Met Asn Ile Met Asn Ser Phe Ile Asn Asp
    50                  55                  60

-continued

```
Ser Phe Glu Arg Ile Ala Leu Glu Ser Ser Lys Leu Val Arg Phe Asn
 65                  70                  75                  80

Lys Arg Arg Thr Leu Ser Ser Arg Glu Val Gln Thr Ala Val Lys Leu
                 85                  90                  95

Leu Leu Pro Gly Glu Leu Ala Arg His Ala Ile Ser Glu Gly Thr Lys
            100                 105                 110

Ala Val Thr Lys Phe Ser Ser Ser
        115                 120

<210> SEQ ID NO 17
<211> LENGTH: 136
<212> TYPE: PRT
<213> ORGANISM: Tetrahymena thermophila

<400> SEQUENCE: 17

Met Ala Arg Thr Lys Gln Thr Ala Arg Lys Ser Thr Gly Ala Lys Ala
  1               5                  10                  15

Pro Arg Lys Gln Leu Ala Ser Lys Ala Ala Arg Lys Ser Ala Pro Ala
                 20                  25                  30

Thr Gly Gly Ile Lys Lys Pro His Arg Phe Arg Pro Gly Thr Val Ala
             35                  40                  45

Leu Arg Glu Ile Arg Lys Tyr Gln Lys Ser Thr Asp Leu Leu Ile Arg
 50                  55                  60

Lys Leu Pro Phe Gln Arg Leu Val Arg Asp Ile Ala His Glu Phe Lys
 65                  70                  75                  80

Ala Glu Leu Arg Phe Gln Ser Ser Ala Val Leu Ala Leu Gln Glu Ala
                 85                  90                  95

Ala Glu Ala Tyr Leu Val Gly Leu Phe Glu Asp Thr Asn Leu Cys Ala
            100                 105                 110

Ile His Ala Arg Arg Val Thr Ile Met Thr Lys Asp Met Gln Leu Ala
        115                 120                 125

Arg Arg Ile Arg Gly Glu Arg Phe
130                 135

<210> SEQ ID NO 18
<211> LENGTH: 103
<212> TYPE: PRT
<213> ORGANISM: Tetrahymena thermophila

<400> SEQUENCE: 18

Met Ala Gly Gly Lys Gly Gly Lys Gly Met Gly Lys Val Gly Ala Lys
  1               5                  10                  15

Arg His Ser Arg Lys Ser Asn Lys Ala Ser Ile Glu Gly Ile Thr Lys
                 20                  25                  30

Pro Ala Ile Arg Arg Leu Ala Arg Gly Gly Val Lys Arg Ile Ser
             35                  40                  45

Ser Phe Ile Tyr Asp Asp Ser Arg Gln Val Leu Lys Ser Phe Leu Glu
 50                  55                  60

Asn Val Val Arg Asp Ala Val Thr Tyr Thr Glu His Ala Arg Arg Lys
 65                  70                  75                  80

Thr Val Thr Ala Met Asp Val Val Tyr Ala Leu Lys Arg Gln Gly Arg
                 85                  90                  95

Thr Leu Tyr Gly Phe Gly Gly
            100

<210> SEQ ID NO 19
<211> LENGTH: 256
```

```
<212> TYPE: PRT
<213> ORGANISM: Drosophila melanogaster

<400> SEQUENCE: 19

Met Ser Asp Ser Ala Val Ala Thr Ser Ala Ser Pro Val Ala Pro
1               5                   10                  15

Pro Ala Thr Val Glu Lys Lys Val Val Gln Lys Lys Ala Ser Gly Ser
                20                  25                  30

Ala Gly Thr Lys Ala Lys Lys Ala Ser Ala Thr Pro Ser His Pro Pro
            35                  40                  45

Thr Gln Gln Met Val Asp Ala Ser Ile Lys Asn Leu Lys Glu Arg Gly
        50                  55                  60

Gly Ser Ser Leu Leu Ala Ile Lys Lys Tyr Ile Thr Ala Thr Tyr Lys
65                  70                  75                  80

Cys Asp Ala Gln Lys Leu Ala Pro Phe Ile Lys Tyr Leu Lys Ser
                85                  90                  95

Ala Val Val Asn Gly Lys Leu Ile Gln Thr Lys Gly Lys Gly Ala Ser
                100                 105                 110

Gly Ser Phe Lys Leu Ser Ala Ser Ala Lys Lys Glu Lys Asp Pro Lys
            115                 120                 125

Ala Lys Ser Lys Val Leu Ser Ala Glu Lys Lys Val Gln Ser Lys Lys
        130                 135                 140

Val Ala Ser Lys Lys Ile Gly Val Ser Ser Lys Lys Thr Ala Val Gly
145                 150                 155                 160

Ala Ala Asp Lys Lys Pro Lys Ala Lys Lys Ala Val Ala Thr Lys Lys
                165                 170                 175

Thr Ala Glu Asn Lys Lys Thr Glu Lys Ala Lys Ala Lys Asp Ala Lys
            180                 185                 190

Lys Thr Gly Ile Ile Lys Ser Lys Pro Ala Ala Thr Lys Ala Lys Val
        195                 200                 205

Thr Ala Ala Lys Pro Lys Ala Val Val Ala Lys Ala Ser Lys Ala Lys
    210                 215                 220

Pro Ala Val Ser Ala Lys Pro Lys Thr Val Lys Lys Ala Ser Val
225                 230                 235                 240

Ser Ala Thr Ala Lys Lys Pro Lys Ala Lys Thr Thr Ala Ala Lys Lys
                245                 250                 255

<210> SEQ ID NO 20
<211> LENGTH: 141
<212> TYPE: PRT
<213> ORGANISM: Drosophila melanogaster

<400> SEQUENCE: 20

Met Ala Gly Gly Lys Ala Gly Lys Asp Ser Gly Lys Ala Lys Ala Lys
1               5                   10                  15

Ala Val Ser Arg Ser Ala Arg Ala Gly Leu Gln Phe Pro Val Gly Arg
                20                  25                  30

Ile His Arg His Leu Lys Ser Arg Thr Thr Ser His Gly Arg Val Gly
            35                  40                  45

Ala Thr Ala Ala Val Tyr Ser Ala Ala Ile Leu Glu Tyr Leu Thr Ala
        50                  55                  60

Glu Val Leu Glu Leu Ala Gly Asn Ala Ser Lys Asp Leu Lys Val Lys
65                  70                  75                  80

Arg Ile Thr Pro Arg His Leu Gln Leu Ala Ile Arg Gly Asp Glu Glu
                85                  90                  95
```

Leu Asp Ser Leu Ile Lys Ala Thr Ile Ala Gly Gly Gly Val Ile Pro
            100                 105                 110

His Ile His Lys Ser Leu Ile Gly Lys Lys Glu Glu Thr Val Gln Asp
        115                 120                 125

Pro Gln Arg Lys Gly Asn Val Ile Leu Ser Gln Ala Tyr
    130                 135                 140

<210> SEQ ID NO 21
<211> LENGTH: 123
<212> TYPE: PRT
<213> ORGANISM: Drosophila melanogaster

<400> SEQUENCE: 21

Met Pro Pro Lys Thr Ser Gly Lys Ala Ala Lys Lys Ala Gly Lys Ala
1               5                   10                  15

Gln Lys Asn Ile Thr Lys Thr Asp Lys Lys Lys Arg Lys Arg Lys
            20                  25                  30

Glu Ser Tyr Ala Ile Tyr Ile Tyr Lys Val Leu Lys Gln Val His Pro
        35                  40                  45

Asp Thr Gly Ile Ser Ser Lys Ala Met Ser Ile Met Asn Ser Phe Val
    50                  55                  60

Asn Asp Ile Phe Glu Arg Ile Ala Ala Glu Ala Ser Arg Leu Ala His
65                  70                  75                  80

Tyr Asn Lys Arg Ser Thr Ile Thr Ser Arg Glu Ile Gln Thr Ala Val
                85                  90                  95

Arg Leu Leu Leu Pro Gly Glu Leu Ala Lys His Ala Val Ser Glu Gly
            100                 105                 110

Thr Lys Ala Val Thr Lys Tyr Thr Ser Ser Lys
        115                 120

<210> SEQ ID NO 22
<211> LENGTH: 136
<212> TYPE: PRT
<213> ORGANISM: Drosophila melanogaster

<400> SEQUENCE: 22

Met Ala Arg Thr Lys Gln Thr Ala Arg Lys Ser Thr Gly Gly Lys Ala
1               5                   10                  15

Pro Arg Lys Gln Leu Ala Thr Lys Ala Ala Arg Lys Ser Ala Pro Ala
            20                  25                  30

Thr Gly Gly Val Lys Lys Pro His Arg Tyr Arg Pro Gly Thr Val Ala
        35                  40                  45

Leu Arg Glu Ile Arg Arg Tyr Gln Lys Ser Thr Glu Leu Leu Ile Arg
    50                  55                  60

Lys Leu Pro Phe Gln Arg Leu Val Arg Glu Ile Ala Gln Asp Phe Lys
65                  70                  75                  80

Thr Asp Leu Arg Phe Gln Ser Ser Ala Val Met Ala Leu Gln Glu Ala
                85                  90                  95

Ser Glu Ala Tyr Leu Val Gly Leu Phe Glu Asp Thr Asn Leu Cys Ala
            100                 105                 110

Ile His Ala Lys Arg Val Thr Ile Met Pro Lys Asp Ile Gln Leu Ala
        115                 120                 125

Arg Arg Ile Arg Gly Glu Arg Ala
    130                 135

<210> SEQ ID NO 23
<211> LENGTH: 103

<212> TYPE: PRT
<213> ORGANISM: Drosophila melanogaster

<400> SEQUENCE: 23

```
Met Thr Gly Arg Gly Lys Gly Lys Gly Leu Gly Lys Gly Gly Ala
1               5                   10                  15
Lys Arg His Arg Lys Val Leu Arg Asp Asn Ile Gln Gly Ile Thr Lys
                20                  25                  30
Pro Ala Ile Arg Arg Leu Ala Arg Arg Gly Gly Val Lys Arg Ile Ser
            35                  40                  45
Gly Leu Ile Tyr Glu Glu Thr Arg Gly Val Leu Lys Val Phe Leu Glu
    50                  55                  60
Asn Val Ile Arg Asp Ala Val Thr Tyr Thr Glu His Ala Lys Arg Lys
65                  70                  75                  80
Thr Val Thr Ala Met Asp Val Val Tyr Ala Leu Lys Arg Gln Gly Arg
                85                  90                  95
Thr Leu Tyr Gly Phe Gly Gly
            100
```

<210> SEQ ID NO 24
<211> LENGTH: 208
<212> TYPE: PRT
<213> ORGANISM: Caenorhabditis elegans

<400> SEQUENCE: 24

```
Met Ser Asp Ser Ala Val Val Ala Ala Val Glu Pro Lys Val Pro
1               5                   10                  15
Lys Ala Lys Ala Ala Lys Ala Ala Lys Pro Thr Lys Val Ala Lys Ala
                20                  25                  30
Lys Ala Pro Val Ala His Pro Pro Tyr Ile Asn Met Ile Lys Glu Ala
            35                  40                  45
Ile Lys Gln Leu Lys Asp Arg Lys Gly Ala Ser Lys Gln Ala Ile Leu
    50                  55                  60
Lys Phe Ile Ser Gln Asn Tyr Lys Leu Gly Asp Asn Val Ile Gln Ile
65                  70                  75                  80
Asn Ala His Leu Arg Gln Ala Leu Lys Arg Gly Val Thr Ser Lys Ala
                85                  90                  95
Leu Val Gln Ala Ala Gly Ser Gly Ala Asn Gly Arg Phe Arg Val Pro
            100                 105                 110
Glu Lys Ala Ala Ala Lys Lys Pro Ala Ala Lys Lys Pro Ala
    115                 120                 125
Ala Ala Lys Lys Pro Ala Ala Ala Lys Lys Ala Thr Gly Glu Lys Lys
    130                 135                 140
Ala Lys Lys Pro Ala Ala Ala Lys Pro Lys Lys Ala Ala Thr Gly Asp
145                 150                 155                 160
Lys Lys Val Lys Lys Ala Lys Ser Pro Lys Lys Val Ala Lys Pro Ala
                165                 170                 175
Ala Lys Lys Val Ala Lys Ser Pro Lys Lys Ala Ala Pro Lys Lys
            180                 185                 190
Ile Ala Lys Pro Ala Ala Lys Lys Ala Ala Lys Pro Ala Ala Lys Ala
    195                 200                 205
```

<210> SEQ ID NO 25
<211> LENGTH: 127
<212> TYPE: PRT
<213> ORGANISM: Caenorhabditis elegans -continued

```
<400> SEQUENCE: 25

Met Ser Gly Arg Gly Lys Gly Lys Ala Lys Thr Gly Gly Lys Ala
1               5                   10                  15

Lys Ser Arg Ser Ser Arg Ala Gly Leu Gln Phe Pro Val Gly Arg Leu
            20                  25                  30

His Arg Ile Leu Arg Lys Gly Asn Tyr Ala Gln Arg Val Gly Ala Gly
        35                  40                  45

Ala Pro Val Tyr Leu Ala Ala Val Leu Glu Tyr Leu Ala Ala Glu Val
    50                  55                  60

Leu Glu Leu Ala Gly Asn Ala Ala Arg Asp Asn Lys Lys Thr Arg Ile
65                  70                  75                  80

Ala Pro Arg His Leu Gln Leu Ala Val Arg Asn Asp Glu Glu Leu Asn
                85                  90                  95

Lys Leu Leu Ala Gly Val Thr Ile Ala Gln Gly Gly Val Leu Pro Asn
            100                 105                 110

Ile Gln Ala Val Leu Leu Pro Lys Lys Thr Gly Gly Asp Lys Glu
        115                 120                 125

<210> SEQ ID NO 26
<211> LENGTH: 122
<212> TYPE: PRT
<213> ORGANISM: Caenorhabditis elegans

<400> SEQUENCE: 26

Met Pro Pro Lys Pro Ser Ala Lys Gly Ala Lys Lys Ala Ala Lys Thr
1               5                   10                  15

Val Thr Lys Pro Lys Asp Gly Lys Lys Arg Arg His Ala Arg Lys Glu
            20                  25                  30

Ser Tyr Ser Val Tyr Ile Tyr Arg Val Leu Lys Gln Val His Pro Asp
        35                  40                  45

Thr Gly Val Ser Ser Lys Ala Met Ser Ile Met Asn Ser Phe Val Asn
    50                  55                  60

Asp Val Phe Glu Arg Ile Ala Ala Glu Ala Ser Arg Leu Ala His Tyr
65                  70                  75                  80

Asn Lys Arg Ser Thr Ile Ser Ser Arg Glu Ile Gln Thr Ala Val Arg
                85                  90                  95

Leu Ile Leu Pro Gly Glu Leu Ala Lys His Ala Val Ser Glu Gly Thr
            100                 105                 110

Lys Ala Val Thr Lys Tyr Thr Ser Ser Lys
        115                 120

<210> SEQ ID NO 27
<211> LENGTH: 136
<212> TYPE: PRT
<213> ORGANISM: Caenorhabditis elegans

<400> SEQUENCE: 27

Met Ala Arg Thr Lys Gln Thr Arg Lys Ser Thr Gly Gly Lys Ala
1               5                   10                  15

Pro Arg Lys Gln Leu Ala Thr Lys Ala Ala Arg Lys Ser Ala Pro Ala
            20                  25                  30

Ser Gly Gly Val Lys Lys Pro His Arg Tyr Arg Pro Gly Thr Val Ala
        35                  40                  45

Leu Arg Glu Ile Arg Arg Tyr Gln Lys Ser Thr Glu Leu Leu Ile Arg
    50                  55                  60

Arg Ala Pro Phe Gln Arg Leu Val Arg Glu Ile Ala Gln Asp Phe Lys
```

```
              65                  70                  75                  80
Thr Asp Leu Arg Phe Gln Ser Ser Ala Val Met Ala Leu Gln Glu Ala
                    85                  90                  95

Cys Glu Ala Tyr Leu Val Gly Leu Phe Glu Asp Thr Asn Leu Cys Ala
                100                 105                 110

Ile His Ala Lys Arg Val Thr Ile Met Pro Lys Asp Ile Gln Leu Ala
                115                 120                 125

Arg Arg Ile Arg Gly Glu Arg Ala
    130                 135

<210> SEQ ID NO 28
<211> LENGTH: 103
<212> TYPE: PRT
<213> ORGANISM: Caenorhabditis elegans

<400> SEQUENCE: 28

Met Ser Gly Arg Gly Lys Gly Gly Lys Gly Leu Gly Lys Gly Gly Ala
1               5                   10                  15

Lys Arg His Arg Lys Val Leu Arg Asp Asn Ile Gln Gly Ile Thr Lys
                20                  25                  30

Pro Ala Ile Arg Arg Leu Ala Arg Arg Gly Gly Val Lys Arg Ile Ser
                35                  40                  45

Gly Leu Ile Tyr Glu Glu Thr Arg Gly Val Leu Lys Val Phe Leu Glu
            50                  55                  60

Asn Val Ile Arg Asp Ala Val Thr Tyr Cys Glu His Ala Lys Arg Lys
65                  70                  75                  80

Thr Val Thr Ala Met Asp Val Val Tyr Ala Leu Lys Arg Gln Gly Arg
                85                  90                  95

Thr Leu Tyr Gly Phe Gly Gly
            100

<210> SEQ ID NO 29
<211> LENGTH: 11
<212> TYPE: PRT
<213> ORGANISM: Artificial Sequence
<220> FEATURE:
<223> OTHER INFORMATION: Synthetic

<400> SEQUENCE: 29

Asp Ala Val Thr Tyr Thr Glu His Ala Lys Arg
1               5                   10

<210> SEQ ID NO 30
<211> LENGTH: 18
<212> TYPE: PRT
<213> ORGANISM: Artificial Sequence
<220> FEATURE:
<223> OTHER INFORMATION: Synthetic

<400> SEQUENCE: 30

Ala Ser Gly Pro Pro Val Ser Glu Leu Ile Thr Lys Ala Val Ala Ala
1               5                   10                  15

Ser Lys

<210> SEQ ID NO 31
<211> LENGTH: 8
<212> TYPE: PRT
<213> ORGANISM: Artificial Sequence
<220> FEATURE:
<223> OTHER INFORMATION: Synthetic
```

```
<400> SEQUENCE: 31

Ala Val Ala Ala Ser Lys Glu Arg
1               5

<210> SEQ ID NO 32
<211> LENGTH: 10
<212> TYPE: PRT
<213> ORGANISM: Artificial Sequence
<220> FEATURE:
<223> OTHER INFORMATION: Synthetic

<400> SEQUENCE: 32

Ser Gly Val Ser Leu Ala Ala Leu Lys Lys
1               5                   10

<210> SEQ ID NO 33
<211> LENGTH: 12
<212> TYPE: PRT
<213> ORGANISM: Artificial Sequence
<220> FEATURE:
<223> OTHER INFORMATION: Synthetic

<400> SEQUENCE: 33

Lys Ala Leu Ala Ala Ala Gly Tyr Asp Val Glu Lys
1               5                   10

<210> SEQ ID NO 34
<211> LENGTH: 9
<212> TYPE: PRT
<213> ORGANISM: Artificial Sequence
<220> FEATURE:
<223> OTHER INFORMATION: Synthetic

<400> SEQUENCE: 34

Leu Gly Leu Lys Ser Leu Val Ser Lys
1               5

<210> SEQ ID NO 35
<211> LENGTH: 12
<212> TYPE: PRT
<213> ORGANISM: Artificial Sequence
<220> FEATURE:
<223> OTHER INFORMATION: Synthetic

<400> SEQUENCE: 35

Ser Leu Val Ser Lys Gly Thr Leu Val Gln Thr Lys
1               5                   10

<210> SEQ ID NO 36
<211> LENGTH: 16
<212> TYPE: PRT
<213> ORGANISM: Artificial Sequence
<220> FEATURE:
<223> OTHER INFORMATION: Synthetic

<400> SEQUENCE: 36

Gly Thr Leu Val Gln Thr Lys Gly Thr Gly Ala Ser Gly Ser Phe Lys
1               5                   10                  15

<210> SEQ ID NO 37
<211> LENGTH: 11
<212> TYPE: PRT
<213> ORGANISM: Artificial Sequence
<220> FEATURE:
<223> OTHER INFORMATION: Synthetic

<400> SEQUENCE: 37
```

```
Asn Asp Glu Glu Leu Asn Lys Leu Leu Gly Lys
1               5                   10

<210> SEQ ID NO 38
<211> LENGTH: 11
<212> TYPE: PRT
<213> ORGANISM: Artificial Sequence
<220> FEATURE:
<223> OTHER INFORMATION: Synthetic

<400> SEQUENCE: 38

Pro Glu Pro Ser Lys Ser Ala Pro Ala Pro Lys
1               5                   10

<210> SEQ ID NO 39
<211> LENGTH: 14
<212> TYPE: PRT
<213> ORGANISM: Artificial Sequence
<220> FEATURE:
<223> OTHER INFORMATION: Synthetic

<400> SEQUENCE: 39

Val Leu Lys Gln Val His Pro Asp Thr Gly Ile Ser Ser Lys
1               5                   10

<210> SEQ ID NO 40
<211> LENGTH: 7
<212> TYPE: PRT
<213> ORGANISM: Artificial Sequence
<220> FEATURE:
<223> OTHER INFORMATION: Synthetic

<400> SEQUENCE: 40

Leu Ala His Tyr Asn Lys Arg
1               5

<210> SEQ ID NO 41
<211> LENGTH: 17
<212> TYPE: PRT
<213> ORGANISM: Artificial Sequence
<220> FEATURE:
<223> OTHER INFORMATION: Synthetic

<400> SEQUENCE: 41

Leu Leu Leu Pro Gly Glu Leu Ala Lys His Ala Val Ser Glu Gly Thr
1               5                   10                  15

Lys

<210> SEQ ID NO 42
<211> LENGTH: 12
<212> TYPE: PRT
<213> ORGANISM: Artificial Sequence
<220> FEATURE:
<223> OTHER INFORMATION: Synthetic

<400> SEQUENCE: 42

His Ala Val Ser Glu Gly Thr Lys Ala Val Thr Lys
1               5                   10

<210> SEQ ID NO 43
<211> LENGTH: 9
<212> TYPE: PRT
<213> ORGANISM: Artificial Sequence
<220> FEATURE:
<223> OTHER INFORMATION: Synthetic
```

```
<400> SEQUENCE: 43

Ala Val Thr Lys Tyr Thr Ser Ser Lys
1               5

<210> SEQ ID NO 44
<211> LENGTH: 8
<212> TYPE: PRT
<213> ORGANISM: Artificial Sequence
<220> FEATURE:
<223> OTHER INFORMATION: Synthetic

<400> SEQUENCE: 44

Gln Leu Ala Thr Lys Ala Ala Arg
1               5

<210> SEQ ID NO 45
<211> LENGTH: 10
<212> TYPE: PRT
<213> ORGANISM: Artificial Sequence
<220> FEATURE:
<223> OTHER INFORMATION: Synthetic

<400> SEQUENCE: 45

Tyr Gln Lys Ser Thr Glu Leu Leu Ile Arg
1               5                   10

<210> SEQ ID NO 46
<211> LENGTH: 11
<212> TYPE: PRT
<213> ORGANISM: Artificial Sequence
<220> FEATURE:
<223> OTHER INFORMATION: Synthetic

<400> SEQUENCE: 46

Glu Ile Ala Gln Asp Phe Lys Thr Asp Leu Arg
1               5                   10

<210> SEQ ID NO 47
<211> LENGTH: 12
<212> TYPE: PRT
<213> ORGANISM: Artificial Sequence
<220> FEATURE:
<223> OTHER INFORMATION: Synthetic

<400> SEQUENCE: 47

Val Thr Ile Met Pro Lys Asp Ile Gln Leu Ala Arg
1               5                   10

<210> SEQ ID NO 48
<211> LENGTH: 12
<212> TYPE: PRT
<213> ORGANISM: Artificial Sequence
<220> FEATURE:
<223> OTHER INFORMATION: Synthetic

<400> SEQUENCE: 48

Asp Asn Ile Gln Gly Ile Thr Lys Pro Ala Ile Arg
1               5                   10

<210> SEQ ID NO 49
<211> LENGTH: 13
<212> TYPE: PRT
<213> ORGANISM: Artificial Sequence
<220> FEATURE:
<223> OTHER INFORMATION: Synthetic

<400> SEQUENCE: 49
```

```
Lys Thr Val Thr Ala Met Asp Val Val Tyr Ala Leu Lys
1               5                   10
```

<210> SEQ ID NO 50
<211> LENGTH: 13
<212> TYPE: PRT
<213> ORGANISM: Artificial Sequence
<220> FEATURE:
<223> OTHER INFORMATION: Synthetic

<400> SEQUENCE: 50

```
Thr Val Thr Ala Met Asp Val Val Tyr Ala Leu Lys Arg
1               5                   10
```

<210> SEQ ID NO 51
<211> LENGTH: 11
<212> TYPE: PRT
<213> ORGANISM: Artificial Sequence
<220> FEATURE:
<223> OTHER INFORMATION: Synthetic

<400> SEQUENCE: 51

```
Lys Lys Ala Ala Lys Lys Pro Ala Gly Val Arg
1               5                   10
```

<210> SEQ ID NO 52
<211> LENGTH: 10
<212> TYPE: PRT
<213> ORGANISM: Artificial Sequence
<220> FEATURE:
<223> OTHER INFORMATION: Synthetic

<400> SEQUENCE: 52

```
Lys Ala Ala Lys Lys Pro Ala Gly Val Arg
1               5                   10
```

<210> SEQ ID NO 53
<211> LENGTH: 19
<212> TYPE: PRT
<213> ORGANISM: Artificial Sequence
<220> FEATURE:
<223> OTHER INFORMATION: Synthetic

<400> SEQUENCE: 53

```
Lys Ala Ser Gly Pro Pro Val Ser Glu Leu Ile Thr Lys Ala Val Ala
1               5                   10                  15

Ala Ser Lys
```

<210> SEQ ID NO 54
<211> LENGTH: 21
<212> TYPE: PRT
<213> ORGANISM: Artificial Sequence
<220> FEATURE:
<223> OTHER INFORMATION: Synthetic

<400> SEQUENCE: 54

```
Lys Ala Ser Gly Pro Pro Val Ser Glu Leu Ile Thr Lys Ala Val Ala
1               5                   10                  15

Ala Ser Lys Glu Arg
            20
```

<210> SEQ ID NO 55
<211> LENGTH: 15
<212> TYPE: PRT
<213> ORGANISM: Artificial Sequence

```
<220> FEATURE:
<223> OTHER INFORMATION: Synthetic

<400> SEQUENCE: 55

Ala Leu Ala Ala Ala Gly Tyr Asp Val Glu Lys Asn Asn Ser Arg
1               5                   10                  15

<210> SEQ ID NO 56
<211> LENGTH: 6
<212> TYPE: PRT
<213> ORGANISM: Artificial Sequence
<220> FEATURE:
<223> OTHER INFORMATION: Synthetic

<400> SEQUENCE: 56

Ile Lys Leu Gly Leu Lys
1               5

<210> SEQ ID NO 57
<211> LENGTH: 16
<212> TYPE: PRT
<213> ORGANISM: Artificial Sequence
<220> FEATURE:
<223> OTHER INFORMATION: Synthetic

<400> SEQUENCE: 57

Gly Ile Leu Val Gln Thr Lys Gly Thr Gly Ala Ser Gly Ser Phe Lys
1               5                   10                  15

<210> SEQ ID NO 58
<211> LENGTH: 12
<212> TYPE: PRT
<213> ORGANISM: Artificial Sequence
<220> FEATURE:
<223> OTHER INFORMATION: Synthetic

<400> SEQUENCE: 58

Lys Ala Ala Ser Gly Glu Ala Lys Pro Gln Ala Lys
1               5                   10

<210> SEQ ID NO 59
<211> LENGTH: 11
<212> TYPE: PRT
<213> ORGANISM: Artificial Sequence
<220> FEATURE:
<223> OTHER INFORMATION: Synthetic

<400> SEQUENCE: 59

Ala Ala Ser Gly Glu Ala Lys Pro Gln Ala Lys
1               5                   10

<210> SEQ ID NO 60
<211> LENGTH: 12
<212> TYPE: PRT
<213> ORGANISM: Artificial Sequence
<220> FEATURE:
<223> OTHER INFORMATION: Synthetic

<400> SEQUENCE: 60

Ala Ala Ser Gly Glu Ala Lys Pro Gln Ala Lys Lys
1               5                   10

<210> SEQ ID NO 61
<211> LENGTH: 9
<212> TYPE: PRT
<213> ORGANISM: Artificial Sequence
<220> FEATURE:
```

```
<223> OTHER INFORMATION: Synthetic

<400> SEQUENCE: 61

Ala Lys Lys Pro Ala Gly Ala Ala Lys
1               5

<210> SEQ ID NO 62
<211> LENGTH: 12
<212> TYPE: PRT
<213> ORGANISM: Artificial Sequence
<220> FEATURE:
<223> OTHER INFORMATION: Synthetic

<400> SEQUENCE: 62

Ala Lys Lys Pro Ala Gly Ala Ala Lys Lys Pro Lys
1               5                   10

<210> SEQ ID NO 63
<211> LENGTH: 10
<212> TYPE: PRT
<213> ORGANISM: Artificial Sequence
<220> FEATURE:
<223> OTHER INFORMATION: Synthetic

<400> SEQUENCE: 63

Lys Ala Thr Gly Ala Ala Thr Pro Lys Lys
1               5                   10

<210> SEQ ID NO 64
<211> LENGTH: 12
<212> TYPE: PRT
<213> ORGANISM: Artificial Sequence
<220> FEATURE:
<223> OTHER INFORMATION: Synthetic

<400> SEQUENCE: 64

Lys Ala Lys Lys Pro Ala Ala Ala Ala Val Thr Lys
1               5                   10

<210> SEQ ID NO 65
<211> LENGTH: 10
<212> TYPE: PRT
<213> ORGANISM: Artificial Sequence
<220> FEATURE:
<223> OTHER INFORMATION: Synthetic

<400> SEQUENCE: 65

Lys Pro Ala Ala Ala Ala Val Thr Lys Lys
1               5                   10

<210> SEQ ID NO 66
<211> LENGTH: 7
<212> TYPE: PRT
<213> ORGANISM: Artificial Sequence
<220> FEATURE:
<223> OTHER INFORMATION: Synthetic

<400> SEQUENCE: 66

Lys Val Ala Ala Lys Lys Lys
1               5

<210> SEQ ID NO 67
<211> LENGTH: 8
<212> TYPE: PRT
<213> ORGANISM: Artificial Sequence
<220> FEATURE:
<223> OTHER INFORMATION: Synthetic
```

```
<400> SEQUENCE: 67

Gly Lys Gln Gly Gly Lys Ala Arg
1               5

<210> SEQ ID NO 68
<211> LENGTH: 7
<212> TYPE: PRT
<213> ORGANISM: Artificial Sequence
<220> FEATURE:
<223> OTHER INFORMATION: Synthetic

<400> SEQUENCE: 68

Lys Gly Asn Tyr Ser Glu Arg
1               5

<210> SEQ ID NO 69
<211> LENGTH: 6
<212> TYPE: PRT
<213> ORGANISM: Artificial Sequence
<220> FEATURE:
<223> OTHER INFORMATION: Synthetic

<400> SEQUENCE: 69

Asp Asn Lys Lys Thr Arg
1               5

<210> SEQ ID NO 70
<211> LENGTH: 11
<212> TYPE: PRT
<213> ORGANISM: Artificial Sequence
<220> FEATURE:
<223> OTHER INFORMATION: Synthetic

<400> SEQUENCE: 70

Asn Asp Glu Glu Leu Asn Lys Leu Leu Gly Arg
1               5                   10

<210> SEQ ID NO 71
<211> LENGTH: 20
<212> TYPE: PRT
<213> ORGANISM: Artificial Sequence
<220> FEATURE:
<223> OTHER INFORMATION: Synthetic

<400> SEQUENCE: 71

Val Thr Ile Ala Gln Gly Gly Val Leu Pro Asn Ile Gln Ala Val Leu
1               5                   10                  15

Leu Pro Lys Lys
            20

<210> SEQ ID NO 72
<211> LENGTH: 11
<212> TYPE: PRT
<213> ORGANISM: Artificial Sequence
<220> FEATURE:
<223> OTHER INFORMATION: Synthetic

<400> SEQUENCE: 72

Pro Glu Pro Ala Lys Ser Ala Pro Ala Pro Lys
1               5                   10

<210> SEQ ID NO 73
<211> LENGTH: 15
<212> TYPE: PRT
<213> ORGANISM: Artificial Sequence
```

```
<220> FEATURE:
<223> OTHER INFORMATION: Synthetic

<400> SEQUENCE: 73

Pro Glu Pro Ala Lys Ser Ala Pro Ala Pro Lys Lys Gly Ser Lys
1               5                   10                  15

<210> SEQ ID NO 74
<211> LENGTH: 8
<212> TYPE: PRT
<213> ORGANISM: Artificial Sequence
<220> FEATURE:
<223> OTHER INFORMATION: Synthetic

<400> SEQUENCE: 74

Lys Ala Ile Ser Lys Ala Gln Lys
1               5

<210> SEQ ID NO 75
<211> LENGTH: 13
<212> TYPE: PRT
<213> ORGANISM: Artificial Sequence
<220> FEATURE:
<223> OTHER INFORMATION: Synthetic

<400> SEQUENCE: 75

Ala Val Thr Lys Ala Gln Lys Lys Asp Gly Lys Lys Arg
1               5                   10

<210> SEQ ID NO 76
<211> LENGTH: 10
<212> TYPE: PRT
<213> ORGANISM: Artificial Sequence
<220> FEATURE:
<223> OTHER INFORMATION: Synthetic

<400> SEQUENCE: 76

Lys Glu Ser Tyr Ser Val Tyr Val Tyr Lys
1               5                   10

<210> SEQ ID NO 77
<211> LENGTH: 13
<212> TYPE: PRT
<213> ORGANISM: Artificial Sequence
<220> FEATURE:
<223> OTHER INFORMATION: Synthetic

<400> SEQUENCE: 77

Lys Glu Ser Tyr Ser Val Tyr Val Tyr Lys Val Leu Lys
1               5                   10

<210> SEQ ID NO 78
<211> LENGTH: 26
<212> TYPE: PRT
<213> ORGANISM: Artificial Sequence
<220> FEATURE:
<223> OTHER INFORMATION: Synthetic

<400> SEQUENCE: 78

Gln Val His Pro Asp Thr Gly Ile Ser Ser Lys Ala Met Gly Ile Met
1               5                   10                  15

Asn Ser Phe Val Asn Asp Ile Phe Glu Arg
            20                  25

<210> SEQ ID NO 79
<211> LENGTH: 6
```

<212> TYPE: PRT
<213> ORGANISM: Artificial Sequence
<220> FEATURE:
<223> OTHER INFORMATION: Synthetic

<400> SEQUENCE: 79

Thr Lys Gln Thr Ala Arg
1               5

<210> SEQ ID NO 80
<211> LENGTH: 9
<212> TYPE: PRT
<213> ORGANISM: Artificial Sequence
<220> FEATURE:
<223> OTHER INFORMATION: Synthetic

<400> SEQUENCE: 80

Lys Ser Thr Gly Gly Lys Ala Pro Arg
1               5

<210> SEQ ID NO 81
<211> LENGTH: 9
<212> TYPE: PRT
<213> ORGANISM: Artificial Sequence
<220> FEATURE:
<223> OTHER INFORMATION: Synthetic

<400> SEQUENCE: 81

Lys Gln Leu Ala Thr Lys Ala Ala Arg
1               5

<210> SEQ ID NO 82
<211> LENGTH: 14
<212> TYPE: PRT
<213> ORGANISM: Artificial Sequence
<220> FEATURE:
<223> OTHER INFORMATION: Synthetic

<400> SEQUENCE: 82

Lys Ser Ala Pro Ala Thr Gly Gly Val Lys Lys Pro His Arg
1               5                   10

<210> SEQ ID NO 83
<211> LENGTH: 13
<212> TYPE: PRT
<213> ORGANISM: Artificial Sequence
<220> FEATURE:
<223> OTHER INFORMATION: Synthetic

<400> SEQUENCE: 83

Lys Gly Gly Lys Gly Leu Gly Lys Gly Gly Ala Lys Arg
1               5                   10

<210> SEQ ID NO 84
<211> LENGTH: 13
<212> TYPE: PRT
<213> ORGANISM: Artificial Sequence
<220> FEATURE:
<223> OTHER INFORMATION: Synthetic

<400> SEQUENCE: 84

Lys Gly Gly Lys Gly Leu Gly Lys Gly Gly Ala Lys Arg
1               5                   10

<210> SEQ ID NO 85
<211> LENGTH: 14
<212> TYPE: PRT

```
<213> ORGANISM: Artificial Sequence
<220> FEATURE:
<223> OTHER INFORMATION: Synthetic

<400> SEQUENCE: 85

Gly Lys Gly Gly Lys Gly Leu Gly Lys Gly Gly Ala Lys Arg
1               5                   10

<210> SEQ ID NO 86
<211> LENGTH: 9
<212> TYPE: PRT
<213> ORGANISM: Artificial Sequence
<220> FEATURE:
<223> OTHER INFORMATION: Synthetic

<400> SEQUENCE: 86

Gly Leu Gly Lys Gly Gly Ala Lys Arg
1               5

<210> SEQ ID NO 87
<211> LENGTH: 12
<212> TYPE: PRT
<213> ORGANISM: Artificial Sequence
<220> FEATURE:
<223> OTHER INFORMATION: Synthetic

<400> SEQUENCE: 87

Gly Gly Lys Gly Leu Gly Lys Gly Gly Ala Lys Arg
1               5                   10

<210> SEQ ID NO 88
<211> LENGTH: 6
<212> TYPE: PRT
<213> ORGANISM: Artificial Sequence
<220> FEATURE:
<223> OTHER INFORMATION: Synthetic

<400> SEQUENCE: 88

Arg Gly Gly Val Lys Arg
1               5

<210> SEQ ID NO 89
<211> LENGTH: 12
<212> TYPE: PRT
<213> ORGANISM: Artificial Sequence
<220> FEATURE:
<223> OTHER INFORMATION: Synthetic

<400> SEQUENCE: 89

Gly Val Leu Lys Val Phe Leu Glu Asn Val Ile Arg
1               5                   10

<210> SEQ ID NO 90
<211> LENGTH: 14
<212> TYPE: PRT
<213> ORGANISM: Artificial Sequence
<220> FEATURE:
<223> OTHER INFORMATION: Synthetic

<400> SEQUENCE: 90

Lys Thr Val Thr Ala Met Asp Val Val Tyr Ala Leu Lys Arg
1               5                   10

<210> SEQ ID NO 91
<211> LENGTH: 11
<212> TYPE: PRT
<213> ORGANISM: Artificial Sequence
```

```
<220> FEATURE:
<223> OTHER INFORMATION: Synthetic

<400> SEQUENCE: 91

Ala Gly Ser Ala Ala Lys Ala Ser Gln Ser Arg
1               5                   10

<210> SEQ ID NO 92
<211> LENGTH: 10
<212> TYPE: PRT
<213> ORGANISM: Artificial Sequence
<220> FEATURE:
<223> OTHER INFORMATION: Synthetic

<400> SEQUENCE: 92

Lys Glu Thr Tyr Ser Ser Tyr Ile Tyr Lys
1               5                   10

<210> SEQ ID NO 93
<211> LENGTH: 12
<212> TYPE: PRT
<213> ORGANISM: Artificial Sequence
<220> FEATURE:
<223> OTHER INFORMATION: Synthetic

<400> SEQUENCE: 93

Glu Thr Tyr Ser Ser Tyr Ile Tyr Lys Val Leu Lys
1               5                   10

<210> SEQ ID NO 94
<211> LENGTH: 13
<212> TYPE: PRT
<213> ORGANISM: Artificial Sequence
<220> FEATURE:
<223> OTHER INFORMATION: Synthetic

<400> SEQUENCE: 94

Ile Ala Thr Glu Ala Ser Lys Leu Ala Ala Tyr Asn Lys
1               5                   10

<210> SEQ ID NO 95
<211> LENGTH: 17
<212> TYPE: PRT
<213> ORGANISM: Artificial Sequence
<220> FEATURE:
<223> OTHER INFORMATION: Synthetic

<400> SEQUENCE: 95

Leu Ile Leu Pro Gly Glu Leu Ala Lys His Ala Val Ser Glu Gly Thr
1               5                   10                  15
Arg

<210> SEQ ID NO 96
<211> LENGTH: 10
<212> TYPE: PRT
<213> ORGANISM: Artificial Sequence
<220> FEATURE:
<223> OTHER INFORMATION: Synthetic

<400> SEQUENCE: 96

Phe Gln Lys Ser Thr Glu Leu Leu Ile Arg
1               5                   10

<210> SEQ ID NO 97
<211> LENGTH: 11
<212> TYPE: PRT
```

<213> ORGANISM: Artificial Sequence
<220> FEATURE:
<223> OTHER INFORMATION: Synthetic

<400> SEQUENCE: 97

Asp Ser Val Thr Tyr Thr Glu His Ala Lys Arg
1               5                   10

<210> SEQ ID NO 98
<211> LENGTH: 13
<212> TYPE: PRT
<213> ORGANISM: Artificial Sequence
<220> FEATURE:
<223> OTHER INFORMATION: Synthetic

<400> SEQUENCE: 98

Lys Thr Val Thr Ser Leu Asp Val Val Tyr Ala Leu Lys
1               5                   10

<210> SEQ ID NO 99
<211> LENGTH: 13
<212> TYPE: PRT
<213> ORGANISM: Artificial Sequence
<220> FEATURE:
<223> OTHER INFORMATION: Synthetic

<400> SEQUENCE: 99

Thr Val Thr Ser Leu Asp Val Val Tyr Ala Leu Lys Arg
1               5                   10

<210> SEQ ID NO 100
<211> LENGTH: 8
<212> TYPE: PRT
<213> ORGANISM: Artificial Sequence
<220> FEATURE:
<223> OTHER INFORMATION: Synthetic

<400> SEQUENCE: 100

Gly Met Gly Lys Val Gly Ala Lys
1               5

<210> SEQ ID NO 101
<211> LENGTH: 10
<212> TYPE: PRT
<213> ORGANISM: Artificial Sequence
<220> FEATURE:
<223> OTHER INFORMATION: Synthetic

<400> SEQUENCE: 101

Lys Ser Ala Pro Ala Thr Gly Gly Ile Lys
1               5                   10

<210> SEQ ID NO 102
<211> LENGTH: 10
<212> TYPE: PRT
<213> ORGANISM: Artificial Sequence
<220> FEATURE:
<223> OTHER INFORMATION: Synthetic

<400> SEQUENCE: 102

Tyr Gln Lys Ser Thr Asp Leu Leu Ile Arg
1               5                   10

<210> SEQ ID NO 103
<211> LENGTH: 12
<212> TYPE: PRT
<213> ORGANISM: Artificial Sequence

```
<220> FEATURE:
<223> OTHER INFORMATION: Synthetic

<400> SEQUENCE: 103

Val Thr Ile Met Thr Lys Asp Met Gln Leu Ala Arg
1               5                   10

<210> SEQ ID NO 104
<211> LENGTH: 9
<212> TYPE: PRT
<213> ORGANISM: Artificial Sequence
<220> FEATURE:
<223> OTHER INFORMATION: Synthetic

<400> SEQUENCE: 104

Lys Ala Pro Ala Ala Ala Ala Glu Lys
1               5

<210> SEQ ID NO 105
<211> LENGTH: 10
<212> TYPE: PRT
<213> ORGANISM: Artificial Sequence
<220> FEATURE:
<223> OTHER INFORMATION: Synthetic

<400> SEQUENCE: 105

Lys Ala Pro Ala Ala Ala Ala Glu Lys Lys
1               5                   10

<210> SEQ ID NO 106
<211> LENGTH: 13
<212> TYPE: PRT
<213> ORGANISM: Artificial Sequence
<220> FEATURE:
<223> OTHER INFORMATION: Synthetic

<400> SEQUENCE: 106

Val Leu Lys Gln Val His Pro Asp Val Gly Ile Ser Lys
1               5                   10

<210> SEQ ID NO 107
<211> LENGTH: 10
<212> TYPE: PRT
<213> ORGANISM: Artificial Sequence
<220> FEATURE:
<223> OTHER INFORMATION: Synthetic

<400> SEQUENCE: 107

Ile Ala Leu Glu Ser Ser Lys Leu Val Arg
1               5                   10

<210> SEQ ID NO 108
<211> LENGTH: 12
<212> TYPE: PRT
<213> ORGANISM: Artificial Sequence
<220> FEATURE:
<223> OTHER INFORMATION: Synthetic

<400> SEQUENCE: 108

His Ala Ile Ser Glu Gly Thr Lys Ala Val Thr Lys
1               5                   10

<210> SEQ ID NO 109
<211> LENGTH: 10
<212> TYPE: PRT
<213> ORGANISM: Artificial Sequence
<220> FEATURE:
```

```
<223> OTHER INFORMATION: Synthetic

<400> SEQUENCE: 109

Ala Val Thr Lys Phe Ser Ser Ser Thr Asn
1               5                   10

<210> SEQ ID NO 110
<211> LENGTH: 11
<212> TYPE: PRT
<213> ORGANISM: Artificial Sequence
<220> FEATURE:
<223> OTHER INFORMATION: Synthetic

<400> SEQUENCE: 110

Ala Gly Gly Lys Ala Gly Lys Asp Ser Gly Lys
1               5                   10

<210> SEQ ID NO 111
<211> LENGTH: 9
<212> TYPE: PRT
<213> ORGANISM: Artificial Sequence
<220> FEATURE:
<223> OTHER INFORMATION: Synthetic

<400> SEQUENCE: 111

Thr Ala Ser Ser Lys Gln Val Ser Arg
1               5

<210> SEQ ID NO 112
<211> LENGTH: 10
<212> TYPE: PRT
<213> ORGANISM: Artificial Sequence
<220> FEATURE:
<223> OTHER INFORMATION: Synthetic

<400> SEQUENCE: 112

Ser Ala Pro Ala Pro Lys Lys Gly Ser Lys
1               5                   10
```